United States Patent
Garcia Santana

(10) Patent No.: US 9,910,039 B2
(45) Date of Patent: Mar. 6, 2018

(54) REGULATORY T CELLS AND METHODS OF IDENTIFYING, OBTAINING AND USING TO TREAT IMMUNO-BASED DISORDERS

(75) Inventor: Carlos A. Garcia Santana, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 286 days.

(21) Appl. No.: 14/129,007

(22) PCT Filed: Jun. 29, 2012

(86) PCT No.: PCT/US2012/045049
§ 371 (c)(1),
(2), (4) Date: Apr. 11, 2014

(87) PCT Pub. No.: WO2013/006474
PCT Pub. Date: Jan. 10, 2013

(65) Prior Publication Data
US 2015/0004176 A1    Jan. 1, 2015

Related U.S. Application Data

(60) Provisional application No. 61/504,074, filed on Jul. 1, 2011, provisional application No. 61/625,591, filed on Apr. 17, 2012.

(51) Int. Cl.
| | |
|---|---|
| *C12N 5/071* | (2010.01) |
| *G01N 33/569* | (2006.01) |
| *C12N 5/0783* | (2010.01) |
| *G01N 33/50* | (2006.01) |
| *A61K 35/17* | (2015.01) |
| *C07K 16/28* | (2006.01) |

(52) U.S. Cl.
CPC ....... *G01N 33/56972* (2013.01); *A61K 35/17* (2013.01); *C07K 16/2896* (2013.01); *C12N 5/0637* (2013.01); *G01N 33/505* (2013.01); *G01N 2333/70596* (2013.01)

(58) Field of Classification Search
None
See application file for complete search history.

(56) References Cited

U.S. PATENT DOCUMENTS

| | | |
|---|---|---|
| 6,372,215 B1 | 4/2002 | Starling et al. |
| 6,572,857 B1 | 6/2003 | Casimiro et al. |
| 2003/0232433 A1* | 12/2003 | Gunther ............ A61K 35/28 435/372 |
| 2005/0186207 A1 | 8/2005 | Bluestone |
| 2006/0105336 A1 | 5/2006 | Zang |
| 2008/0131445 A1 | 6/2008 | Bluestone et al. |

FOREIGN PATENT DOCUMENTS

WO    WO 2006/138059    12/2006

OTHER PUBLICATIONS

Osorio et al., 1998, Immunology, vol. 93: 358-365.*
Kolb et al., Ann. Hematol, 2008, suppl 1 S65-S67 Smith et al., 2008, Trends in Immunol. vol. 29: 337-342.*
Sakaguchi et al., Published online Jun. 2010, Nat. Rev. vol. 10: 490-500 Seddiki et al., 2006, Blood vol. 107: 2830-2838.*
Stephens et al., 2004, Int. Immunol. vol. 16: 365-375.*
Tuo et al., 1999, J. Immunol. vol. 162: 245-253.*
Rasmussen et al., 1994, J. Immunol. vol. 152: 527-536.*
Akamizu, "Monoclonal antibodies to thyroid specific autoantigens", Autoimmunity, 36(6-7):361-366 (Sep.-Nov. 2003).
Apostolou et al., "In Vivo Instruction of Suppressor Commitment in Naïve T Cells", J. Exp. Med. 199(10):1401-1408 (2003).
Belghith et al., "TGF-beta-dependent mechanisms mediate restoration of self-tolerance induced by antibodies to CD3 in overt autoimmune diabetes", Nat. Med. 9(9):1202-1208 (Sep. 2003).
Butterfield et al., "T-Cell responses to HLA-A0201 immunodominant peptides derived from alpha-fetoprotein in patients with hepatocellular cancer", Clin. Cancer Res., 9(16 Pt 1):5902-5908 (Dec. 1, 2003).
International Search Report for related International Patent Application PCT/US2012/045049 (Pub WO 2013/006474 A3).
Kim et al., "The ABCs of artificial antigen presentation", Nat. Biotechnol, 22(4):403-410 (2004).
Kita et al., "Application of Tetramer Technology in Studies on Autoimmune Diseases", Autoimmun. Rev. 2(1):43-49 (Jan. 2003).
Kolb et al., "HLA-Haploidentical Stem Cell Transplant-action in AML/MDS Using Marrow and CD6-Depleted Mobilized Blood Cells", Acute Leukemias XII—Biology and Treatment Strategies Feb. 16-20, 2008, Munich, Germany Main Sessions Annals of Hematology, 87(Suppl 1):S65-S67 (2008).
Maus et al., "Ex vivo expansion of polyclonal and antigen-specific cytotoxic T lymphocytes by artificial APCs expressing ligands for the T-cell receptor, CD28 and 4-1BB" Nat. Biotechnol. 20:143-148 (2002).
McMillan, "Antiplatelet antibodies in chronic adult immune thrombocytopenic purpura: assays and epitopes" J. Pediatr. Hematol. Oncol. 25(Suppl 1):S57-S61 (Dec. 2003).
Mougiakakos et al., "Naturally Occuring Regulatory T Cells Show Reduced Sensitivity Toward Oxidative Stress-induced Cell Death", Blood, 113(15):3542-3545 (Apr. 9, 2009).
Nummer et al., "Role of Tumor Endothelium in CD4+CD25+ Regulatory T Cell Infiltration of Human Pancreatic Carcinoma", JNCI Journal of the National Cancer Institute, 99(15):1188-1199 (Aug. 1, 2007).
Pluckthun, "Antibodies from *Escherichia coli*", The Pharmacology of Monoclonal Antibodies, 113:269-315 (1994).
Robinson et al., "Protein arrays for autoantibody profiling and fine-specificity mapping"; Proteomics, 2:2077-2084 (2003).

(Continued)

*Primary Examiner* — Amy E Juedes
(74) *Attorney, Agent, or Firm* — Merchant & Gould P.C.

(57) ABSTRACT

The present specification discloses regulatory T cells, compositions including regulatory T cells, methods of identifying, isolating, enriching, obtaining, and/or expanding regulatory T cells or subset populations thereof, kits including components useful for performing such methods, and methods of treating an immune-based disorder in an individual by administering regulatory T cells or compositions comprising such regulatory T cells to an individual in need thereof.

9 Claims, 15 Drawing Sheets

(56) References Cited

OTHER PUBLICATIONS

Sakaguchi et al., "FOXP3 + Regulatory T Cells in the Human Immune System", Nature Reviews, 10(7):1474-1733 (Jul. 1, 2010).
Shimizu et al., "Stimulation of CD25(+)CD4(+) regulatory T cells through GITR breaks immunological self-tolerance", Nat. Immunol., 3(2):135-142 (Jan. 22, 2002).
Smith et al., "Revival of CD8<+> Treg-mediated Suppression", Trends in Immuniligy, 29(7):337-339 (Jul. 1, 2008).
Stephens, L.A et al., "Phenotypic characterization of regulatory CD4+CD25+ T cells in rats." Int. lmmunol (2004),. vol. 16: 365-375.
Thomas et al., "A cell-based artificial antigen-presenting cell coated with anti-CD3 and CD28 antibodies enables rapid expansion and long-term growth of CD4 T lymphocytes", Clin. Immunol. 105(3):259-272 (Dec. 2002).
Tone et al., "Mouse glucocorticoid-induced tumor necrosis factor receptor ligand is costimulatory for T cells", PNAS, 100(25):15059-15064 (Nov. 7, 2003).
Tuo et al., "Differential Effects of Type I IFNs on the Growth of WC1-CD8+ T Cells and WC1 + CDS-T Cells in Vitro1", Journal of Immunology, (1999), vol. 162, No. 1, pp. 245-253.
Wang et al., "Expression of GARP Selectively Identifies Activated Human FOXP3$^+$ Regulatory T Cells", PNAS, 106(32):13439-13444 (Jul. 28, 2009).
Yamazaki et al.,"Direct Expansion of Functional CD25$^+$ CD4$^+$ Regulatory T Cells by Antigen-processing Dendritic Cells", J. Exp. Med. 198(2):235-247 (Jul. 21, 2003).
Yee et al., "Isolation of High Avidity Melanoma-Reactive CTL from Heterogeneous Populations Using Peptide-MHC Tetramers", J. Immunol., 162(4):2227-2234 (Feb. 15, 1999).
Yee et al., , "Adoptive T cell therapy using antigen-specific CD8$^+$ T cell clones for the treatment of patients with metastatic melanoma: In vivo persistence, migration and antitumor effect of transferred T cells", PNAS, 99(25):16168-16173 (Dec. 10, 2002).

\* cited by examiner

A

B

REGULATORY T CELLS AND METHODS OF IDENTIFYING, OBTAINING AND USING TO TREAT IMMUNO-BASED DISORDERS

This application is a National Stage Application of PCT/US2012/045049, filed 29 Jun. 2012, which claims benefit of U.S. Provisional Ser. No. 61/504,074, filed 1 Jul. 2011, and U.S. Provisional Ser. No. 61/625,591, filed 17 Apr. 2012 and which applications are incorporated herein by reference. To the extent appropriate, a claim of priority is made to each of the above disclosed applications.

BACKGROUND

T cells or T lymphocytes belong to a group of white blood cells known as lymphocytes, and play a central role in cell-mediated immunity. They can be distinguished from other lymphocyte types, such as B cells, by the presence of a special receptor on their cell surface called T cell receptors (TCR). Several different subsets of T cells have been discovered, each with a distinct function including T helper cell ($T_H$ cells), Cytotoxic T cells ($T_C$ cells, or CTLs), Memory T cells ($T_M$ cells) including central memory T cells ($T_{CM}$ cells) and effector memory T cells ($T_{EM}$ cells), Natural killer T cells (NKT cells), gamma delta T cells (γδT cells), and regulatory T cells ($T_{reg}$ cells).

Regulatory T cells, also known as suppressor T cells, are a specialized subpopulation of T cells that act to suppress immune responses of other cells. For example, $T_{reg}$ cells play a major role in suppressing T cell-mediated immunity during an immune reaction and in suppressing auto-reactive T cells that escaped the process of negative selection in the thymus. As such, $T_{reg}$ cells provide an important "self-check" to prevent excessive immunogenic reactions and are thus crucial for the maintenance of immune system homeostasis and tolerance to self-antigens.

Two major classes of $T_{reg}$ cells are the naturally-occurring $T_{reg}$ cells and the adaptive $T_{reg}$ cells. Naturally occurring $T_{reg}$ cells (also known as $CD4^+CD25^+FoxP3^+$ $T_{reg}$ cells) arise in the thymus and have been linked to interactions between developing T cells with both myeloid ($CD11c^+$) and plasmacytoid ($CD123^+$) dendritic cells that have been activated with TSLP. Adaptive $T_{reg}$ cells (including Tr1 cells, Th2 cells, Th3 cells, and Th17 cells) appear to originate in the periphery during a normal immune response and seem to promote $T_{reg}$ cell development and function.

Adaptive $T_{reg}$ cells share many of the attributes of naturally-occurring $T_{reg}$ cells but can differ in critical cell surface biomarkers and functional attributes. For instance, Tr1 and Th3 cells have been described that produce IL-10 and TGFβ, respectively. These results have led to novel approaches to immunotherapy as the ability to isolate, enrich, and expand this cell subset in mice has led to novel therapeutic interventions in immunological diseases.

The identification of naturally-occurring $T_{reg}$ cells as an important component of self-tolerance has opened a major area of investigation in immunology and the basic process that control immune tolerance. Regulatory T cells have a unique and robust therapeutic profile. The cells require specific T cell receptor (TCR)-mediated activation to develop regulatory activity but their effector function appears to be non-specific, regulating local inflammatory responses through a combination of cell-cell contact and suppressive cytokine production. Numerous studies have demonstrated the potent influence of naturally-occurring $T_{reg}$ cell in suppressing pathologic immune responses in autoimmune diseases, transplantation, and graft-vs-host diseases. However, a major obstacle to the study and application of naturally-occurring $T_{reg}$ cells in the human setting has been the lack of specific cell surface biomarkers to define and separate $T_{reg}$ cells from other subsets of T cells such as, e.g., $T_H$ cells, $T_C$ cells, $T_{CM}$ cells, $T_{EM}$ cells as well as to distinguish between different subpopulations of $T_{reg}$ cells.

A number of different methods are employed in research to identify, isolate, enrich, or otherwise exploit $T_{reg}$ cells. The most widely used markers for naturally-occurring $T_{reg}$ cells are cluster of differentiation 4 (CD4), cluster of differentiation 25 (CD25), forkhead/winged-helix transcription factor box P3 (FoxP3), cytotoxic T lymphocyte-associated antigen 4 (CTLA-4), glucocorticoid-induced tumor necrosis factor receptor family-related gene (GITR), lymphocyte activation gene-3 (LAG-3), and cluster of differentiation 127 (CD127). Unfortunately, accumulating evidence suggests that the above-listed markers are not strictly $T_{reg}$ cell-specific. For example, high expression of CD25 and CD4 surface markers ($CD4^+CD25^+$ cells) was originally used to identify naturally-occurring $T_{reg}$ cells. However, CD4 is also expressed on $T_H$ cells, and a subpopulation of $T_M$ cells. CD25 is also expressed on non-regulatory T cells in the setting of immune activation such as during an immune response to a pathogen. Thus, as defined by CD4 and CD25 expression, $T_{reg}$ cells comprise about 5-10% of mature $T_H$ cells. The additional measurement of cellular expression of Foxp3 allowed a more specific analysis of naturally-occurring $T_{reg}$ cells ($CD4^+CD25^+FoxP3^+$ cells). However, Foxp3 is also transiently expressed in activated $T_{EM}$ cells and it is now well documented that most human $CD4^+$ and $CD8^+$ T cells transiently express Foxp3 upon activation, including $CD4^+$ $CD25^{low/-}$ T cells, $T_H$ cells, $T_C$ cells, and memory T cells. Furthermore, FoxP3 is a nuclear marker requires cell membrane permeabilization prior to staining. As such, use of this biomarker precludes subsequent processing steps such as separating, isolating, enriching, or expanding viable naturally-occurring $T_{reg}$ cells for functional studies or for use in an immunotherapy.

It has been suggested that the addition of CD127 could be used to discriminate between naturally-occurring $T_{reg}$ cells (which exhibit a $CD127^{low/-}$ expression pattern) and $T_H$ cells (which exhibit a $CD127^+$ expression pattern) in humans. However, it has been recently reported that most $CD4^+$ T cells down-regulate CD127 upon activation. Furthermore, loss of CD127 is a characteristic feature of T follicular helper cells ($T_{FH}$ cells), which provide help for B cells in human tonsils. CTLA-4 is a negative regulator of T-cell activation, which is up-regulated on all $CD4^+$ and $CD8^+$ T cells, 2-3 days following activation. Similarly, the expression of GITR and LAG-3 is induced in $T_{EM}$ cells upon activation. Thus, all the presently-used $T_{reg}$ cell biomarkers (CD25, CTLA-4, GITR, CD127, LAG-3, GARP and FoxP3) appear to be general T-cell activation markers. As such, these biomarkers do not appear to be $T_{reg}$-cell-specific and therefore are not reliable for distinguishing naturally-occurring $T_{reg}$ cells from other T cell subsets like activated $T_H$ cells. Thus, it is likely that many of the natural and adaptive regulatory T cells are missed in current biomarker studies, calling into question the conclusions related to deficiencies or defects in certain autoimmune settings.

Thus there is a need to develop improved methods of identifying, isolating, enriching, and expanding a population of immunosuppressive regulatory T-cells as well as methods of modulating an immune reaction in an individual. Additionally, there is a need to develop compositions comprising a population of immunosuppressive regulatory T-cell as well as uses of such compounds for modulating an immune reaction in an individual. Lastly, there is a need to develop kits comprising biomarkers and/or other components useful to conduct the above described methods.

SUMMARY

The present disclosure relates to the discovery that a cluster of differentiation 6 (CD6) is a particularly useful biomarker in identifying immunosuppressive regulatory T cells in general, as well as identifying distinct subpopulations of immunosuppressive regulatory T cells when used in conjunction with another biomarker.

Accordingly, aspects of the present specification disclose a method of identifying a population of immunosuppressive regulatory T-cells, the method comprising screening a sample comprising a population of T-cells to detect a level of cellular expression of a CD6 biomarker wherein detection of a subpopulation of T-cells comprising a $CD6^{low/-}$ expression pattern identifies the population of immunosuppressive regulatory T-cells in the sample. In an aspect, a method of identifying a population of immunosuppressive regulatory T-cells, the method comprising screening a sample comprising a population of T-cells to detect a level of cellular expression of at least two different biomarkers, the at least two different biomarkers including a CD25 biomarker and a CD6 biomarker; wherein detection of a subpopulation of T-cells comprising a $CD25^+$ $CD6^{low/-}$ expression pattern identifies the population of immunosuppressive regulatory T-cells in the sample. In another aspect, a method of identifying a population of immunosuppressive regulatory T-cells, the method comprising screening a sample comprising a population of T-cells to detect a level of cellular expression of at least three different biomarkers, the at least three different biomarkers including a CD4 biomarker, a CD25 biomarker, and a CD6 biomarker; wherein detection of a subpopulation of T-cells comprising a $CD4^+$ $CD25^+$ $CD6^{low/-}$ expression pattern identifies the population of immunosuppressive regulatory T-cells in the sample.

In another aspect, a method of identifying a population of immunosuppressive regulatory T-cells, the method comprising contacting a sample comprising a population of T-cells with a CD6 biomarker ligand; and screening the population of T-cells to detect a level of cellular expression of a CD6 biomarker; and wherein detection of a subpopulation of T-cells comprising a $CD6^{low/-}$ expression pattern identifies the population of immunosuppressive regulatory T-cells in the sample. In yet another aspect, a method of identifying a population of immunosuppressive regulatory T-cells, the method comprising contacting a sample comprising a population of T-cells with at least two different biomarker ligands, wherein the at least two different biomarker ligands include a CD25 biomarker ligand and a CD6 biomarker ligand; and screening the population of T-cells to detect a level of cellular expression of at least two different biomarkers; wherein the at least two different biomarkers include a CD25 biomarker and a CD6 biomarker; and wherein detection of a subpopulation of T-cells comprising a $CD25^+$ $CD6^{low/-}$ expression pattern identifies the population of immunosuppressive regulatory T-cells in the sample. In still another aspect, a method of identifying a population of immunosuppressive regulatory T-cells, the method comprising contacting a sample comprising a population of T-cells with at least three different biomarker ligands, wherein the at least three different biomarker ligands include a CD4 biomarker ligand, a CD25 biomarker ligand, and a CD6 biomarker ligand; and screening the population of T-cells to detect a level of cellular expression of at least three different biomarkers; wherein the at least three different biomarkers include a CD4 biomarker, a CD25 biomarker, and a CD6 biomarker; and wherein detection of a subpopulation of T-cells comprising a $CD4^+$ $CD25^+$ $CD6^{low/-}$ expression pattern identifies the population of immunosuppressive regulatory T-cells in the sample.

A sample may comprise T cells obtained from blood, such as, e.g., isolated from peripheral blood mononuclear cell (PBMC), lymphoid, thymus, bone marrow, or any specific tissues/organ sample of interest, including, without limitation, pancreas, eye, heart, liver, nerves, intestine, skin, muscle, cartilage, ligament, synovial fluid, and/or joints. Other biomarkers that may be used include a CD127 biomarker, a cluster of differentiation 49d (CD49d) biomarker, a cluster of differentiation 38 (CD38) biomarker, a cluster of differentiation 45RA (CD45RA) biomarker, a human leukocyte antigen serotype DR (HLA-DR) biomarker, a FoxP3 biomarker, a CTLA-4 biomarker, a GITR biomarker, a LAG-3 biomarker, a ectonucleotidase (CD39) biomarker, a member of Ikaros family zinc-finger nuclear proteins (Helios) biomarker, a orphan receptor FcRL3 (FcRL3) biomarker, a cytokine receptor 7 (CCR7 or CD197) biomarker, a cytokine receptor 4 (CCR4 or CD194) biomarker, a cytokine receptor 8 (CCR8 or CDw198), a cluster of differentiation CD62L (CD62L) biomarker, a Inducible T-cell co-stimulator (ICOS or CD278) biomarker, a cluster of differentiation 103 (CD103) biomarker, a programmed dead-1 (PD-1) biomarker, a member of the tumor necrosis factor receptor superfamily OX40 (CD134) biomarker, a glycoprotein-A repetitions predominant (GARP) biomarker, a cluster of differentiation 45RB (CD45RB) biomarker, a cluster of differentiation 45RO (CD45RO) biomarker, a cluster of differentiation 95 (CD95) biomarker, a cluster of differentiation 122 (CD122) biomarker, a cluster of differentiation 147 (CD147), a cluster of differentiation 8 (CD8) biomarker, or any combination thereof. The use of these additional biomarkers is particularly useful in identifying subpopulations of immunosuppressive regulatory T-cells. The disclosed biomarker may be antibodies or ligands and may be labeled or unlabeled. If labeled, the biomarker may be labeled with a fluorophore, a quantum dot, a phosphor, a chemiluminescent compound, a bioluminescent compound, a chromogenic compound, an isotope compound like a lanthanide, a radioisotope, an enzyme, a biotin or avidin molecule, or any other label useful for detecting a cell bound by the biomarker. The identifying step, including the samples and useful biomarkers are as disclosed herein. The identifying step may use labeled biomarkers with flow cytometer, cell sorter, magnetic particles/bead, complement lysis, cell panning or other methodologies known to one of ordinary skill in the art for isolating or enriching cells. In yet another aspect, a disclosed method has the proviso that the biomarkers used to screen a sample does not include a FoxP3 biomarker, a CTLA-4 biomarker, or both a FoxP3 biomarker and a CTLA-4 biomarker. The methods disclosed herein may further comprise isolating or enriching the identified population of immunosuppressive regulatory T-cells. The methods disclosed herein may further comprise expanding the identified, isolated or enriched population of immunosuppressive regulatory T-cells.

Other aspects of the present specification disclose a method of obtaining a population of immunosuppressive regulatory T-cells, the method comprising screening a sample comprising a population of T-cells to detect a level of cellular expression of a CD6 biomarker as disclosed herein and isolating a subpopulation of T-cells comprising a CD6$^{low/-}$ expression pattern, thereby obtaining the population of immunosuppressive regulatory T-cells. In an aspect, a method of obtaining a population of immunosuppressive regulatory T-cells, the method comprising screening a sample comprising a population of T-cells to detect a level of cellular expression of at least two different biomarkers, the at least two different biomarkers including a CD25 biomarker and a CD6 biomarker; and isolating a subpopulation of T-cells comprising a CD25$^+$ CD6$^{low/-}$ expression pattern, thereby obtaining the population of immunosuppressive regulatory T-cells. In another aspect, a method of obtaining a population of immunosuppressive regulatory T-cells, the method comprising screening a sample comprising a population of T-cells to detect a level of cellular expression of at least three different biomarkers, the at least three different biomarkers including a CD4 biomarker, a CD25 biomarker, and a CD6 biomarker; and isolating a subpopulation of T-cells comprising a CD4$^+$ CD25$^+$ CD6$^{low/-}$ expression pattern, thereby obtaining the population of immunosuppressive regulatory T-cells.

In another aspect, a method of obtaining a population of immunosuppressive regulatory T-cells, the method comprising contacting a sample comprising a population of T-cells with a CD6 biomarker ligand; screening the population of T-cells to detect a level of cellular expression of a CD6 biomarker; and isolating a subpopulation of T-cells comprising a CD6$^{low/-}$ expression pattern, thereby obtaining the population of immunosuppressive regulatory T-cells. In yet another aspect, a method of obtaining a population of immunosuppressive regulatory T-cells, the method comprising contacting a sample comprising a population of T-cells with at least two different biomarker ligands, wherein the at least two different biomarker ligands include a CD25 biomarker ligand and a CD6 biomarker ligand; screening the population of T-cells to detect a level of cellular expression of at least two different biomarkers; wherein the at least two different biomarkers include a CD25 biomarker and a CD6 biomarker; and isolating a subpopulation of T-cells comprising a CD25$^+$ CD6$^{low/-}$ expression pattern, thereby obtaining the population of immunosuppressive regulatory T-cells. In still another aspect, a method of obtaining a population of immunosuppressive regulatory T-cells, the method comprising contacting a sample comprising a population of T-cells with at least three different biomarker ligands, wherein the at least three different biomarker ligands include a CD4 biomarker ligand, a CD25 biomarker ligand, and a CD6 biomarker ligand; screening the population of T-cells to detect a level of cellular expression of at least three different biomarkers; wherein the at least three different biomarkers include a CD4 biomarker, a CD25 biomarker, and a CD6 biomarker; and isolating a subpopulation of T-cells comprising a CD4$^+$ CD25$^+$ CD6$^{low/-}$ expression pattern, thereby obtaining the population of immunosuppressive regulatory T-cells.

The identifying step, including the samples and useful biomarkers are as disclosed herein. The isolating step may use labeled biomarkers with flow cytometer, cell sorter, magnetic particles/bead, or other methodologies known to one of ordinary skill in the art for isolating cells. The identifying and isolating can proceed in any order or simultaneously by the use of multiple, distinguishable biomarkers used to detect the common determinants. In yet another aspect, a disclosed method has the proviso that the biomarkers used to screen and/or isolate a sample does not include a FoxP3 biomarker, a CTLA-4 biomarker, or both a FoxP3 biomarker and a CTLA-4 biomarker. The methods disclosed herein may further comprise enriching or expanding the isolated subpopulation of immunosuppressive regulatory T-cells.

Yet other aspects of the present specification disclose a method of obtaining an expanded population of immunosuppressive regulatory T-cells, the method comprising screening a sample comprising a population of T-cells to detect a level of cellular expression of a CD6 biomarker as disclosed herein, isolating a subpopulation of T-cells comprising a CD6$^{low/-}$ expression pattern as disclosed herein, and contacting the subpopulation of T-cells comprising a CD6$^{low/-}$ expression pattern with a stimulatory composition, thereby obtaining the expanded population of immunosuppressive regulatory T-cells. In an aspect, a method of obtaining an expanded population of immunosuppressive regulatory T-cells, the method comprising the steps of screening a sample comprising a population of T-cells to detect a level of cellular expression of at least two different biomarkers, the at least two different biomarkers including a CD25 biomarker and a CD6 biomarker; isolating a subpopulation of T-cells comprising a CD25$^+$ CD6$^{low/-}$ expression pattern; and contacting the subpopulation of T-cells comprising a CD25$^+$ CD6$^{low/-}$ expression pattern with a stimulatory composition, thereby obtaining the expanded population of immunosuppressive regulatory T-cells. In another aspect, a method of obtaining an expanded population of immunosuppressive regulatory T-cells, the method comprising the steps of screening a sample comprising a population of T-cells to detect a level of cellular expression of at least three different biomarkers, the at least three different biomarkers including a CD4 biomarker, a CD25 biomarker, and a CD6 biomarker; isolating a subpopulation of T-cells comprising a CD4$^+$ CD25$^+$ CD6$^{low/-}$ expression pattern; and contacting the subpopulation of T-cells comprising a CD4$^+$ CD25$^+$ CD6$^{low/-}$ expression pattern with a stimulatory composition, thereby obtaining the expanded population of immunosuppressive regulatory T-cells.

In another aspect, a method of obtaining an expanded population of immunosuppressive regulatory T-cells, the method comprising the steps of contacting a sample comprising a population of T-cells with a CD6 biomarker ligand; screening the population of T-cells to detect a level of cellular expression of a CD6 biomarker; isolating a subpopulation of T-cells comprising a CD6$^{low/-}$ expression pattern; and contacting the subpopulation of T-cells comprising a CD6$^{low/-}$ expression pattern with a stimulatory composition, thereby obtaining the expanded population of immunosuppressive regulatory T-cells. In yet another aspect, a method of obtaining an expanded population of immunosuppressive regulatory T-cells, the method comprising the steps of contacting a sample comprising a population of T-cells with at least two different biomarker ligands, wherein the at least two different biomarker ligands include a CD25 biomarker ligand and a CD6 biomarker ligand; screening the population of T-cells to detect a level of cellular expression of at least two different biomarkers; wherein the at least two different biomarkers include a CD25 biomarker and a CD6 biomarker; isolating a subpopulation of T-cells comprising a CD25$^+$ CD6$^{low/-}$ expression pattern; and contacting the subpopulation of T-cells comprising a CD25$^+$ CD6$^{low/-}$ expression pattern with a stimulatory composition, thereby obtaining the expanded population of immunosuppressive regulatory T-cells. In still another aspect, a method of obtaining an expanded population of immunosuppressive regulatory T-cells, the method comprising the steps of contacting a sample comprising a population of T-cells with at least three different biomarker ligands, wherein the at least three different biomarker ligands include a CD4 biomarker ligand, a CD25 biomarker ligand, and a CD6 biomarker ligand; screening the population of T-cells to detect a level of cellular expression of at least three different biomarkers; wherein the at least three different biomarkers include a CD4 biomarker, a CD25 biomarker, and a CD6 biomarker; isolating a subpopulation of T-cells comprising a CD4$^+$ CD25$^+$ CD6$^{low/-}$ expression pattern; and contacting the subpopulation of T-cells comprising a CD4$^+$ CD25$^+$ CD6$^{low/-}$ expression pattern with a stimulatory composition, thereby obtaining the expanded population of immunosuppressive regulatory T-cells.

The identifying step, including the samples and useful biomarkers as well as the isolating step, including labeled biomarkers and methodologies are as disclosed herein. A stimulatory composition comprises a TCR/CD3 activator that is antigen-specific and may further comprise one or more additional agents including a co-stimulatory agent, a second regulatory T cell stimulatory agent, or a T cell survival or growth agent. Alternatively, the subpopulation T-cells with a desired expression pattern can first be enriched or expanded and then isolated as disclosed herein.

Still other aspects of the present specification disclose a method of modulating an immune reaction in an individual, the method comprising obtaining a biological sample, the biological sample comprising a population of individual-compatible T-cells; screening a sample comprising a population of T-cells to detect a level of cellular expression of a CD6 biomarker; isolating a subpopulation of T-cells comprising a CD6$^{low/-}$ expression pattern; and administering the subpopulation T-cells with a CD6$^{low/-}$ expression pattern into the individual, thereby treating an immune-based disorder in the individual. In an aspect, a method of modulating an immune reaction in an individual, the method comprising obtaining a biological sample, the biological sample comprising a population of individual-compatible T-cells; screening a sample comprising a population of T-cells to detect a level of cellular expression of at least two different biomarkers, the at least two different biomarkers including a CD25 biomarker and a CD6 biomarker; isolating a subpopulation of T-cells comprising a CD25$^+$ CD6$^{low/-}$ expression pattern; and administering the subpopulation T-cells with a CD25$^+$ CD6$^{low/-}$ expression pattern into the individual, thereby treating an immune-based disorder in the individual. In another aspect, a method of modulating an immune reaction in an individual, the method comprising obtaining a biological sample, the biological sample comprising a population of individual-compatible T-cells; screening a sample comprising a population of T-cells to detect a level of cellular expression of at least three different biomarkers, the at least three different biomarkers including a CD4 biomarker, a CD25 biomarker, and a CD6 biomarker; isolating a subpopulation of T-cells comprising a CD4$^+$ CD25$^+$ CD6$^{low/-}$ expression pattern; and administering the subpopulation T-cells with a CD4$^+$ CD25$^+$ CD6$^{low/-}$ expression pattern into the individual, thereby treating an immune-based disorder in the individual.

In another aspect, a method of modulating an immune reaction in an individual, the method comprising obtaining a biological sample, the biological sample comprising a population of individual-compatible T-cells; contacting a sample comprising a population of T-cells with a CD6 biomarker ligand; screening the population of T-cells to detect a level of cellular expression of a CD6 biomarker; and isolating a subpopulation of T-cells comprising a CD6$^{low/-}$ expression pattern; and administering the subpopulation T-cells with a CD6$^{low/-}$ expression pattern into the individual, thereby treating an immune-based disorder in the individual. In yet another aspect, a method of modulating an immune reaction in an individual, the method comprising obtaining a biological sample, the biological sample comprising a population of individual-compatible T-cells; contacting a sample comprising a population of T-cells with at least two different biomarker ligands, wherein the at least two different biomarker ligands include a CD25 biomarker ligand and a CD6 biomarker ligand; screening the population of T-cells to detect a level of cellular expression of at least two different biomarkers; wherein the at least two different biomarkers include a CD25 biomarker and a CD6 biomarker; and isolating a subpopulation of T-cells comprising a CD25$^+$ CD6$^{low/-}$ expression pattern; and administering the subpopulation T-cells with a CD25$^+$ CD6$^{low/-}$ expression pattern into the individual, thereby treating an immune-based disorder in the individual. In still another aspect, a method of modulating an immune reaction in an individual, the method comprising obtaining a biological sample, the biological sample comprising a population of individual-compatible T-cells; contacting a sample comprising a population of T-cells with at least three different biomarker ligands, wherein the at least three different biomarker ligands include a CD4 biomarker ligand, a CD25 biomarker ligand, and a CD6 biomarker ligand; screening the population of T-cells to detect a level of cellular expression of at least three different biomarkers; wherein the at least three different biomarkers include a CD4 biomarker, a CD25 biomarker, and a CD6 biomarker; and isolating a subpopulation of T-cells comprising a CD4$^+$ CD25$^+$ CD6$^{low/-}$ expression pattern; and administering the subpopulation T-cells with a CD4$^+$ CD25$^+$ CD6$^{low/-}$ expression pattern into the individual, thereby treating an immune-based disorder in the individual.

The identifying step, including the samples and useful biomarkers as well as the isolating step, including labeled biomarkers and methodologies are as disclosed herein. The disclosed methods may further comprise enriching or expanding the subpopulation T-cells with a desired expression pattern as disclosed herein prior to administering the subpopulation T-cells into the individual. Alternatively, the population of individual-compatible T-cells in the biological sample can be enriched or expanded before screening the sample as disclosed herein and/or before isolating the subpopulation T-cells with a desired expression pattern as disclosed herein.

Other aspects of the present specification disclose a kit comprising components useful in performing any of the methods disclosed herein. In an aspect, a kit for identifying and/or isolating or enriching a population of immunosuppressive regulatory T-cells comprises a CD6 biomarker ligand. In another aspect, a kit for identifying, isolating and/or enriching a population of immunosuppressive regulatory T-cells comprises at least two different biomarker ligands, wherein the at least two different biomarker ligands include a CD25 biomarker ligand and a CD6 biomarker ligand. In yet another aspect, a kit for identifying, isolating and/or enriching a population of immunosuppressive regulatory T-cells comprises at least three different biomarker ligands, wherein the at least three different biomarker ligands include a CD4 biomarker ligand, a CD25 biomarker ligand, and a CD6 biomarker ligand. Such disclosed kits may further include a CD127 biomarker ligand, a CD49d biomarker ligand, a CD38 biomarker ligand, a CD45RA biomarker ligand, a HLA-DR biomarker ligand, a FoxP3 biomarker ligand, a CTLA-4 biomarker ligand, a GITR biomarker ligand, a LAG-3 biomarker ligand, a CD39 biomarker ligand, a Helios biomarker ligand, a FcRL3 biomarker ligand, a CCR7 biomarker ligand, a CCR4 biomarker ligand, a CCR8 biomarker ligand, a CD62L biomarker ligand, a ICOS biomarker ligand, a CD103 biomarker ligand, a PD-1 biomarker ligand, a CD134 biomarker ligand, a GARP biomarker ligand, a CD45RB biomarker ligand, a CD45RO biomarker ligand, a CD95 biomarker ligand, a CD122 biomarker ligand, a CD147 biomarker ligand, a CD8 biomarker ligand, or any combination thereof. The disclosed biomarker ligands may be antibodies or ligands and may be labeled or unlabeled. If labeled, the biomarker ligand may be labeled with a fluorophore, a quantum dot, a phosphore, a chemiluminescent compound, a bioluminescent compound, a chromogenic compound, an isotope compound like a lanthanide, a radioisotope, an enzyme, a biotin or avidin molecule, or any other label useful for detecting a cell bound by the biomarker. If unlabeled, the kit may further include a label and other reagents useful for labeling a biomarker ligand. In yet another aspect, a kit for expanding a population of immunosuppressive regulatory T-cells comprises a stimulatory composition as disclosed herein. Such a kit may further comprise a CD6 biomarker ligand or at least three different biomarker ligands as disclosed herein. A disclosed kit may further comprise positive and/or negative controls. Additionally, a disclosed kit may further comprise instructions for identifying, isolating, enriching, and/or expanding a population of immunosuppressive regulatory T-cells by use of the kit's contents.

Yet other aspects of the present specification disclose a composition comprising a population of immunosuppressive regulatory T-cells obtained by a method of obtaining a population of immunosuppressive regulatory T-cells as disclosed herein. In an aspect, a population of immunosuppressive regulatory T-cells is obtained by a method comprising screening a sample comprising a population of T-cells to detect a level of cellular expression of a CD6 biomarker as disclosed herein and isolating a subpopulation of T-cells comprising a $CD6^{low/-}$ expression pattern, thereby obtaining the population of immunosuppressive regulatory T-cells. In another aspect, a population of immunosuppressive regulatory T-cells is obtained by a method comprising screening a sample comprising a population of T-cells to detect a level of cellular expression of the at least two different biomarkers, the at least two different biomarkers including a CD25 biomarker and a CD6 biomarker; and isolating a subpopulation of T-cells comprising a $CD25^+$ $CD6^{low/-}$ expression pattern, thereby obtaining the population of immunosuppressive regulatory T-cells. In yet another aspect, a population of immunosuppressive regulatory T-cells is obtained by a method comprising screening a sample comprising a population of T-cells to detect a level of cellular expression of at least three different biomarkers, the at least three different biomarkers including a CD4 biomarker, a CD25 biomarker, and a CD6 biomarker; and isolating a subpopulation of T-cells comprising a $CD4^+$ $CD25^+$ $CD6^{low/-}$ expression pattern, thereby obtaining the population of immunosuppressive regulatory T-cells.

In another aspect, a population of immunosuppressive regulatory T-cells is obtained by a method comprising contacting a sample comprising a population of T-cells with a CD6 biomarker ligand; screening the population of T-cells to detect a level of cellular expression of a CD6 biomarker; and isolating a subpopulation of T-cells comprising a $CD6^{low/-}$ expression pattern, thereby obtaining the population of immunosuppressive regulatory T-cells. In yet another aspect, a population of immunosuppressive regulatory T-cells is obtained by a method comprising contacting a sample comprising a population of T-cells with at least two different biomarker ligands, wherein the at least two different biomarker ligands include a CD25 biomarker ligand and a CD6 biomarker ligand; screening the population of T-cells to detect a level of cellular expression of at least two different biomarkers; wherein the at least two different biomarkers include a CD25 biomarker and a CD6 biomarker; and isolating a subpopulation of T-cells comprising a $CD25^+$ $CD6^{low/-}$ expression pattern, thereby obtaining the population of immunosuppressive regulatory T-cells. In still another aspect, a population of immunosuppressive regulatory T-cells is obtained by a method comprising contacting a sample comprising a population of T-cells with at least three different biomarker ligands, wherein the at least three different biomarker ligands include a CD4 biomarker ligand, a CD25 biomarker ligand, and a CD6 biomarker ligand; screening the population of T-cells to detect a level of cellular expression of at least three different biomarkers; wherein the at least three different biomarkers include a CD4 biomarker, a CD25 biomarker, and a CD6 biomarker; and isolating a subpopulation of T-cells comprising a $CD4^+$ $CD25^+$ $CD6^{low/-}$ expression pattern, thereby obtaining the population of immunosuppressive regulatory T-cells.

The identifying step, including the samples and useful biomarkers are as disclosed herein. The isolating step may use labeled biomarkers with flow cytometer, cell sorter, magnetic particles/bead, complement lysis, cell panning or other methodologies known to one of ordinary skill in the art for isolating cells. The identifying and isolating can proceed in any order or simultaneously by the use of multiple, distinguishable biomarkers used to detect the common determinants. The methods disclosed herein may further comprise enriching or expanding the identified population of immunosuppressive regulatory T-cells.

Still other aspects of the present specification disclose a use of a composition comprising a population of immunosuppressive regulatory T-cells as disclosed herein to treat an immune response. An immune response may be an autoimmune response.

Other aspects of the present specification disclose a method of enriching immunosuppressive regulatory T-cells in an individual, the method comprising administering an α-CD6 antibody to the individual, wherein the administration renders inoperable T-cells comprising a $CD6^{hi/+}$ expression pattern, but not T-cells comprising a $CD6^{low/-}$ expression pattern, thereby enriching for a population of immunosuppressive regulatory T-cells in the individual.

Other aspects of the present specification disclose a method of identifying four distinct maturation subsets of immunosuppressive regulatory T-cell populations, In an aspect, the method may comprises the step of screening a sample comprising a population of T-cells to detect a level of cellular expression of a CD4 biomarker, a CD25 biomarker, a CD6 biomarker, and one additional biomarker, the one additional biomarker being a FoxP3 biomarker, a CD45RA biomarker, a CCR4 biomarker, a CD39 biomarker, or a HLA-Dr biomarker; wherein detection of the four distinct maturation subsets of immunosuppressive regulatory T-cells is based upon a i) $CD4^+CD25^+CD6^{low/-}$ $CD45RA^+$ expression pattern in conjunction with a $CCR4^{low}$ expression pattern, a $CD39^{low}$ expression pattern, or a $HLA-Dr^{low}$ expression pattern; ii) a $CD4^+CD25^+CD6^{low/-}$ $CD45RA^+$ expression pattern in conjunction with a $CCR4^-$ expression pattern, a $CD39^-$ expression pattern, or a $HLA-Dr^-$ expression pattern; iii) a $CD4^+CD25^{hi/+}CD6^{low/-}$ expression pattern in conjunction with a $CCR4^{hi/+}$ expression pattern, a CD45RA$^-$ expression pattern, a CD39$^{hi/+}$ expression pattern, or a HLA-Dr$^{low/-}$ expression pattern; and iv) a CD4$^+$CD25$^+$CD6$^+$ expression pattern in conjunction with CR4$^{hi/+}$ expression pattern, a CD45RA$^-$ expression pattern, a CD39$^{low/-}$ expression pattern, or a HLA-Dr$^{low/-}$ expression pattern. In another aspect, the method may comprises the step of screening a sample comprising a population of T-cells to detect a level of cellular expression of a CD4 biomarker, a CD25 biomarker, a CD127 biomarker, and one additional biomarker, the one additional biomarker being a FoxP3 biomarker, a CD45RA biomarker, a CCR4 biomarker, a CD39 biomarker, or a HLA-Dr biomarker; wherein detection of the four distinct maturation subsets of immunosuppressive regulatory T-cells is based upon a i) CD4$^+$CD25$^+$CD127$^{low/-}$ CD45RA$^+$ expression pattern in conjunction with a CCR4$^{low}$ expression pattern, a CD39$^{low}$ expression pattern, or a HLA-Dr$^{low}$ expression pattern; ii) a CD4$^+$CD25$^+$CD127$^{low/-}$CD45RA$^+$ expression pattern in conjunction with a CCR4$^-$ expression pattern, a CD39$^-$ expression pattern, or a HLA-Dr$^-$ expression pattern; iii) a CD4$^+$CD25$^{hi/+}$CD127$^{low/-}$ expression pattern in conjunction with a CCR4$^{hi/+}$ expression pattern, a CD45RA$^-$ expression pattern, a CD39$^{hi/+}$ expression pattern, or a HLA-Dr$^{low/-}$ expression pattern; and iv) a CD4$^+$CD25$^+$CD127$^+$ expression pattern in conjunction with CR4$^{hi/+}$ expression pattern, a CD45RA$^-$ expression pattern, a CD39$^{low/-}$ expression pattern, or a HLA-Dr$^{low/-}$ expression pattern. The four distinct maturation subsets of immunosuppressive regulatory T-cell populations, include, without limitation, a nave or resting immunosuppressive regulatory T-cell population subset, an immature or memory immunosuppressive regulatory T-cell population subset, a mature or effector immunosuppressive regulatory T-cell population subset, and a terminal differentiated immunosuppressive regulatory T-cell population subset.

DETAILED DESCRIPTION

Figure 1:
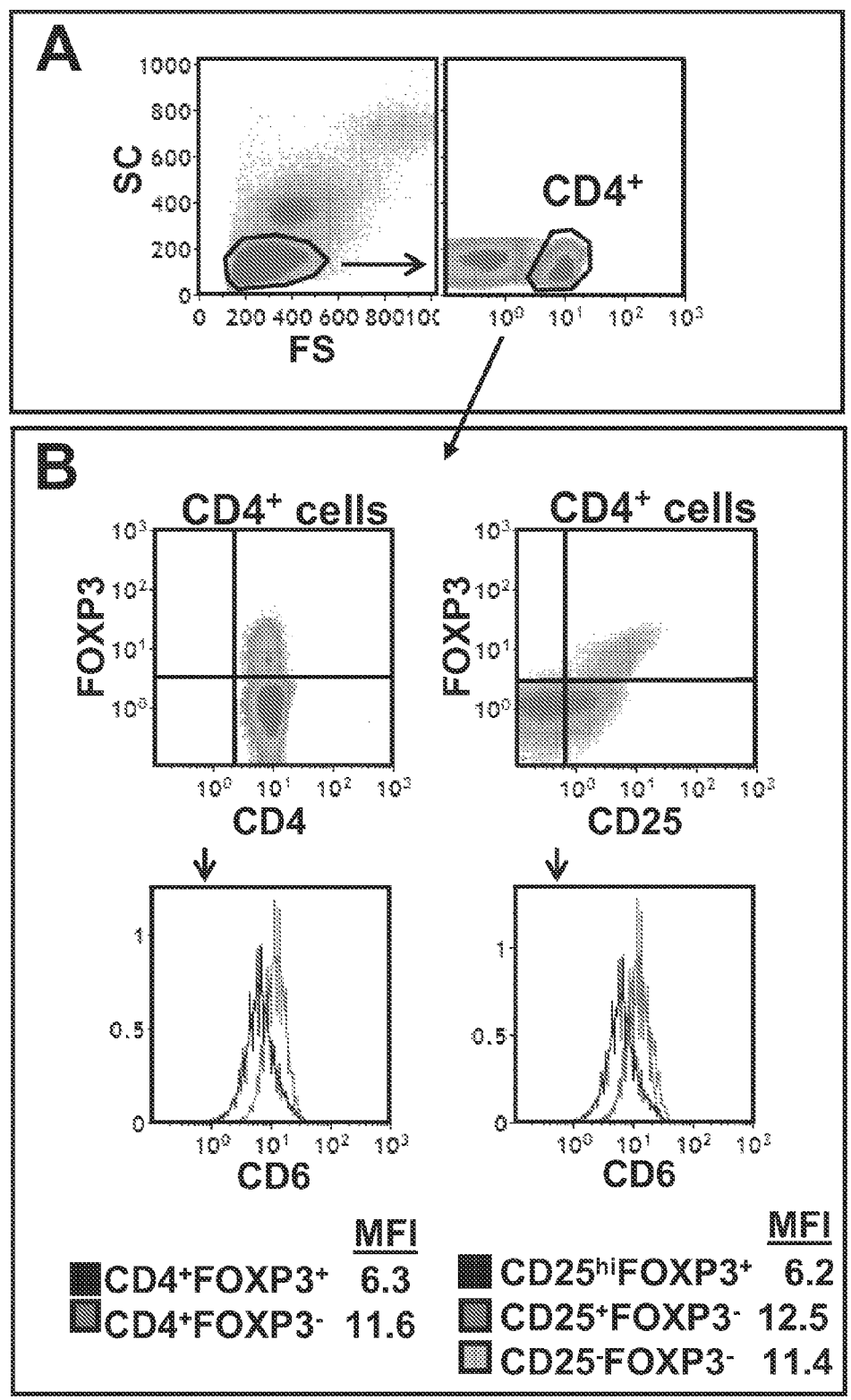
FIG. 1A shows dotplots analyzing CD4$^+$ lymphocytes for CD4/FOXP3 and CD25/FOXP3 expression.
FIG. 1B shows an overlay plot of low or negative expression of CD6 on CD4$^+$FOXP3$^+$ and CD25$^+$FOXP3$^+$ cell populations as compare with CD4$^+$FOXP3$^-$ and CD4$^+$CD25$^+$FOXP3$^-$ cell population respectively.

The present specification relates to the discovery that CD6 is a particularly useful biomarker in identifying immunosuppressive regulatory T-cells in a sample. The present specification discloses that detection of low or negative expression of CD6 in the surface membrane of human T-cells improves the definition of naturally-occurring regulatory T-cells. This $CD6^{low/-}$ detection allows the development of improved methods of identifying, isolating, enriching, and/or expanding a population of immunosuppressive regulatory T-cells. In addition, the ability to isolate, enrich and/or expand $CD6^{low/-}$ immunosuppressive regulatory T-cells enables the development of cell therapies useful in treating immuno-based disorders.

Aspects of the present specification disclose, in part, a method of identifying a population of immunosuppressive regulatory T-cells. In one embodiment, the method disclosed herein comprises screening a sample comprising a population of T-cells to detect a level of cellular expression of a CD6 biomarker, wherein detection of a subpopulation of T-cells comprising a $CD6^{low/-}$ expression pattern identifies the population of immunosuppressive regulatory T-cells in the sample.

In another embodiment, the method disclosed herein comprises contacting a sample comprising a population of T-cells with a CD6 biomarker ligand; and screening the population of T-cells to detect a level of cellular expression of a CD6 biomarker; wherein detection of a subpopulation of T-cells comprising a $CD6^{low/-}$ expression pattern identifies the population of immunosuppressive regulatory T-cells in the sample.

In yet another embodiment, the method disclosed herein comprises screening a sample comprising a population of T-cells to detect a level of cellular expression of at least two different biomarkers, the at least two different biomarkers including, a CD25 biomarker and a CD6 biomarker; wherein detection of a subpopulation of T-cells comprising a $CD25^+$ $CD6^{low/-}$ expression pattern identifies the population of immunosuppressive regulatory T-cells in the sample.

In yet another embodiment, the method disclosed herein comprises contacting a sample comprising a population of T-cells with at least two different biomarkers ligands, wherein the at least two different biomarker ligands include a CD25 biomarker ligand and a CD6 biomarker ligand; and screening the population of T-cells to detect a level of cellular expression of at least two different biomarkers; wherein the at least two different biomarkers include a CD25 biomarker and a CD6 biomarker; and wherein detection of a subpopulation of T-cells comprising a $CD25^+$ $CD6^{low/-}$ expression pattern identifies the population of immunosuppressive regulatory T-cells in the sample.

In still another embodiment, the method disclosed herein comprises screening a sample comprising a population of T-cells to detect a level of cellular expression of at least two different biomarkers, the at least two different biomarkers including, a CD6 biomarker and a CD127 biomarker; wherein detection of a subpopulation of T-cells comprising a $CD6^{low/-}$ $CD127^{low/-}$ expression pattern identifies the population of immunosuppressive regulatory T-cells in the sample.

In still another embodiment, the method disclosed herein comprises contacting a sample comprising a population of T-cells with at least two different biomarkers ligands, wherein the at least two different biomarker ligands include a CD6 biomarker ligand and a CD127 biomarker ligand; and screening the population of T-cells to detect a level of cellular expression of at least two different biomarkers; wherein the at least two different biomarkers include a CD6 biomarker and a CD127 biomarker; and wherein detection of a subpopulation of T-cells comprising a $CD6^{low/-}$ $CD127^{low/-}$ expression pattern identifies the population of immunosuppressive regulatory T-cells in the sample.

In another embodiment, the method disclosed herein comprises screening a sample comprising a population of T-cells to detect a level of cellular expression of at least three different biomarkers, the at least three different biomarkers including a CD4 biomarker, a CD25 biomarker, and a CD6 biomarker; wherein detection of a subpopulation of T-cells comprising a $CD4^+$ $CD25^+$ $CD6^{low/-}$ expression pattern identifies the population of immunosuppressive regulatory T-cells in the sample.

In another embodiment, the method disclosed herein comprises contacting a sample comprising a population of T-cells with at least three different biomarkers ligands, wherein the at least three different biomarker ligands include a CD4 biomarker ligand, a CD25 biomarker ligand, and a CD6 biomarker ligand; and screening the population of T-cells to detect a level of cellular expression of at least three different biomarkers; wherein the at least three different biomarkers include a CD4 biomarker, a CD25 biomarker, and a CD6 biomarker; and wherein detection of a subpopulation of T-cells comprising a $CD4^+$ $CD25^+$ $CD6^{low/-}$ expression pattern identifies the population of immunosuppressive regulatory T-cells in the sample.

In yet another embodiment, the method disclosed herein comprises screening a sample comprising a population of T-cells to detect a level of cellular expression of at least three different biomarkers, the at least three different biomarkers including a CD25 biomarker, a CD6 biomarker, and a CD127 biomarker; wherein detection of a subpopulation of T-cells comprising a $CD25^+$ $CD6^{low/-}$ $CD127^{low/-}$ expression pattern identifies the population of immunosuppressive regulatory T-cells in the sample.

In yet another embodiment, the method disclosed herein comprises contacting a sample comprising a population of T-cells with at least three different biomarkers ligands, wherein the at least three different biomarker ligands include a CD25 biomarker ligand, a CD6 biomarker ligand, and a CD127 biomarker ligand; and screening the population of T-cells to detect a level of cellular expression of at least three different biomarkers; wherein the at least three different biomarkers include a CD25 biomarker, a CD6 biomarker, and a CD127 biomarker; and wherein detection of a subpopulation of T-cells comprising a $CD25^+$ $CD6^{low/-}$ $CD127^{low/-}$ expression pattern identifies the population of immunosuppressive regulatory T-cells in the sample.

As used herein, the term "sample" or "biological sample" refers to tissues or body fluids removed from a mammal, preferably human, and which contain regulatory T cells. Samples may be blood and/or blood fractions, including peripheral blood sample like peripheral blood mononuclear cell (PBMC) sample or blood, bone marrow cell sample. A sample may also include any specific tissues/organ sample of interest, including, without limitation, lymphoid, thymus, pancreas, eye, heart, liver, nerves, intestine, skin, muscle, cartilage, ligament, synovial fluid, and/or joints. The samples may be taken from any individual including a healthy individual or an individual having cells, tissues, and/or an organ afflicted with the unwanted immune response. For example, a sample may be taken from an individual having an allergy, a graft vs. host disease, a cell or organ transplant, or an autoimmune disease or disorder. Methods for obtaining such samples are well known to a person of ordinary skill in the art of immunology and medicine. They include drawing and processing blood and blood components using routine procedures, or obtaining biopsies from the bone marrow or other tissue or organ using standard medical techniques.

As used herein, the term "biomarker" refers to an epitope, antigen or receptor that is expressed on lymphocytes or is differentially expressed on different subsets of lymphocytes. Expression of some biomarkers is specific for cells of a particular B cell or T cell lineage or maturational pathway, and the expression of others varies according to the state of activation, position, or differentiation of the same cells. A biomarker may be a cell surface biomarker or an intracellular biomarker. In one embodiment, the biomarkers used in the methods disclosed herein are all cell surface biomarkers. In another embodiment, the biomarkers used in the methods disclosed herein are all intracellular biomarkers. In yet another embodiment, the biomarkers used in the methods disclosed herein include both cell surface biomarkers and intracellular biomarkers. Exemplary biomarkers include, without limitation, a CD4 biomarker, a CD25 biomarker, a CD6 biomarker, a CD127 biomarker, a CD49d biomarker, a CD38 biomarker, a CD45RA biomarker, a HLA-DR biomarker, a FoxP3 biomarker, a CTLA-4 biomarker, a GITR biomarker, a LAG-3 biomarker, a CD39 biomarker, a Helios biomarker, a FcRL3 biomarker, a CCR7 biomarker, a CCR4 biomarker, a CCR8 biomarker, a CD62L biomarker, a ICOS biomarker, a CD103 biomarker, a PD-1 biomarker, a CD134 biomarker, a GARP biomarker, a CD45RB biomarker, a CD45RO biomarker, a CD95 biomarker, a CD122 biomarker, a CD147 biomarker and a CD8 biomarker. Other biomarkers useful to practice the disclosed methods and comprise the disclosed kits are known in the art.

In one embodiment, a method disclosed herein includes screening a sample comprising a population of T-cells to detect a level of cellular expression of a CD4 biomarker, a CD25 biomarker, a CD6 biomarker, a CD127 biomarker, a CD49d biomarker, a CD38 biomarker, a CD45RA biomarker, a HLA-DR biomarker, a FoxP3 biomarker, a CTLA-4 biomarker, a GITR biomarker, a LAG-3 biomarker, a CD39 biomarker, a Helios biomarker, a FcRL3 biomarker, a CCR7 biomarker, a CCR4 biomarker, a CCR8 biomarker, a CD62L biomarker, a ICOS biomarker, a CD103 biomarker, a PD-1 biomarker, a CD134 biomarker, a GARP biomarker, a CD45RB biomarker, a CD45RO biomarker, a CD95 biomarker, a CD122 biomarker, a CD8 biomarker, or any combination thereof. In an aspect of this embodiment, a method disclosed herein includes screening a sample comprising a population of T-cells to detect a level of cellular expression of a CD6 biomarker. In another aspect of this embodiment, a method disclosed herein includes screening a sample comprising a population of T-cells to detect a level of cellular expression of a CD25 biomarker and a CD6 biomarker. In another aspect of this embodiment, a method disclosed herein includes screening a sample comprising a population of T-cells to detect a level of cellular expression of a CD6 biomarker and a CD127 biomarker. In still another aspect of this embodiment, a method disclosed herein includes screening a sample comprising a population of T-cells to detect a level of cellular expression of a CD4 biomarker, a CD25 biomarker, and a CD6 biomarker. In another aspect of this embodiment, a method disclosed herein includes screening a sample comprising a population of T-cells to detect a level of cellular expression of a CD25 biomarker, a CD6 biomarker, and a CD127 biomarker. In yet another aspect of this embodiment, a method disclosed herein includes screening a sample comprising a population of T-cells to detect a level of cellular expression of a CD4 biomarker, a CD25 biomarker, a CD6 biomarker, and a CD127 biomarker.

In another embodiment, a method disclosed herein includes screening a sample comprising a population of T-cells to detect a level of cellular expression of at least two different biomarkers, the two different biomarkers including a CD4 biomarker, a CD25 biomarker, a CD6 biomarker, a CD127 biomarker, a CD49d biomarker, a CD38 biomarker, a CD45RA biomarker, a HLA-DR biomarker, a FoxP3 biomarker, a CTLA-4 biomarker, a GITR biomarker, a LAG-3 biomarker, a CD39 biomarker, a Helios biomarker, a FcRL3 biomarker, a CCR7 biomarker, a CCR4 biomarker, a CCR8 biomarker, a CD62L biomarker, a ICOS biomarker, a CD103 biomarker, a PD-1 biomarker, a CD134 biomarker, a GARP biomarker, a CD45RB biomarker, a CD45RO biomarker, a CD95 biomarker, a CD147 biomarker, a CD122 biomarker, a CD8 biomarker, or any combination thereof. In an aspect of this embodiment, a method disclosed herein includes screening a sample comprising a population of T-cells to detect a level of cellular expression of at least two different biomarkers, the two different biomarkers including a CD25 biomarker and a CD6 biomarker. In another aspect of this embodiment, a method disclosed herein includes screening a sample comprising a population of T-cells to detect a level of cellular expression of at least two different biomarkers, the two different biomarkers including a CD6 biomarker and a CD127 biomarker.

In another embodiment, a method disclosed herein includes screening a sample comprising a population of T-cells to detect a level of cellular expression of at least three different biomarkers, the three different biomarkers including a CD4 biomarker, a CD25 biomarker, a CD6 biomarker, a CD127 biomarker, a CD49d biomarker, a CD38 biomarker, a CD45RA biomarker, a HLA-DR biomarker, a FoxP3 biomarker, a CTLA-4 biomarker, a GITR biomarker, a LAG-3 biomarker, a CD39 biomarker, a Helios biomarker, a FcRL3 biomarker, a CCR7 biomarker, a CCR4 biomarker, a CCR8 biomarker, a CD62L biomarker, a ICOS biomarker, a CD103 biomarker, a PD-1 biomarker, a CD134 biomarker, a GARP biomarker, a CD45RB biomarker, a CD45RO biomarker, a CD95 biomarker, a CD122 biomarker, a CD147 biomarker, a CD8 biomarker, or any combination thereof. In an aspect of this embodiment, a method disclosed herein includes screening a sample comprising a population of T-cells to detect a level of cellular expression of at least three different biomarkers, the three different biomarkers including a CD4 biomarker, a CD25 biomarker, and a CD6 biomarker. In another aspect of this embodiment, a method disclosed herein includes screening a sample comprising a population of T-cells to detect a level of cellular expression of at least three different biomarkers, the three different biomarkers including a CD25 biomarker, a CD6 biomarker, and a CD127 biomarker.

In another embodiment, a method disclosed herein includes screening a sample comprising a population of T-cells to detect a level of cellular expression of at least two different biomarkers, the two different biomarkers including a CD25 biomarker and a CD6 biomarker, and one or more of the following additional biomarkers a CD4 biomarker, a CD127 biomarker, a CD49d biomarker, a CD38 biomarker, a CD45RA biomarker, a HLA-DR biomarker, a FoxP3 biomarker, a CTLA-4 biomarker, a GITR biomarker, a LAG-3 biomarker, a CD39 biomarker, a Helios biomarker, a FcRL3 biomarker, a CCR7 biomarker, a CCR4 biomarker, a CCR8 biomarker, a CD62L biomarker, a ICOS biomarker, a CD103 biomarker, a PD-1 biomarker, a CD134 biomarker, a GARP biomarker, a CD45RB biomarker, a CD45RO biomarker, a CD95 biomarker, a CD122 biomarker, a CD147 biomarker, a CD8 biomarker, or any combination thereof.

In another embodiment, a method disclosed herein includes screening a sample comprising a population of T-cells to detect a level of cellular expression of at least three different biomarkers, the three different biomarkers including a CD4 biomarker, a CD25 biomarker, and a CD6 biomarker, and one or more of the following additional biomarkers a CD127 biomarker, a CD49d biomarker, a CD38 biomarker, a CD45RA biomarker, a HLA-DR biomarker, a FoxP3 biomarker, a CTLA-4 biomarker, a GITR biomarker, a LAG-3 biomarker, a CD39 biomarker, a Helios biomarker, a FcRL3 biomarker, a CCR7 biomarker, a CCR4 biomarker, a CCR8 biomarker, a CD62L biomarker, a ICOS biomarker, a CD103 biomarker, a PD-1 biomarker, a CD134 biomarker, a GARP biomarker, a CD45RB biomarker, a CD45RO biomarker, a CD95 biomarker, a CD122 biomarker, a CD147 biomarker, a CD8 biomarker, or any combination thereof.

In another embodiment, a method disclosed herein includes screening a sample comprising a population of T-cells to detect a level of cellular expression of at least three different biomarkers, the three different biomarkers including a CD25 biomarker, a CD6 biomarker, and a CD127 biomarker, and one or more of the following additional biomarkers a CD4 biomarker, a CD49d biomarker, a CD38 biomarker, a CD45RA biomarker, a HLA-DR biomarker, a FoxP3 biomarker, a CTLA-4 biomarker, a GITR biomarker, a LAG-3 biomarker, a CD39 biomarker, a Helios biomarker, a FcRL3 biomarker, a CCR7 biomarker, a CCR4 biomarker, a CCR8 biomarker, a CD62L biomarker, a ICOS biomarker, a CD103 biomarker, a PD-1 biomarker, a CD134 biomarker, a GARP biomarker, a CD45RB biomarker, a CD45RO biomarker, a CD95 biomarker, a CD122 biomarker, a CD147 biomarker, a CD8 biomarker, or any combination thereof.

In another embodiment, a method disclosed herein includes screening a sample comprising a population of T-cells to detect a level of cellular expression of at least two different biomarkers, with the proviso that the at least two different biomarkers used to screen a sample do not include a FoxP3 biomarker, a CTLA-4 biomarker, or both a FoxP3 biomarker and a CTLA-4 biomarker. In an aspect of this embodiment, a method disclosed herein includes screening a sample comprising a population of T-cells to detect a level of cellular expression of at least two different biomarkers, the two different biomarkers including a CD25 biomarker and a CD6 biomarker, with the proviso that the at least two different biomarkers used to screen a sample do not include a FoxP3 biomarker, a CTLA-4 biomarker, or both a FoxP3 biomarker and a CTLA-4 biomarker. In another aspect of this embodiment, a method disclosed herein includes screening a sample comprising a population of T-cells to detect a level of cellular expression of at least two different biomarkers, the two different biomarkers including a CD6 biomarker and a CD127 biomarker, with the proviso that the at least two different biomarkers used to screen a sample do not include a FoxP3 biomarker, a CTLA-4 biomarker, or both a FoxP3 biomarker and a CTLA-4 biomarker. In yet another aspect of this embodiment, a method disclosed herein includes screening a sample comprising a population of T-cells to detect a level of cellular expression of at least two different biomarkers, the two different biomarkers including a CD25 biomarker and a CD127 biomarker, with the proviso that the at least two different biomarkers used to screen a sample do not include a FoxP3 biomarker, a CTLA-4 biomarker, or both a FoxP3 biomarker and a CTLA-4 biomarker. In still another aspect of this embodiment, a method disclosed herein includes screening a sample comprising a population of T-cells to detect a level of cellular expression of at least two different biomarkers, the two different biomarkers including a CD4 biomarker and a CD25 biomarker, with the proviso that the at least two different biomarkers used to screen a sample do not include a FoxP3 biomarker, a CTLA-4 biomarker, or both a FoxP3 biomarker and a CTLA-4 biomarker.

In another embodiment, a method disclosed herein includes screening a sample comprising a population of T-cells to detect a level of cellular expression of at least three different biomarkers, with the proviso that the at least three different biomarkers used to screen a sample do not include a FoxP3 biomarker, a CTLA-4 biomarker, or both a FoxP3 biomarker and a CTLA-4 biomarker. In an aspect of this embodiment, a method disclosed herein includes screening a sample comprising a population of T-cells to detect a level of cellular expression of at least three different biomarkers, the three different biomarkers including a CD4 biomarker, a CD25 biomarker, and a CD6 biomarker, with the proviso that the at least three different biomarkers used to screen a sample do not include a FoxP3 biomarker, a CTLA-4 biomarker, or both a FoxP3 biomarker and a CTLA-4 biomarker. In another aspect of this embodiment, a method disclosed herein includes screening a sample comprising a population of T-cells to detect a level of cellular expression of at least three different biomarkers, the three different biomarkers including a CD25 biomarker, a CD6 biomarker, and a CD127 biomarker, with the proviso that the at least three different biomarkers used to screen a sample do not include a FoxP3 biomarker, a CTLA-4 biomarker, or both a FoxP3 biomarker and a CTLA-4 biomarker. In yet another aspect of this embodiment, a method disclosed herein includes screening a sample comprising a population of T-cells to detect a level of cellular expression of at least three different biomarkers, the three different biomarkers including a CD4 biomarker, a CD25 biomarker, and a CD127 biomarker, with the proviso that the at least three different biomarkers used to screen a sample do not include a FoxP3 biomarker, a CTLA-4 biomarker, or both a FoxP3 biomarker and a CTLA-4 biomarker.

As used herein, the term "biomarker ligand" refers to a molecule that can specifically bind to an epitope, antigen or receptor that is expressed on lymphocytes or is differentially expressed on different subsets of lymphocytes. A biomarker ligand includes an antibody. As used herein, the term "antibody" refers to a molecule generated by an immune system that was made in response to a particular antigen that specifically binds to that antigen, and includes both naturally occurring antibodies and non-naturally occurring antibodies. For example, an antibody can be a polyclonal antibody, a monoclonal antibody, a dimer, a multimer, a multispecific antibody, a recombinant antibody, a humanized or primatized antibody, a chimeric antibody, bi-functional antibody, a cell-associated antibody like an Ig receptor, a linear antibody, a diabody, or a minibody, so long as the fragment exhibits the desired biological activity, and single chain derivatives of the same. An antibody can be a full-length immunoglobulin molecule comprising the VH and VL domains, as well as a light chain constant domain (CL) and heavy chain constant domains, CH1, CH2 and CH3, or an immunologically active fragment of a full-length immunoglobulin molecule, such as, e.g., a Fab fragment, a F(ab')2 fragment, a Fc fragment, a Fd fragment, a Fv fragment. An antibody can be derived from any vertebrate species (e.g., human, goat, horse, donkey, murine, rat, rabbit, or chicken), and can be of any type (e.g., IgG, IgE, IgM, IgD, and IgA), class (e.g., IgA, IgD, IgE, IgG, and IgM) or subclass (IgG1, IgG2, IgG3, IgG4, IgA1 and IgA2). For general disclosure on the structure of naturally occurring antibodies, non-naturally occurring antibodies, and antigenic compound-binding fragments thereof, see, e.g., Pluckthun in The Pharmacology of Monoclonal Antibodies, vol. 113, Rosenburg and Moore eds., Springer-Verlag, New York, pp. 269-315 (1994); Borrabeck, Antibody Engineering, 2d ed. (Oxford University Press 1995), each of which is hereby incorporated by reference in its entirety.

Exemplary biomarkers ligands include, an α-CD4 monoclonal antibody, an α-CD25 monoclonal antibody, an α-CD6 monoclonal antibody, an α-CD127 monoclonal antibody, an α-CD49d monoclonal antibody, an α-CD38 monoclonal antibody, an α-CD45RA monoclonal antibody, an α-HLA-DR monoclonal antibody, an α-FoxP3 monoclonal antibody, an α-CTLA-4 monoclonal antibody, an α-GITR monoclonal antibody, an α-LAG-3 monoclonal antibody, an α-CD39 monoclonal antibody, an α-Helios monoclonal antibody, an α-FcRL3 monoclonal antibody, an α-CCR7 monoclonal antibody, an α-CCR4 monoclonal antibody, an α-CCR8 monoclonal antibody, an α-CD62L monoclonal antibody, an α-ICOS monoclonal antibody, an α-CD103 monoclonal antibody, an α-PD-1 monoclonal antibody, an α-CD134 monoclonal antibody, an α-GARP monoclonal antibody, an α-CD45RB monoclonal antibody, an α-CD45RO monoclonal antibody, an α-CD95 monoclonal antibody, an α-CD122 monoclonal antibody, an α-CD147 monoclonal antibody and an α-CD8 monoclonal antibody. Such monoclonal antibodies are commercially available and known to one of ordinary skill in the art. See, e.g., BD Biosciences (San Jose, Calif.), eBiosciences (San Diego, Calif.).

In another embodiment, a CD6 biomarker ligand is a CD166 (ALCAM) ligand or any CD6 co-stimulatory signal.

A biomarker ligand may be labeled or unlabeled. If labeled, the biomarker may be covalently or noncovalently attached with a fluorophore, a quantum dot, a phosphore, a chemiluminescent compound, a bioluminescent compound, a chromogenic compound, an isotope compound like a lanthanide, a radioisotope, a biotin or avidin molecule, or any other label useful for detecting a cell bound by the biomarker. Methods of attaching labels to antibodies are well known to those of ordinary skill in the art. Particularly preferred labels are those which are attached to the biomarker ligand by a linker which can be readily cleaved or separated or subject to hydrolysis by contact with a predetermined enzyme under physiological conditions. A biomarker ligand may be labeled before or after contact with the sample or before or after contact with the biomarker. A biomarker ligand may also be labeled by contacting with a labeled antibody which binds to the biomarker ligand. A biomarker ligand may also be conjugated with a magnetic particle, such as a paramagnetic nanoparticles (Miltenyi Biotec, Germany).

A sample comprising a population of T cells as disclosed herein is contacted with a biomarker ligand. Contacting a sample with a biomarker ligand is done in such a way as to promote specific binding of the biomarker ligand to its cognate biomarker. Typically this is done under physiological conditions. For example, when a biomarker ligand is an antibody, contacting an antibody with a sample is done under conditions that result in the binding of the antibody to its corresponding biomarker, thereby resulting in an antibody/biomarker complex.

A sample comprising a population of T cells as disclosed herein is screened to detect a level of cellular expression of the biomarkers. A labeled biomarker may be screened using a detection method based on fluorescence, bioluminescence, chemiluminescence, spectroscopic, photochemical, biochemical, immunochemical, chemical, magnetic, or other physical means known to one of ordinary skill in the art. An unlabeled biomarker may be screened using a detection method based on size, volume, density, opacity, or other physical means known to one of ordinary skill in the art.

In an embodiment, screening a sample comprising a population of T-cells to detect a level of cellular expression a biomarker is accomplished using a cell sorter. Cell sorters are well known to persons of ordinary skill in the art and generally are capable of separating a complex mixture of cells into fractions of a single cell type. Typically, the cells to be sorted are introduced as a thin jet of carrier liquid emanating from a small nozzle orifice. Shortly after leaving the nozzle, the hydrodynamically-focused stream of fluid passes through the waist of one or more tightly focused beams of light, usually laser light. A number of detectors are aimed at the point where the stream passes through the light beam: one in line with the light beam (Forward Scatter or FSC) and several perpendicular to it (Side Scatter or SSC) and one or more fluorescent detectors. Each suspended particle from 0.2 μm to 150 μm passing through the beam scatters the ray, and fluorescent chemicals found in the particle or attached to the particle may be excited into emitting light at a longer wavelength than the light source. This combination of scattered and fluorescent light is picked up by the detectors, and, by analyzing fluctuations in brightness at each detector (one for each fluorescent emission peak), it is then possible to derive various types of information about the physical and chemical structure of each individual particle. The data generated by flow cytometers can be plotted in a single dimension, to produce a histogram, or in two-dimensional dot plots or even in three dimensions. The regions on these plots can be sequentially separated, based on fluorescence intensity, by creating a series of subset extractions, termed "gates." Some flow cytometers on the market have eliminated the need for fluorescence and use only light scatter for measurement. Other flow cytometers form images of each cell's fluorescence, scattered light, and transmitted light.

In an aspect of this embodiment, screening a sample comprising a population of T-cells to detect a level of cellular expression a biomarker is accomplished by flow cytometer using a fluorescently-labeled biomarker ligand. Flow cytometric sorting is a specialized type of flow cytometry. It provides a method for sorting a heterogeneous mixture of biological cells into two or more containers, one cell at a time, based upon the specific light scattering and fluorescent characteristics of each cell. It is a useful scientific instrument, as it provides fast, objective and quantitative recording of fluorescent signals from individual cells as well as physical separation of cells of particular interest. A flow cytometric sorter can easily analyze cells at speeds greater than 200,000 events per second. Generally, the physics of the carrier fluid, however, and the statistics of distributing the cells among the droplets limits sort rates to about 50,000 cells per second. This combination of speed and reliable separation allows individual cells to be isolated or enriched for other uses.

In another embodiment, screening a sample comprising a population of T-cells to detect a level of cellular expression a biomarker is accomplished by magnetic-activated cell sorting (MACS) using a magnetically labeled biomarker ligand. MACS allows cells to be separated by incubating with magnetic nanoparticles coated with a biomarker ligand for a particular biomarker. Magnetic nanoparticles may comprise super-paramagnetic nanoparticles composed of iron oxide and a polysaccharide coat. The magnetic nanoparticles are preferably small enough to remain in colloidal suspension, which permits rapid, efficient binding to cell surface biomarker. In aspects of this embodiment, the magnetic nanoparticles are between about 1 nm in diameter to about 100 nm in diameter, such as, e.g., about 25 nm in diameter, 50 nm in diameter, 75 nm in diameter, or 100 nm in diameter. In other aspects of this embodiment, the magnetic nanoparticles have a volume of, e.g., about one-millionth that of a typical mammalian cell, about five-millionth that of a typical mammalian cell, or about ten-millionth that of a typical mammalian cell. The magnetic nanoparticles preferably do not interfere with flow cytometry, are biodegradable, and have negligible effects on cellular functions. The antibody coupling to the magnetic nanoparticles may be direct or indirect, via a second antibody to a ligand such as a fluorophore, a quantum dot, a phosphore, a chemiluminescent compound, a bioluminescent compound, a chromogenic compound, an isotope compound like a lanthanide, a radioisotope, an enzyme, a biotin or avidin molecule, or any other label useful for detecting a cell bound by the biomarker.

In another embodiment, screening a sample comprising a population of T-cells to detect a level of cellular expression a biomarker is accomplished by solid-phase attachment. In an aspect, screening a sample comprising a population of T-cells to detect a level of cellular expression a biomarker is accomplished by panning or solid-phase affinity chromatography using a biomarker ligand as disclosed herein. In an aspect, screening a sample comprising a population of T-cells to detect a level of cellular expression a biomarker is accomplished by solid-phase magnetic beads using a magnetically labeled biomarker ligand as disclosed herein. See, e.g., US Patent Application Publication 2005/0186207, which is incorporated by reference in its entirety.

In another embodiment, screening a sample comprising a population of T-cells to detect a level of cellular expression a biomarker is accomplished by complement cell lysis. Complement cell lysis is used to eliminate undesired cell population recognized by antibodies, and is based in the function of certain type of antibodies to fix and activate a cascade of enzymatic molecules called "Complement system" on cell surface. Final reaction result in opening a physical hole in the membrane and produce cell lysis by osmosis. Typically, cells are incubated during 30 minutes at 4° C. with an antibody and a source of complement enzymes is added and incubated at 37° C. Finally, cells are washed with isotonic buffers and ready to be used.

A population of immunosuppressive regulatory T-cells is identified based on a characteristic expression pattern of one or more biomarkers. Generally, such cells are identified according to the expression levels biomarker or biomarkers based upon readily discernible differences in staining intensity as is known to one of ordinary skill in the art. Typically, the expression of a biomarker is classified as high (biomarker$^{hi}$), +(biomarker$^+$), low (biomarker$^{low}$) and −(biomarker$^−$).

Cells staining intensely or brightly when screened using a biomarker ligand is referred to as biomarker$^+$, and is indicative of a cell exhibiting a high level of biomarker expression. For example, CD4$^{hi/+}$, CD25$^{hi/+}$, CD6$^{hi/+}$, CD127$^{hi/+}$, CD49d$^{hi/+}$, CD38$^{hi/+}$, CD45RA$^{hi/+}$, HLA-DR$^{hi/+}$, FoxP3$^{hi/+}$, CTLA-4$^{hi/+}$, GITR$^{hi/+}$, LAG-3$^{hi/+}$, CD39$^{hi/+}$, FcRL3$^{hi/+}$, CCR7$^{hi/+}$, CCR4$^{hi/+}$, CCR8$^{hi/+}$, CD62L$^{hi/+}$, ICOS$^{hi/+}$, CD103$^{hi/+}$, PD-1$^{hi/+}$, CD134$^{hi/+}$, GARP$^{hi/+}$, CD45RB$^{hi/+}$, CD45RO$^{hi/+}$, CD95$^{hi/+}$, CD122$^{hi/+}$, CD147$^{hi/+}$ and CD8$^{hi/+}$ refers to cells which stain intensely or brightly when screened using a labeled biomarker ligand directed toward a CD4 biomarker, a CD25 biomarker, a CD6 biomarker, a CD127 biomarker, a CD49d biomarker, a CD38 biomarker, a CD45RA biomarker, a HLA-DR biomarker, a FoxP3 biomarker, a CTLA-4 biomarker, a GITR biomarker, a LAG-3 biomarker, a CD39 biomarker, a Helios biomarker, a FcRL3 biomarker, a CCR7 biomarker, a CCR4 biomarker, a CCR8, a CD62L biomarker, a ICOS biomarker, a CD103 biomarker, a PD-1 biomarker, a CD134 biomarker, a GARP biomarker, a CD45RB biomarker, a CD45RO biomarker, a CD95 biomarker, a CD122 biomarker, a CD147 biomarker, a CD8 biomarker, respectively.

Cells staining slightly, dully, or not at all when screened using a biomarker ligand is referred to as biomarker$^{low/−}$, and is indicative of a cell exhibiting a low level of biomarker expression. For example, CD4$^{low/−}$, CD25$^{low/−}$, CD6$^{low/−}$, CD127$^{low/−+}$, CD49d$^{low/−}$, CD38$^{low/−}$, CD45RA$^{low/−}$, HLA-DR$^{low/−}$, FoxP$^{low/−}$, CTLA-4$^{low/−}$, GITR$^{low/−}$, LAG-3$^{low/−}$, CD39$^{low/−}$, Helios$^{low/−}$, FcRL3$^{low/−}$, CCR7$^{low/−}$, CCR4$^{low/−}$, CCR8$^{low/−}$, CD62L$^{low/−}$, ICOS$^{low/−}$, CD103$^{low/−}$, PD-1$^{low/−}$, CD134$^{low/−}$, GARP$^{low/−}$, CD45RB$^{low/−}$, CD45RO$^{low/−}$, CD95$^{low/−}$, CD122$^{low/−}$, CD147$^{low/−}$ and CD8$^{low/−}$ refers to cells which stain slightly, dully, or not at all when screened using a labeled biomarker ligand directed toward a CD4 biomarker, a CD25 biomarker, a CD6 biomarker, a CD127 biomarker, a CD49d biomarker, a CD38 biomarker, a CD45RA biomarker, a HLA-DR biomarker, a FoxP3 biomarker, a CTLA-4 biomarker, a GITR biomarker, a LAG-3 biomarker, a CD39 biomarker, a Helios biomarker, a FcRL3 biomarker, a CCR7 biomarker, a CCR4 biomarker, a CCR8, a CD62L biomarker, a ICOS biomarker, a CD103 biomarker, a PD-1 biomarker, a CD134 biomarker, a GARP biomarker, a CD45RB biomarker, a CD45RO biomarker, a CD95 biomarker, a CD122 biomarker, a CD147 biomarker, a CD8 biomarker, respectively.

The cut off for designating a cell as a biomarker$^{hi}$ cell can be set in terms of the fluorescent intensity distribution observed for all cells with those cells in the top 2%, 3%, 5%, 7% or 10% of fluorescence intensity being designated as biomarker$^{hi}$ cells. In aspects of this embodiment, CD4$^{hi}$ cells, CD25$^{hi}$ cells, CD6$^{hi}$ cells, CD127$^{hi}$ cells, CD49d$^{hi}$ cells, CD38$^{hi}$ cells, CD45RA$^{hi}$ cells, HLA-DR$^{hi}$ cells, FoxP3$^{hi}$ cells, CTLA-4$^{hi}$ cells, GITR$^{hi}$ cells, LAG-3$^{hi}$ cells, CD39$^{hi}$ cells, Helios$^{hi}$ cells, FcRL3$^{hi}$ cells, CCR7$^{hi+}$ cells, CCR4$^{hi}$ cells, CCR8$^{hi}$ cells, CD62L cells, ICOS$^{hi}$ cells, CD103$^{hi}$ cells, PD-1$^{hi}$ cells, CD134$^{hi}$ cells, GARP$^{hi}$ cells, CD45RB$^{hi}$ cells, CD45RO$^{hi}$ cells, CD95$^{hi}$ cells, CD122$^{hi}$ cells, CD147$^{hi}$ cells, and/or CD8$^{hi}$ cells exhibit 90% or more, 93% or more, 95% or more, 97% or more, or 98% or more fluorescence intensity as compared to the fluorescence intensity observed for all cells being screened.

The cut off for designating a cell as a biomarker$^+$ cell can be set in terms of the fluorescent intensity distribution observed for all cells with those cells in the top 10%, 20%, 30%, 40% or 50% of fluorescence intensity being designated as biomarker$^+$ cells. In aspects of this embodiment, CD4$^+$ cells, CD25$^+$ cells, CD6$^+$ cells, CD127$^+$ cells, CD49d$^+$ cells, CD38$^+$ cells, CD45RA$^+$ cells, HLA-DR$^+$ cells, FoxP3$^+$ cells, CTLA-4$^+$ cells, GITR' cells, LAG-3$^+$ cells, CD39$^+$ cells, Helios$^+$ cells, FcRL3$^+$ cells, CCR7$^+$ cells, CCR4$^+$ cells, CCR8+ cells, CD62L+ cells, ICOS+ cells, CD103+ cells, PD-1+ cells, CD134+ cells, GARP+ cells, CD45RB+ cells, CD45RO+ cells, CD95+ cells, CD122+ cells, CD147+ cells, and/or CD8+ cells exhibit 10% or more, 20% or more, 30% or more, 40% or more, or 50% or more fluorescence intensity as compared to the fluorescence intensity observed for all cells being screened.

The cut off for designating a cell as a biomarker$^{low/-}$ cell can be set in terms of the fluorescent intensity distribution observed for all cells with those cells falling below 50%, 40%, 30%, 20%, or 10% fluorescence intensity being designated as biomarker$^{low/-}$ cells. In aspects of this embodiment, CD4$^{low}$ cells, CD25$^{low}$ cells, CD6$^{low}$ cells, CD127$^{low}$ cells, CD49d$^{low}$ cells, CD38$^{low}$ cells, CD45RA$^{low}$ cells, HLA-DR$^{low}$ cells, FoxP3$^{low}$ cells, CTLA-4$^{low}$ cells, GITR$^{low}$ cells, LAG-3$^{low}$ cells, CD39$^{low}$ cells, Helios$^{low}$ cells, FcRL3$^{low}$ cells, CCR7$^{low}$ cells, CCR4$^{low}$ cells, CCR8$^{low}$ cells, CD62L$^{low}$ cells, ICOS$^{low}$ cells, CD103$^{low}$ cells, PD-1$^{low}$ cells, CD134$^{low}$ cells, GARP$^{low}$ cells, CD45RBP$^{low}$ cells, CD45ROP$^{low}$ cells, CD95P$^{low}$ cells, CD122$^{low}$ cells, CD147$^{low}$ cells, and/or CD8$^{low}$ cells exhibit 50% or less, 40% or less, 30% or less, 20% or less, or 10% or less fluorescence intensity as compared to the fluorescence intensity observed for all cells being screened.

The cut off for designating a cell as a biomarker$^-$ cell can be set in terms of the fluorescent intensity distribution observed for all cells with those cells falling below 10%, 7%, 5%, 3%, or 2% fluorescence intensity being designated as biomarker$^-$ cells. In aspects of this embodiment, CD4$^-$ cells, CD25$^-$ cells, CD6$^-$ cells, CD127$^-$ cells, CD49d$^-$ cells, CD38$^-$ cells, CD45RA$^-$ cells, HLA-DR$^-$ cells, FoxP3$^-$ cells, CTLA-4$^-$ cells, GITR$^-$ cells, LAG-3$^-$ cells, CD39$^-$ cells, Helios$^-$ cells, FcRL3$^-$ cells, CCR7$^-$ cells, CCR4$^-$ cells, CCR8$^-$ cells, CD62L$^-$ cells, ICOS$^-$ cells, CD103$^-$ cells, PD-1$^-$ cells, CD134$^-$ cells, GARP$^-$ cells, CD45RB$^-$ cells, CD45RO$^-$ cells, CD95$^-$ cells, CD122$^-$ cells, CD147$^-$ cells, and/or CD8$^-$ cells exhibit 10% or less, 7% or less, 5% or less, 3% or less, or 2% or less fluorescence intensity as compared to the fluorescence intensity observed for all cells being screened.

Cells may also be distinguished by obtaining the frequency distribution of biomarker staining for all cells and generating a population curve fit to a higher staining population and a lower staining population. Individual cells are then assigned to the population to which they are likely to belong based upon a statistical analysis of the respective population distributions. In one embodiment, biomarker$^{low/-}$ cells exhibit one-fold or less, two-fold or less, or three-fold less fluorescence intensely than biomarker$^+$ cells. In aspects of this embodiment, CD4$^{low/-}$ cells, CD25$^{low/-}$ cells, CD6$^{low/-}$ cells, CD127$^{low/-+}$ cells, CD49d$^{low/-}$ cells, CD38$^{low/-}$ cells, CD45RA$^{low/-}$ HLA-DR$^{low/-}$ cells, FoxP3$^{low/-}$ cells, CTLA-4$^{low/-}$ cells, GITR$^{low/-}$ cells, LAG-3$^{low/-}$ cells, CD39$^{low/-}$ cells, Helios$^{low/-}$ cells, FcRL3$^{low/-}$ cells, CCR7$^{low/-}$ cells, CCR4$^{low/-}$ cells, CCR8$^{low/-}$ cells, CD62L$^{low/-}$ cells, ICOS$^{low/-}$ cells, CD103$^{low/-}$ cells, PD-1$^{low/-}$ cells, CD134$^{low/-}$ cells, GARP$^{low/-}$ cells, CD45RB$^{low/-}$ cells, CD45RO$^{low/-}$ cells, CD95$^{low/-}$ cells, CD122$^{low/-}$ cells, CD147$^{low/-}$ cells, and CD8$^{low/-}$ cells exhibit one-fold or less, two-fold or less, or three-fold less fluorescence intensely than CD4+ cells, CD25+ cells, CD6+ cells, CD127+ cells, CD49d+ cells, CD38+ cells, CD45RA+ cells, HLA-DR+ cells, FoxP3+ cells, CTLA-4+ cells, GITR+ cells, LAG-3+ cells, CD39+ cells, Helios+ cells, FcRL3+ cells, CCR7+ cells, CCR4+ cells, CCR8+ cells, CD62L+ cells, ICOS+ cells, CD103+ cells, PD-1+ cells, CD134+ cells, GARP+ cells, CD45RB+ cells, CD45RO+ cells, CD95+ cells, CD122+ cells, CD147+ cells, and CD8+ cells, respectively.

In one embodiment, a population of immunosuppressive regulatory T-cells is identified based upon T-cells comprising a CD6$^{low/-}$ expression pattern. In an aspect of this embodiment, a population of immunosuppressive regulatory T-cells is identified based upon T-cells comprising a CD25+ CD6$^{low/-}$ expression pattern. In yet another aspect of this embodiment, a population of immunosuppressive regulatory T-cells is identified based upon T-cells comprising a CD6$^{low/-}$ CD127$^{low/-}$ expression pattern. In still another aspect of this embodiment, a population of immunosuppressive regulatory T-cells is identified based upon T-cells comprising a CD6$^{low/-}$ CD38$^{low/-}$ expression pattern. In still another aspect of this embodiment, a population of immunosuppressive regulatory T-cells is identified based upon T-cells comprising a CD6$^{low/-}$ CD49$^{low/-}$ expression pattern.

In another aspect of this embodiment, a population of immunosuppressive regulatory T-cells is identified based upon T-cells comprising a CD4+ CD25+ CD6$^{low/-}$ expression pattern. In yet another aspect of this embodiment, a population of immunosuppressive regulatory T-cells is identified based upon T-cells comprising a CD25+ CD6$^{low/-}$ CD127$^{low/-}$ expression pattern. In still another aspect of this embodiment, a population of immunosuppressive regulatory T-cells is identified based upon T-cells comprising a CD6$^{low/-}$ CD127$^{low/-}$ CD49d$^{low/-}$ expression pattern. In still another aspect of this embodiment, a population of immunosuppressive regulatory T-cells is identified based upon T-cells comprising a CD6$^{low/-}$ CD127$^{low/-}$ CD38$^{low/-}$ expression pattern.

In other aspects of this embodiment, a population of immunosuppressive regulatory T-cells is identified based upon T-cells comprising a CD4+ CD25+ CD6$^{low/-}$ CD127$^{low/-}$ expression pattern, a CD4+ CD25+ CD6$^{low/-}$ CD49d$^{low/-}$ expression pattern, a CD4+ CD25+ CD6$^{low/-}$ CD38$^{low/-}$ expression pattern, a CD4+ CD25+ CD6$^{low/-}$ CD45RA$^{low/-}$ expression pattern, a CD25+ CD6$^{low/-}$ CD127$^{low/-}$ CD49d$^{low/-}$ expression pattern, a CD25+ CD6$^{low/-}$ CD127$^{low/-}$ CD38$^{low/-}$ expression pattern, or a CD6$^{low/-}$ CD127$^{low/-}$ CD49d$^{low/-}$ CD38$^{low/-}$ expression pattern.

In other aspects of this embodiment, a population of immunosuppressive regulatory T-cells is identified based upon T-cells comprising a CD4+ CD25+ CD6$^{low/-}$ HLA-Dr+ expression pattern, a CD4+ CD25+ CD6$^{low/-}$ HLA-Dr$^{low/-}$ expression pattern, a CD4+ CD25+ CD6$^{low/-}$ FoxP3+ expression pattern, a CD4+ CD25+ CD6$^{low/-}$ FoxP3$^{low/-}$ expression pattern, a CD4+ CD25+ CD6$^{low/-}$ CTLA-4+ expression pattern, a CD4+ CD25+ CD6$^{low/-}$ CTLA-4$^{low/-}$ expression pattern, a CD4+ CD25+ CD6$^{low/-}$ GITR+ expression pattern, a CD4+ CD25+ CD6$^{low/-}$ GITR$^{low/-}$ expression pattern, a CD4+ CD25+ CD6$^{low/-}$ LAG-3+ expression pattern, a CD4+ CD25+ CD6$^{low/-}$ LAG-3$^{low/-}$ expression pattern, a CD4+ CD25+ CD6$^{low/-}$ CD39+ expression pattern, a CD4+ CD25+ CD6$^{low/-}$ CD39$^{low/-}$ expression pattern, a CD4+ CD25+ CD6$^{low/-}$ Helios+ expression pattern, a CD4+ CD25+ CD6$^{low/-}$ Helios$^{low/-}$ expression pattern, a CD4+ CD25+ CD6$^{low/-}$ FcRL3+ expression pattern, a CD4+ CD25+ CD6$^{low/-}$ FcRL3$^{low/-}$ expression pattern, a CD4+ CD25+ CD6$^{low/-}$ CCR7+ expression pattern, a CD4+ CD25+ CD6$^{low/-}$ CCR7$^{low/-}$ expression pattern, a CD4+ CD25+ CD6$^{low/-}$ CCR4+ expression pattern, a CD4+ CD25+ CD6$^{low/-}$ CCR4$^{low/-}$ expression pattern, a CD4+ CD25+ CD6$^{low/-}$ CCR8+ expression pattern, a CD4+ CD25+ CD6$^{low/-}$ CCR8$^{low/-}$ expression pattern, a CD4+ CD25+ CD6$^{low/-}$ CD62L+ expression pattern, a CD4+ CD25+

CD6$^{low/-}$ CD62L$^{low/-}$ expression pattern, a CD4$^+$ CD25$^+$ CD6$^{low/-}$ ICOS$^+$ expression pattern, a CD4$^+$ CD25$^+$ CD6$^{low/-}$ ICOS$^{low/-}$ expression pattern, a CD4$^+$ CD25$^+$ CD6$^{low/-}$ CD103$^+$ expression pattern, a CD4$^+$ CD25$^+$ CD6$^{low/-}$ CD103$^{low/-}$ expression pattern, a CD4$^+$ CD25$^+$ CD6$^{low/-}$ PD-1$^+$ expression pattern, a CD4$^+$ CD25$^+$ CD6$^{low/-}$ PD-1$^{low/-}$ expression pattern, a CD4$^+$ CD25$^+$ CD6$^{low/-}$ CD134$^+$ expression pattern, a CD4$^+$ CD25$^+$ CD6$^{low/-}$ CD134$^{low/-}$ expression pattern, a CD4$^+$ CD25$^+$ CD6$^{low/-}$ GARP$^+$ expression pattern, a CD4$^+$ CD25$^+$ CD6$^{low/-}$ GARP$^{low/-}$ expression pattern, a CD4$^+$ CD25$^+$ CD6$^{low/-}$ CD45RB$^+$ expression pattern, a CD4$^+$ CD25$^+$ CD6$^{low/-}$ CD45RB$^{low/-}$ expression pattern, a CD4$^+$ CD25$^+$ CD6$^{low/-}$ CD45RO$^+$ expression pattern, a CD4$^+$ CD25$^+$ CD6$^{low/-}$ CD45RO$^{low/-}$ expression pattern, a CD4$^+$ CD25$^+$ CD6$^{low/-}$ CD95$^+$ expression pattern, a CD4$^+$ CD25$^+$ CD6$^{low/-}$ CD95$^{low/-}$ expression pattern, a CD4$^+$ CD25$^+$ CD6$^{low/-}$ CD122$^+$ expression pattern, a CD4$^+$ CD25$^+$ CD6$^{low/-}$ CD122$^{low/-}$ expression pattern, a CD4$^+$ CD25$^+$ CD6$^{low/-}$ CD147$^{low/-}$ expression pattern a CD4$^+$ CD25$^+$ CD6$^{low/-}$ CD8$^+$ expression pattern, or a CD4$^+$ CD25$^+$ CD6$^{low/-}$ CD8$^{low/-}$ expression pattern.

In another embodiment, a population of immunosuppressive regulatory T-cells is identified based upon T-cells comprising a CD6$^{low/-}$ and one or more of the following additional biomarker expression patterns a CD4$^+$ expression pattern, a CD25$^+$ expression pattern, a CD127$^{low/-}$ expression pattern, a CD49d$^{low/-}$ expression pattern, a CD38$^{low/-}$ expression pattern, a CD45RA$^{low/-}$ expression pattern, a HLA-Dr$^+$ expression pattern, a HLA-Dr$^{low/-}$ expression pattern, a FoxP3$^+$ expression pattern, a FoxP3$^{low/-}$ expression pattern, a CTLA-4$^+$ expression pattern, a CTLA-4$^{low/-}$ expression pattern, a GITR$^+$ expression pattern, a GITR$^{low/-}$ expression pattern, a LAG-3$^+$ expression pattern, a LAG-3$^{low/-}$ expression pattern, a CD39$^+$ expression pattern, a CD39$^{low/-}$ expression pattern, a Helios$^+$ expression pattern, a Helios$^{low/-}$ expression pattern, a FcRL3$^+$ expression pattern, a FcRL3$^{low/-}$ expression pattern, a CCR7$^+$ expression pattern, a CCR7$^{low/-}$ expression pattern, a CCR4$^+$ expression pattern, a CCR4$^{low/-}$ expression pattern, a CCR8$^+$ expression pattern, a CCR8$^{low/-}$ expression pattern, a CD62L$^+$ expression pattern, a CD62L$^{low/-}$ expression pattern, a ICOS$^+$ expression pattern, a ICOS$^{low/-}$ expression pattern, a CD103$^+$ expression pattern, a CD103$^{low/-}$ expression pattern, a PD-1$^+$ expression pattern, a PD-1$^{low/-}$ expression pattern, a CD134$^+$ expression pattern, a CD134$^{low/-}$ expression pattern, a GARP$^+$ expression pattern, a GARP$^{low/-}$ expression pattern, a CD45RB$^+$ expression pattern, a CD45RB$^{low/-}$ expression pattern, a CD45RO$^+$ expression pattern, a CD45RO$^{low/-}$ expression pattern, a CD95$^+$ expression pattern, a CD95$^{low/-}$ expression pattern, a CD122$^+$ expression pattern, a CD122$^{low/-}$ expression pattern, a CD147$^+$ expression pattern, a CD147$^{low/-}$ expression pattern, a CD8$^+$ expression pattern, or a CD8$^{low/-}$ expression pattern.

In yet another embodiment, a population of immunosuppressive regulatory T-cells is identified based upon T-cells comprising a CD25$^+$ CD6$^{low/-}$ and one or more of the following additional biomarker expression patterns a CD4$^+$ expression pattern, a CD127$^{low/-}$ expression pattern, a CD49d$^{low/-}$ expression pattern, a CD38$^{low/-}$ expression pattern, a CD45RA$^{low/-}$ expression pattern, a HLA-Dr$^+$ expression pattern, a HLA-Dr$^{low/-}$ expression pattern, a FoxP3$^+$ expression pattern, a FoxP3$^{low/-}$ expression pattern, a CTLA-4$^+$ expression pattern, a CTLA-4$^{low/-}$ expression pattern, a GITR$^+$ expression pattern, a GITR$^{low/-}$ expression pattern, a LAG-3$^+$ expression pattern, a LAG-3$^{low/-}$ expression pattern, a CD39$^+$ expression pattern, a CD39$^{low/-}$ expression pattern, a Helios$^+$ expression pattern, a Helios$^{low/-}$ expression pattern, a FcRL3$^+$ expression pattern, a FcRL3$^{low/-}$ expression pattern, a CCR7$^+$ expression pattern, a CCR7$^{low/-}$ expression pattern, a CCR4$^+$ expression pattern, a CCR4$^{low/-}$ expression pattern, a CCR8$^+$ expression pattern, a CCR8$^{low/-}$ expression pattern, a CD62L$^+$ expression pattern, a CD62L$^{low/-}$ expression pattern, a ICOS$^+$ expression pattern, a ICOS$^{low/-}$ expression pattern, a CD103$^+$ expression pattern, a CD103$^{low/-}$ expression pattern, a PD-1$^+$ expression pattern, a PD-1$^{low/-}$ expression pattern, a CD134$^+$ expression pattern, a CD134$^{low/-}$ expression pattern, a GARP$^+$ expression pattern, a GARP$^{low/-}$ expression pattern, a CD45RB$^+$ expression pattern, a CD45RB$^{low/-}$ expression pattern, a CD45RO$^+$ expression pattern, a CD45RO$^{low/-}$ expression pattern, a CD95$^+$ expression pattern, a CD95$^{low/-}$ expression pattern, a CD122$^+$ expression pattern, a CD122$^{low/-}$ expression pattern, a CD147$^+$ expression pattern, a CD147$^{low/-}$ expression pattern, a CD8$^+$ expression pattern, or a CD8$^{low/-}$ expression pattern.

In still another embodiment, a population of immunosuppressive regulatory T-cells is identified based upon T-cells comprising a CD6$^{low/-}$ CD127$^{low/-}$ and one or more of the following additional biomarker expression patterns a CD4$^+$ expression pattern, a CD25$^+$ expression pattern, a CD49d$^{low/-}$ expression pattern, a CD38$^{low/-}$ expression pattern, a CD45RA$^{low/-}$ expression pattern, a HLA-Dr$^+$ expression pattern, a HLA-Dr$^{low/-}$ expression pattern, a FoxP3$^+$ expression pattern, a FoxP3$^{low/-}$ expression pattern, a CTLA-4$^+$ expression pattern, a CTLA-4$^{low/-}$ expression pattern, a GITR$^+$ expression pattern, a GITR$^{low/-}$ expression pattern, a LAG-3$^+$ expression pattern, a LAG-3$^{low/-}$ expression pattern, a CD39$^+$ expression pattern, a CD39$^{low/-}$ expression pattern, a Helios$^+$ expression pattern, a Helios$^{low/-}$ expression pattern, a FcRL3$^+$ expression pattern, a FcRL3$^{low/-}$ expression pattern, a CCR7$^+$ expression pattern, a CCR7$^{low/-}$ expression pattern, a CCR4$^+$ expression pattern, a CCR4$^{low/-}$ expression pattern, a CCR8$^+$ expression pattern, a CCR8$^{low/-}$ expression pattern, a CD62L$^+$ expression pattern, a CD62L$^{low/-}$ expression pattern, a ICOS$^+$ expression pattern, a ICOS$^{low/-}$ expression pattern, a CD103$^+$ expression pattern, a CD103$^{low/-}$ expression pattern, a PD-1$^+$ expression pattern, a PD-1$^{low/-}$ expression pattern, a CD134$^+$ expression pattern, a CD134$^{low/-}$ expression pattern, a GARP$^+$ expression pattern, a GARP$^{low/-}$ expression pattern, a CD45RB$^+$ expression pattern, a CD45RB$^{low/-}$ expression pattern, a CD45RO$^+$ expression pattern, a CD45RO$^{low/-}$ expression pattern, a CD95$^+$ expression pattern, a CD95$^{low/-}$ expression pattern, a CD122$^+$ expression pattern, a CD122$^{low/-}$ expression pattern, a CD147$^+$ expression pattern, a CD147$^{low/-}$ expression pattern, a CD8$^+$ expression pattern, or a CD8$^{low/-}$ expression pattern.

In another embodiment, a population of immunosuppressive regulatory T-cells is identified based upon T-cells comprising a CD4$^+$ CD25$^+$ CD6$^{low/-}$ and one or more of the following additional biomarker expression patterns a CD127$^{low/-}$ expression pattern, a CD49d$^{low/-}$ expression pattern, a CD38$^{low/-}$ expression pattern, a CD45RA$^{low/-}$ expression pattern, a HLA-Dr$^+$ expression pattern, a HLA-Dr$^{low/-}$ expression pattern, a FoxP3$^+$ expression pattern, a FoxP3$^{low/-}$ expression pattern, a CTLA-4$^+$ expression pattern, a CTLA-4$^{low/-}$ expression pattern, a GITR$^+$ expression pattern, a GITR$^{low/-}$ expression pattern, a LAG-3$^+$ expression pattern, a LAG-3$^{low/-}$ expression pattern, a CD39$^+$ expression pattern, a CD39$^{low/-}$ expression pattern, a Helios$^+$ expression pattern, a Helios$^{low/-}$ expression pattern, a FcRL3$^+$ expression pattern, a FcRL3$^{low/-}$ expression pattern, a CCR7$^+$ expression pattern, a CCR7$^{low/-}$ expression pattern, a CCR4$^+$ expression pattern, a CCR4$^{low/-}$ expression pattern, a CCR8$^+$ expression pattern, a CCR8$^{low/-}$ expression pattern, a CD62L$^+$ expression pattern, a CD62L$^{low/-}$ expression pattern, a ICOS$^+$ expression pattern, a ICOS$^{low/-}$ expression pattern, a CD103$^+$ expression pattern, a CD103$^{low/-}$ expression pattern, a PD-1$^+$ expression pattern, a PD-1$^{low/-}$ expression pattern, a CD134$^+$ expression pattern, a CD134$^{low/-}$ expression pattern, a GARP$^+$ expression pattern, a GARP$^{low/-}$ expression pattern, a CD45RB$^+$ expression pattern, a CD45RB$^{low/-}$ expression pattern, a CD45RO$^+$ expression pattern, a CD45RO$^{low/-}$ expression pattern, a CD95$^+$ expression pattern, a CD95$^{low/-}$ expression pattern, a CD122$^+$ expression pattern, a CD147$^+$ expression pattern, a CD147$^{low/-}$ expression pattern, a CD8$^+$ expression pattern, or a CD8$^{low/-}$ expression pattern.

In another embodiment, a population of immunosuppressive regulatory T-cells is identified based upon T-cells comprising CD6$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In yet another embodiment, a population of immunosuppressive regulatory T-cells is identified based upon T-cells comprising a CD25$^+$ CD6$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In still another embodiment, a population of immunosuppressive regulatory T-cells is identified based upon T-cells comprising a CD6$^{low/-}$ CD127$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In another embodiment, a population of immunosuppressive regulatory T-cells is identified based upon T-cells comprising a CD25$^+$ CD127$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In yet another embodiment, a population of immunosuppressive regulatory T-cells is identified based upon T-cells comprising a CD4$^+$ CD25$^+$ CD6$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In still another embodiment, a population of immunosuppressive regulatory T-cells is identified based upon T-cells comprising a CD4$^+$ CD25$^+$ CD127$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In another embodiment, a population of immunosuppressive regulatory T-cells is identified based upon T-cells comprising a CD25$^+$ CD6$^{low/-}$ CD127$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In another embodiment, two or more distinct populations of immunosuppressive regulatory T-cells is identified based upon T-cells comprising a CD6$^{low/-}$ expression pattern and one or more additional biomarker expression patterns, with the proviso that the additional biomarker expression pattern a FoxP3$^+$ expression pattern or a FoxP3$^{low/-}$ expression pattern, a CTLA-4$^+$ expression pattern or a CTLA-4$^{low/-}$ expression pattern, a CD45RA$^+$ expression pattern or a CD45RA$^{low/-}$ expression pattern, a HLA-Dr$^+$ expression pattern or a HLA-Dr$^{low/-}$ expression pattern, or any combination thereof.

In yet another embodiment, two or more distinct populations of immunosuppressive regulatory T-cells is identified based upon T-cells comprising a CD25$^+$ CD6$^{low/-}$ expression pattern and one or more additional biomarker expression patterns, with the proviso that the additional biomarker expression pattern a FoxP3$^+$ expression pattern or a FoxP3$^{low/-}$ expression pattern, a CTLA-4$^+$ expression pattern or a CTLA-4$^{low/-}$ expression pattern, a CD45RA$^+$ expression pattern or a CD45RA$^{low/-}$ expression pattern, a HLA-Dr$^+$ expression pattern or a HLA-Dr$^{low/-}$ expression pattern, or any combination thereof.

In still another embodiment, two or more distinct populations of immunosuppressive regulatory T-cells is identified based upon T-cells comprising a CD6$^{low/-}$ CD127$^{low/-}$ expression pattern and one or more additional biomarker expression patterns, with the proviso that the additional biomarker expression pattern a FoxP3$^+$ expression pattern or a FoxP3$^{low/-}$ expression pattern, a CTLA-4$^+$ expression pattern or a CTLA-4$^{low/-}$ expression pattern, a CD45RA$^+$ expression pattern or a CD45RA$^{low/-}$ expression pattern, a HLA-Dr$^+$ expression pattern or a HLA-Dr$^{low/-}$ expression pattern, or any combination thereof.

In another embodiment, two or more distinct populations of immunosuppressive regulatory T-cells is identified based upon T-cells comprising a CD4$^+$ CD25$^+$ CD6$^{low/-}$ expression pattern and one or more additional biomarker expression patterns, with the proviso that the additional biomarker expression pattern a FoxP3$^+$ expression pattern or a FoxP3$^{low/-}$ expression pattern, a CTLA-4$^+$ expression pattern or a CTLA-4$^{low/-}$ expression pattern, a CD45RA$^+$ expression pattern or a CD45RA$^{low/-}$ expression pattern, a HLA-Dr$^+$ expression pattern or a HLA-Dr$^{low/-}$ expression pattern, or any combination thereof.

In yet another embodiment, two or more distinct populations of immunosuppressive regulatory T-cells is identified based upon T-cells comprising a CD25$^+$ CD6$^{low/-}$ CD127$^{low/-}$ expression pattern and one or more additional biomarker expression patterns, with the proviso that the additional biomarker expression pattern a FoxP3$^+$ expression pattern or a FoxP3$^{low/-}$ expression pattern, a CTLA-4$^+$ expression pattern or a CTLA-4$^{low/-}$ expression pattern, a CD45RA$^+$ expression pattern or a CD45RA$^{low/-}$ expression pattern, a HLA-Dr$^+$ expression pattern or a HLA-Dr$^{low/-}$ expression pattern, or any combination thereof.

In still another embodiment, two or more distinct populations of immunosuppressive regulatory T-cells is identified based upon T-cells comprising a CD4$^+$ CD25$^+$ CD6$^{low/-}$ CD127$^{low/-}$ expression pattern and one or more additional biomarker expression patterns, with the proviso that the additional biomarker expression pattern a FoxP3$^+$ expression pattern or a FoxP3$^{low/-}$ expression pattern, a CTLA-4$^+$ expression pattern or a CTLA-4$^{low/-}$ expression pattern, a CD45RA$^+$ expression pattern or a CD45RA$^{low/-}$ expression pattern, a HLA-Dr$^+$ expression pattern or a HLA-Dr$^{low/-}$ expression pattern, or any combination thereof.

Aspects of the present specification disclose, in part, a method of obtaining a population of immunosuppressive regulatory T-cells. In one embodiment, the method disclosed herein comprises screening a sample comprising a population of T-cells to detect a level of cellular expression of a CD6 biomarker, and isolating a subpopulation of T-cells comprising a CD6$^{low/-}$ expression pattern, thereby obtaining the population of immunosuppressive regulatory T-cells.

In another embodiment, the method disclosed herein comprises contacting a sample comprising a population of T-cells with a CD6 biomarker ligand; screening the population of T-cells to detect a level of cellular expression of a CD6 biomarker; and isolating a subpopulation of T-cells comprising a CD6$^{low/-}$ expression pattern, thereby obtaining the population of immunosuppressive regulatory T-cells.

In yet another embodiment, the method disclosed herein comprises screening a sample comprising a population of T-cells to detect a level of cellular expression of at least two different biomarkers, wherein the at least two different biomarkers include a CD25 biomarker and a CD6 biomarker; and isolating a subpopulation of T-cells comprising a CD25$^+$ CD6$^{low/-}$ expression pattern, thereby obtaining the population of immunosuppressive regulatory T-cells.

In yet another embodiment, the method disclosed herein comprises contacting a sample comprising a population of T-cells with at least two different biomarkers ligands, wherein the at least two different biomarker ligands include a CD25 biomarker ligand and a CD6 biomarker ligand; screening the population of T-cells to detect a level of cellular expression of at least two different biomarkers; wherein the at least two different biomarkers include a CD25 biomarker and a CD6 biomarker; and isolating a subpopulation of T-cells comprising a CD25$^+$ CD6$^{low/-}$ expression pattern, thereby obtaining the population of immunosuppressive regulatory T-cells.

In still another embodiment, the method disclosed herein comprises screening a sample comprising a population of T-cells to detect a level of cellular expression of at least two different biomarkers, wherein the at least two different biomarkers include a CD6 biomarker and a CD127 biomarker; and isolating a subpopulation of T-cells comprising a CD6$^{low/-}$ CD127$^{low/-}$ expression pattern, thereby obtaining the population of immunosuppressive regulatory T-cells.

In still another embodiment, the method disclosed herein comprises contacting a sample comprising a population of T-cells with at least two different biomarkers ligands, wherein the at least two different biomarker ligands include a CD6 biomarker ligand and a CD127 biomarker ligand; screening the population of T-cells to detect a level of cellular expression of at least two different biomarkers; wherein the at least two different biomarkers include a CD6 biomarker and a CD127 biomarker; and isolating a subpopulation of T-cells comprising a CD6$^{low/-}$ CD127$^{low/-}$ expression pattern, thereby obtaining the population of immunosuppressive regulatory T-cells.

In another embodiment, the method disclosed herein comprises screening a sample comprising a population of T-cells to detect a level of cellular expression of at least three different biomarkers, wherein the at least three different biomarkers include a CD4 biomarker, a CD25 biomarker, and a CD6 biomarker; and isolating a subpopulation of T-cells comprising a CD4$^+$ CD25$^+$ CD6$^{low/-}$ expression pattern, thereby obtaining the population of immunosuppressive regulatory T-cells.

In another embodiment, the method disclosed herein comprises contacting a sample comprising a population of T-cells with at least three different biomarkers ligands, wherein the at least three different biomarker ligands include a CD4 biomarker ligand, a CD25 biomarker ligand, and a CD6 biomarker ligand; screening the population of T-cells to detect a level of cellular expression of at least three different biomarkers; wherein the at least three different biomarkers include a CD4 biomarker, a CD25 biomarker, and a CD6 biomarker; and isolating a subpopulation of T-cells comprising a CD4$^+$ CD25$^+$ CD6$^{low/-}$ expression pattern, thereby obtaining the population of immunosuppressive regulatory T-cells.

In yet another embodiment, the method disclosed herein comprises screening a sample comprising a population of T-cells to detect a level of cellular expression of at least three different biomarkers, wherein the at least three different biomarkers include a CD25 biomarker, a CD6 biomarker, and a CD127 biomarker; and isolating a subpopulation of T-cells comprising a CD25$^+$ CD6$^{low/-}$ CD127$^{low/-}$ expression pattern, thereby obtaining the population of immunosuppressive regulatory T-cells.

In yet another embodiment, the method disclosed herein comprises contacting a sample comprising a population of T-cells with at least three different biomarkers ligands, wherein the at least three different biomarker ligands include a CD25 biomarker ligand, a CD6 biomarker ligand, and a CD127 biomarker ligand; screening the population of T-cells to detect a level of cellular expression of at least three different biomarkers; wherein the at least three different biomarkers include a CD25 biomarker, a CD6 biomarker, and a CD127 biomarker; and isolating a subpopulation of T-cells comprising a CD25$^+$ CD6$^{low/-}$ CD127$^{low/-}$ expression pattern, thereby obtaining the population of immunosuppressive regulatory T-cells.

The screening and contacting steps are as described herein.

A population of immunosuppressive regulatory T-cells is isolated or enriched based on a characteristic expression pattern of one or more biomarkers. As for the screening step disclosed herein, such cells are isolated or enriched according to the expression levels biomarker or biomarkers based upon readily discernible differences in staining intensity as is known to one of ordinary skill in the art. Typically, the expression of a biomarker expression pattern is classified as high (biomarker$^{hi}$), +(biomarker$^+$), low (biomarker$^{low}$) and −(biomarker$^-$).

A population of immunosuppressive regulatory T-cells may be comprised substantially of cells comprising the desired biomarker expression pattern. As used herein, the term "substantially", when used in reference to a population of cells comprising the desired biomarker expression pattern refers to a population of cells for which at least 80% of the total number of cells from the population comprises the desired biomarker expression pattern. In aspects of this embodiment, a population of immunosuppressive regulatory T-cells comprising the desired biomarker expression pattern makes up, e.g., at least 83%, at least 85% at least 88%, or at least 90%, at least 93%, at least 95% at least 98%, or at least 99% of the total number of cells from the population. In other aspects of this embodiment, a population of immunosuppressive regulatory T-cells comprising the desired biomarker expression pattern is makes up, e.g., at least two-fold, at least four-fold, at least eight-fold, at least ten-fold, at least 20-fold, at least 50-fold, or at least 100-fold as compared to the source population of T-cells from the sample.

A population of immunosuppressive regulatory T-cells may be isolated or enriched using positive selection or negative selection of the cells of interest. Additionally, a population of immunosuppressive regulatory T-cells may be isolated or enriched using both positive selection and negative selection of the cells of interest. As used herein, the term "positive selection" refers to the selection of specified cells from a mixture or starting population of cells based upon the high or positive expression of a biomarker on the specified cells. As used herein, the term "negative selection" refers to the selection of specified cells from a mixture or starting population of cells based upon the low or negative expression of a biomarker on the specified cells. The biomarkers used for positive or negative selection of cells may be detected by, e.g., flow cytometric sorter, MACS, solid-phase attachment, panning, and chromatography. Immunoselection of two or more biomarkers on cells may be performed in one or more steps, wherein each step positively or negatively selects for one or more biomarkers. When immunoselection of two or more biomarkers is performed in one step using flow cytometric sorter, the two or more different biomarkers may be labeled with different fluorophores.

In aspects of this embodiment, a population of immunosuppressive regulatory T-cells comprising the desired biomarker expression pattern is enriched by, e.g., at least 20%, at least 30%, at least 40% at least 50%, or at least 60%, at least 70%, at least 80%, or at least 90% as compared to the total number of cells from the source population of cells. In other aspects of this embodiment, a population of immunosuppressive regulatory T-cells comprising the desired biomarker expression pattern is enriched by, e.g., at least two-fold, at least four-fold, at least eight-fold, at least ten-fold, at least 20-fold, at least 50-fold, or at least 100-fold as compared to the total number of cells from the source population of cells.

In other aspects of this embodiment, a population of immunosuppressive regulatory T-cells comprising the desired biomarker expression pattern is enriched to, e.g., at least 80%, at least 85%, at least 90%, at least 95%, or at least 98% of the total number of cells in the sample. In yet other aspects of this embodiment, a population of immunosuppressive regulatory T-cells comprising the desired biomarker expression pattern is enriched to, e.g., about 80% to about 85%, about 80% to about 90%, about 80% to about 95%, about 80% to about 98%, about 80% to about 100%, about 85% to about 90%, about 85% to about 95%, about 85% to about 98%, about 85% to about 100%, about 90% to about 95%, about 90% to about 98%, or about 90% to about 100%, of the total number of cells in the sample.

In other aspects of this embodiment, a subpopulation of immunosuppressive regulatory T-cells comprising the desired biomarker expression pattern is isolated to, e.g., at least 80%, at least 85%, at least 90%, at least 95%, or at least 98% from the total number of cells in the sample. In yet other aspects of this embodiment, a subpopulation of immunosuppressive regulatory T-cells comprising the desired biomarker expression pattern is isolated to, e.g., about 80% to about 85%, about 80% to about 90%, about 80% to about 95%, about 80% to about 98%, about 80% to about 100%, about 85% to about 90%, about 85% to about 95%, about 85% to about 98%, about 85% to about 100%, about 90% to about 95%, about 90% to about 98%, or about 90% to about 100%, from the total number of cells in the sample.

In another aspect, a population of immunosuppressive regulatory T-cells comprising the desired biomarker expression pattern is isolated by a negative selection scheme that depletes $CD6^+$ cells from the cells in the sample. In yet another aspect, a population of immunosuppressive regulatory T-cells comprising the desired biomarker expression pattern is enriched by a negative selection scheme that depletes $CD6^+$ cells from the cells in the sample.

A population of immunosuppressive regulatory T-cells is obtained based on a characteristic expression pattern of one or more biomarkers. Cells comprising the desired biomarker expression pattern may be isolated or enriched using a detection method based on fluorescence, bioluminescence, chemiluminescence, spectroscopic, photochemical, biochemical, immunochemical, chemical, magnetic, size, volume, density, opacity, or other physical means known to one of ordinary skill in the art.

In an embodiment, isolating a subpopulation of T-cells comprising a desired biomarker expression pattern is accomplished using a cell sorter as disclosed herein. In an aspect of this embodiment, isolating a subpopulation of T-cells comprising a desired biomarker expression pattern is accomplished using flow cytometric sorter as disclosed herein. In another embodiment, isolating a subpopulation of T-cells comprising a desired biomarker expression pattern is accomplished using MACS as disclosed herein. A biomarker expression pattern may be used for the positive selection or the negative selection of cells of interest as disclosed herein. The biomarkers expression pattern used for positive or negative selection of cells may be detected by, e.g., flow cytometric sorter, MACS, panning, and chromatography.

The cut off value for designating a cell as a $biomarker^{hi}$ cell, a $biomarker^+$ cell, a $biomarker^{low}$ cell, or a $biomarker^-$ cell is as disclosed herein. Cells may also be distinguished by obtaining the frequency distribution of biomarker staining for all cells and generating a population curve fit to a higher staining population and a lower staining population as disclosed herein.

In one embodiment, a population of immunosuppressive regulatory T-cells is isolated or enriched based upon T-cells comprising a $CD6^{low/-}$ expression pattern. In an aspect of this embodiment, a population of immunosuppressive regulatory T-cells is isolated or enriched based upon T-cells comprising a $CD25^+$ $CD6^{low/-}$ expression pattern. In yet another aspect of this embodiment, a population of immunosuppressive regulatory T-cells is isolated or enriched based upon T-cells comprising a $CD6^{low/-}$ $CD127^{low/-}$ expression pattern. In still another aspect of this embodiment, a population of immunosuppressive regulatory T-cells is isolated or enriched based upon T-cells comprising a $CD6^{low/-}$ $CD38^{low/-}$ expression pattern. In still another aspect of this embodiment, a population of immunosuppressive regulatory T-cells is isolated or enriched based upon T-cells comprising a $CD6^{low/-}$ $CD49^{low/-}$ expression pattern.

In another aspect of this embodiment, a population of immunosuppressive regulatory T-cells is isolated or enriched based upon T-cells comprising a $CD4^+$ $CD25^+$ $CD6^{low/-}$ expression pattern. In yet another aspect of this embodiment, a population of immunosuppressive regulatory T-cells is isolated or enriched based upon T-cells comprising a $CD25^+$ $CD6^{low/-}$ $CD127^{low/-}$ expression pattern. In still another aspect of this embodiment, a population of immunosuppressive regulatory T-cells is isolated or enriched based upon T-cells comprising a $CD6^{low/-}$ $CD127^{low/-}$ $CD49d^{low/-}$ expression pattern. In still another aspect of this embodiment, a population of immunosuppressive regulatory T-cells is isolated or enriched based upon T-cells comprising a $CD6^{low/-}$ $CD127^{low/-}$ $CD38^{low/-}$ expression pattern.

In other aspects of this embodiment, a population of immunosuppressive regulatory T-cells is isolated or enriched based upon T-cells comprising a $CD4^+$ $CD25^+$ $CD6^{low/-}$ $CD127^{low/-}$ expression pattern, a $CD4^+$ $CD25^+$ $CD6^{low/-}$ $CD49d^{low/-}$ expression pattern, a $CD4^+$ $CD25^+$ $CD6^{low/-}$ $CD38^{low/-}$ expression pattern, a $CD4^+$ $CD25^+$ $CD6^{low/-}$ $CD45RA^{low/-}$ expression pattern, a $CD25^+$ $CD6^{low/-}$ $CD127^{low/-}$ $CD49d^{low/-}$ expression pattern, a $CD25^+$ $CD6^{low/-}$ $CD127^{low/-}$ $CD38^{low/-}$ expression pattern, or a $CD6^{low/-}$ $CD127^{low/-}$ $CD49d^{low/-}$ $CD38^{low/-}$ expression pattern.

In other aspects of this embodiment, a population of immunosuppressive regulatory T-cells is isolated or enriched based upon T-cells comprising a $CD4^+$ $CD25^+$ $CD6^{low/-}$ HLA-Dr$^+$ expression pattern, a $CD4^+$ $CD25^+$ $CD6^{low/-}$ HLA-Dr$^{low/-}$ expression pattern, a $CD4^+$ $CD25^+$ $CD6^{low/-}$ FoxP3$^+$ expression pattern, a $CD4^+$ $CD25^+$ $CD6^{low/-}$ FoxP3$^{low/-}$ expression pattern, a $CD4^+$ $CD25^+$ $CD6^{low/-}$ CTLA-4$^+$ expression pattern, a $CD4^+$ $CD25^+$ $CD6^{low/-}$ CTLA-4$^{low/-}$ expression pattern, a $CD4^+$ $CD25^+$ $CD6^{low/-}$ GITR$^+$ expression pattern, a $CD4^+$ $CD25^+$ $CD6^{low/-}$ GITR$^{low/-}$ expression pattern, a $CD4^+$ $CD25^+$ $CD6^{low/-}$ LAG-3$^+$ expression pattern, a $CD4^+$ $CD25^+$ $CD6^{low/-}$ LAG-3$^{low/-}$ expression pattern, a $CD4^+$ $CD25^+$ $CD6^{low/-}$ CD39$^+$ expression pattern, a $CD4^+$ $CD25^+$ $CD6^{low/-}$ CD39$^{low/-}$ expression pattern, a $CD4^+$ $CD25^+$ $CD6^{low/-}$ Helios$^+$ expression pattern, a $CD4^+$ $CD25^+$ $CD6^{low/-}$ Helios$^{low/-}$ expression pattern, a $CD4^+$ $CD25^+$ $CD6^{low/-}$ FcRL3$^+$ expression pattern, a $CD4^+$ $CD25^+$ $CD6^{low/-}$ FcRL3$^{low/-}$ expression pattern, a $CD4^+$ $CD25^+$ $CD6^{low/-}$ CCR7$^+$ expression pattern, a $CD4^+$ $CD25^+$ $CD6^{low/-}$ CCR7$^{low/-}$ expression pattern, a $CD4^+$ $CD25^+$ $CD6^{low/-}$ CCR4$^+$ expression pattern, a $CD4^+$ $CD25^+$ $CD6^{low/-}$ CCR4$^{low/-}$ expression pattern, a $CD4^+$ $CD25^+$ $CD6^{low/-}$ CCR8$^+$ expression pattern, a $CD4^+$ $CD25^+$ $CD6^{low/-}$ CCR8$^{low/-}$ expression pattern, a $CD4^+$ $CD25^+$ $CD6^{low/-}$ CD62L$^+$ expression pattern, a $CD4^+$ $CD25^+$ $CD6^{low/-}$ CD62L$^{low/-}$ expression pattern, a $CD4^+$ $CD25^+$ $CD6^{low/-}$ ICOS$^+$ expression pattern, a $CD4^+$ $CD25^+$ $CD6^{low/-}$ ICOS$^{low/-}$ expression pattern, a $CD4^+$ $CD25^+$ $CD6^{low/-}$ CD103$^+$ expression pattern, a $CD4^+$ $CD25^+$ $CD6^{low/-}$ CD103$^{low/-}$ expression pattern, a $CD4^+$ $CD25^+$ $CD6^{low/-}$ PD-1$^+$ expression pattern, a $CD4^+$ $CD25^+$ $CD6^{low/-}$ PD-1$^{low/-}$ expression pattern, a $CD4^+$ $CD25^+$ $CD6^{low/-}$ CD134$^+$ expression pattern, a $CD4^+$ $CD25^+$ $CD6^{low/-}$ CD134$^{low/-}$ expression pattern, a $CD4^+$ $CD25^+$ $CD6^{low/-}$ GARP$^+$ expression pattern, a $CD4^+$ $CD25^+$ $CD6^{low/-}$ GARP$^{low/-}$ expression pattern, a $CD4^+$ $CD25^+$ $CD6^{low/-}$ CD45RB$^+$ expression pattern, a $CD4^+$ $CD25^+$ $CD6^{low/-}$ CD45RB$^{low/-}$ expression pattern, a $CD4^+$ $CD25^+$ $CD6^{low/-}$ CD45RO$^+$ expression pattern, a $CD4^+$ $CD25^+$ $CD6^{low/-}$ CD45RO$^{low/-}$ expression pattern, a $CD4^+$ $CD25^+$ $CD6^{low/-}$ CD95$^+$ expression pattern, a $CD4^+$ $CD25^+$ $CD6^{low/-}$ CD95$^{low/-}$ expression pattern, a $CD4^+$ $CD25^+$ $CD6^{low/-}$ CD122$^+$ expression pattern, a $CD4^+$ $CD25^+$ $CD6^{low/-}$ CD122$^{low/-}$ expression pattern, a $CD4^+$ $CD25^+$ $CD6^{low/-}$ CD147$^{low/-}$ expression pattern, a $CD4^+$ $CD25^+$ $CD6^{low/-}$ CD8$^+$ expression pattern, or a $CD4^+$ $CD25^+$ $CD6^{low/-}$ CD8$^{low/-}$ expression pattern.

In another embodiment, a population of immunosuppressive regulatory T-cells is isolated or enriched based upon T cells comprising a $CD6^{low/-}$ expression pattern and one or more of the following additional biomarker expression patterns a $CD4^+$ expression pattern, a $CD25^+$ expression pattern, a $CD127^{low/-}$ expression pattern, a $CD49d^{low/-}$ expression pattern, a $CD38^{low/-}$ expression pattern, a $CD45RA^{low/-}$ expression pattern, a HLA-Dr$^+$ expression pattern, a HLA-Dr$^{low/-}$ expression pattern, a FoxP3$^+$ expression pattern, a FoxP3$^{low/-}$ expression pattern, a CTLA-4$^+$ expression pattern, a CTLA-4$^{low/-}$ expression pattern, a GITR$^+$ expression pattern, a GITR$^{low/-}$ expression pattern, a LAG-3$^+$ expression pattern, a LAG-3$^{low/-}$ expression pattern, a CD39$^+$ expression pattern, a CD39$^{low/-}$ expression pattern, a Helios$^+$ expression pattern, a Helios$^{low/-}$ expression pattern, a FcRL3$^+$ expression pattern, a FcRL3$^{low/-}$ expression pattern, a CCR7$^+$ expression pattern, a CCR7$^{low/-}$ expression pattern, a CCR4$^+$ expression pattern, a CCR4$^{low/-}$ expression pattern, a CCR8$^+$ expression pattern, a CCR8$^{low/-}$ expression pattern, a CD62L$^+$ expression pattern, a CD62L$^{low/-}$ expression pattern, a ICOS$^+$ expression pattern, a ICOS$^{low/-}$ expression pattern, a CD103$^+$ expression pattern, a CD103$^{low/-}$ expression pattern, a PD-1$^+$ expression pattern, a PD-1$^{low/-}$ expression pattern, a CD134$^+$ expression pattern, a CD134$^{low/-}$ expression pattern, a GARP$^+$ expression pattern, a GARP$^{low/-}$ expression pattern, a CD45RB$^+$ expression pattern, a CD45RB$^{low/-}$ expression pattern, a CD45RO$^+$ expression pattern, a CD45RO$^{low/-}$ expression pattern, a CD95$^+$ expression pattern, a CD95$^{low/-}$ expression pattern, a CD122$^+$ expression pattern, a CD122$^{low/-}$ expression pattern, a CD147$^+$ expression pattern, a CD147$^{low/-}$ expression pattern, a CD8$^+$ expression pattern, or a CD8$^{low/-}$ expression pattern.

In yet another embodiment, a population of immunosuppressive regulatory T-cells is isolated or enriched based upon T cells comprising a $CD25^+$ $CD6^{low/-}$ expression pattern and one or more of the following additional biomarker expression patterns a $CD4^+$ expression pattern, a $CD127^{low/-}$ expression pattern, a $CD49d^{low/-}$ expression pattern, a $CD38^{low/-}$ expression pattern, a $CD45RA^{low/-}$ expression pattern, a HLA-Dr$^+$ expression pattern, a HLA-Dr$^{low/-}$ expression pattern, a FoxP3$^+$ expression pattern, a FoxP3$^{low/-}$ expression pattern, a CTLA-4$^+$ expression pattern, a CTLA-4$^{low/-}$ expression pattern, a GITR$^+$ expression pattern, a GITR$^{low/-}$ expression pattern, a LAG-3$^+$ expression pattern, a LAG-3$^{low/-}$ expression pattern, a CD39$^+$ expression pattern, a CD39$^{low/-}$ expression pattern, a Helios$^+$ expression pattern, a Helios$^{low/-}$ expression pattern, a FcRL3$^+$ expression pattern, a FcRL3$^{low/-}$ expression pattern, a CCR7$^+$ expression pattern, a CCR7$^{low/-}$ expression pattern, a CCR4$^+$ expression pattern, a CCR4$^{low/-}$ expression pattern, a CCR8$^+$ expression pattern, a CCR8$^{low/-}$ expression pattern, a CD62L$^+$ expression pattern, a CD62L$^{low/-}$ expression pattern, a ICOS$^+$ expression pattern, a ICOS$^{low/-}$ expression pattern, a CD103$^+$ expression pattern, a CD103$^{low/-}$ expression pattern, a PD-1$^+$ expression pattern, a PD-1$^{low/-}$ expression pattern, a CD134$^+$ expression pattern, a CD134$^{low/-}$ expression pattern, a GARP$^+$ expression pattern, a GARP$^{low/-}$ expression pattern, a CD45RB$^+$ expression pattern, a CD45RB$^{low/-}$ expression pattern, a CD45RO$^+$ expression pattern, a CD45RO$^{low/-}$ expression pattern, a CD95$^+$ expression pattern, a CD95$^{low/-}$ expression pattern, a CD122$^+$ expression pattern, a CD122$^{low/-}$ expression pattern, a CD147$^+$ expression pattern, a CD147$^{low/-}$ expression pattern, a CD8$^+$ expression pattern, or a CD8$^{low/-}$ expression pattern.

In still another embodiment, a population of immunosuppressive regulatory T-cells is isolated or enriched based upon T cells comprising a $CD6^{low/-}$ $CD127^{low/-}$ expression pattern and one or more of the following additional biomarker expression patterns a $CD4^+$ expression pattern, a $CD25^+$ expression pattern, a $CD49d^{low/-}$ expression pattern, a $CD38^{low/-}$ expression pattern, a $CD45RA^{low/-}$ expression pattern, a HLA-Dr$^+$ expression pattern, a HLA-Dr$^{low/-}$ expression pattern, a FoxP3$^+$ expression pattern, a FoxP3$^{low/-}$ expression pattern, a CTLA-4$^+$ expression pattern, a CTLA-4$^{low/-}$ expression pattern, a GITR$^+$ expression pattern, a GITR$^{low/-}$ expression pattern, a LAG-3$^+$ expression pattern, a LAG-3$^{low/-}$ expression pattern, a CD39$^+$ expression pattern, a CD39$^{low/-}$ expression pattern, a Helios$^+$ expression pattern, a Helios$^{low/-}$ expression pattern, a FcRL3$^+$ expression pattern, a FcRL3$^{low/-}$ expression pattern, a CCR7$^+$ expression pattern, a CCR7$^{low/-}$ expression pattern, a CCR4$^+$ expression pattern, a CCR4$^{low/-}$ expression pattern, a CCR8$^+$ expression pattern, a CCR8$^{low/-}$ expression pattern, a CD62L$^+$ expression pattern, a CD62L$^{low/-}$ expression pattern, a ICOS$^+$ expression pattern, a ICOS$^{low/-}$ expression pattern, a CD103$^+$ expression pattern, a CD103$^{low/-}$ expression pattern, a PD-1$^+$ expression pattern, a PD-1$^{low/-}$ expression pattern, a CD134$^+$ expression pattern, a CD134$^{low/-}$ expression pattern, a GARP$^+$ expression pattern, a GARP$^{low/-}$ expression pattern, a CD45RB$^+$ expression pattern, a CD45RB$^{low/-}$ expression pattern, a CD45RO$^+$ expression pattern, a CD45RO$^{low/-}$ expression pattern, a CD95$^+$ expression pattern, a CD95$^{low/-}$ expression pattern, a CD122$^+$ expression pattern, a CD122$^{low/-}$ expression pattern, a CD147$^+$ expression pattern, a CD147$^{low/-}$ expression pattern, a CD8$^+$ expression pattern, or a CD8$^{low/-}$ expression pattern.

In another embodiment, a population of immunosuppressive regulatory T-cells is isolated or enriched based upon T cells comprising a CD4$^+$ CD25$^+$ CD6$^{low/-}$ expression pattern and one or more of the following additional biomarker expression patterns a CD127$^{low/-}$ expression pattern, a CD49d$^{low/-}$ expression pattern, a CD38$^{low/-}$ expression pattern, a CD45RA$^{low/-}$ expression pattern, a HLA-Dr$^+$ expression pattern, a HLA-Dr$^{low/-}$ expression pattern, a FoxP3$^+$ expression pattern, a FoxP3$^{low/-}$ expression pattern, a CTLA-4$^+$ expression pattern, a CTLA-4$^{low/-}$ expression pattern, a GITR$^+$ expression pattern, a GITR$^{low/-}$ expression pattern, a LAG-3$^+$ expression pattern, a LAG-3$^{low/-}$ expression pattern, a CD39$^+$ expression pattern, a CD39$^{low/-}$ expression pattern, a Helios$^+$ expression pattern, a Helios$^{low/-}$ expression pattern, a FcRL3$^+$ expression pattern, a FcRL3$^{low/-}$ expression pattern, a CCR7$^+$ expression pattern, a CCR7$^{low/-}$ expression pattern, a CCR4$^+$ expression pattern, a CCR4$^{low/-}$ expression pattern, a CCR8$^+$ expression pattern, a CCR8$^{low/-}$ expression pattern, a CD62L$^+$ expression pattern, a CD62L$^{low/-}$ expression pattern, a ICOS$^+$ expression pattern, a ICOS$^{low/-}$ expression pattern, a CD103$^+$ expression pattern, a CD103$^{low/-}$ expression pattern, a PD-1$^+$ expression pattern, a PD-1$^{low/-}$ expression pattern, a CD134$^+$ expression pattern, a CD134$^{low/-}$ expression pattern, a GARP$^+$ expression pattern, a GARP$^{low/-}$ expression pattern, a CD45RB$^+$ expression pattern, a CD45RB$^{low/-}$ expression pattern, a CD45RO$^+$ expression pattern, a CD45RO$^{low/-}$ expression pattern, a CD95$^+$ expression pattern, a CD95$^{low/-}$ expression pattern, a CD122$^+$ expression pattern, a CD122$^{low/-}$ expression pattern, a CD147$^+$ expression pattern, a CD147$^{low/-}$ expression pattern, a CD8$^+$ expression pattern, or a CD8$^{low/-}$ expression pattern.

In another embodiment, a population of immunosuppressive regulatory T-cells is isolated or enriched based upon T cells comprising CD6$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In yet another embodiment, a population of immunosuppressive regulatory T-cells is isolated or enriched based upon T cells comprising a CD25$^+$ CD6$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In still another embodiment, a population of immunosuppressive regulatory T-cells is isolated or enriched based upon T cells comprising a CD6$^{low/-}$ CD127$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In another embodiment, a population of immunosuppressive regulatory T-cells is isolated or enriched based upon T cells comprising a CD25$^+$ CD127$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In yet another embodiment, a population of immunosuppressive regulatory T-cells is isolated or enriched based upon T cells comprising a CD4$^+$ CD25$^+$ CD6$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In still another embodiment, a population of immunosuppressive regulatory T-cells is isolated or enriched based upon T cells comprising a CD4$^+$ CD25$^+$ CD127$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

In another embodiment, a population of immunosuppressive regulatory T-cells is isolated or enriched based upon T cells comprising a CD25$^+$ CD6$^{low/-}$ CD127$^{low/-}$ expression pattern and one or more additional biomarker expression patterns, with the proviso that the additional biomarker expression pattern is not a FoxP3$^+$ expression pattern, a FoxP3$^{low/-}$ expression pattern, a CTLA-4$^+$ expression pattern, a CTLA-4$^{low/-}$ expression pattern, or any combination thereof.

Aspects of the present specification disclose, in part, a method of obtaining an expanded population of immunosuppressive regulatory T-cells. In one embodiment, the method disclosed herein comprises screening a sample comprising a population of T-cells to detect a level of cellular expression of a CD6 biomarker, and isolating a subpopulation of T-cells comprising a CD6$^{low/-}$ expression pattern; and expanding the subpopulation of T-cells comprising a CD6$^{low/-}$ expression pattern, thereby obtaining the expanded population of immunosuppressive regulatory T-cells.

In another embodiment, the method disclosed herein comprises contacting a sample comprising a population of T-cells with a CD6 biomarker ligand; screening the population of T-cells to detect a level of cellular expression of a CD6 biomarker; and isolating a subpopulation of T-cells comprising a CD6$^{low/-}$ expression pattern; and contacting the subpopulation of T-cells comprising a CD6$^{low/-}$ expression pattern with a stimulatory composition, thereby obtaining the expanded population of immunosuppressive regulatory T-cells.

In yet another embodiment, the method disclosed herein comprises screening a sample comprising a population of T-cells to detect a level of cellular expression of the at least two different biomarkers, wherein the at least two different biomarkers include a CD25 biomarker and a CD6 biomarker; and isolating a subpopulation of T-cells comprising a CD25$^+$ CD6$^{low/-}$ expression pattern; and contacting the subpopulation of T-cells comprising a CD25$^+$ CD6$^{low/-}$ expression pattern with a stimulatory composition, thereby obtaining the expanded population of immunosuppressive regulatory T-cells.

In yet another embodiment, the method disclosed herein comprises contacting a sample comprising a population of T-cells with at least three different biomarkers ligands, wherein the at least two different biomarker ligands include a CD25 biomarker ligand and a CD6 biomarker ligand; screening the population of T-cells to detect a level of cellular expression of the at least two different biomarkers; wherein the at least two different biomarkers include a CD25 biomarker and a CD6 biomarker; isolating a subpopulation of T-cells comprising a CD25$^+$ CD6$^{low/-}$ expression pattern; and contacting the subpopulation of T-cells comprising a CD25$^+$ CD6$^{low/-}$ expression pattern with a stimulatory composition, thereby obtaining the expanded population of immunosuppressive regulatory T-cells.

In still another embodiment, the method disclosed herein comprises screening a sample comprising a population of T-cells to detect a level of cellular expression of the at least two different biomarkers, wherein the at least two different biomarkers include a CD6 biomarker and a CD127 biomarker; and isolating a subpopulation of T-cells comprising a CD6$^{low/-}$ CD127$^{low/-}$ expression pattern; and contacting the subpopulation of T-cells comprising a CD6$^{low/-}$ CD127$^{low/-}$ expression pattern with a stimulatory composition, thereby obtaining the expanded population of immunosuppressive regulatory T-cells.

In still another embodiment, the method disclosed herein comprises contacting a sample comprising a population of T-cells with at least three different biomarkers ligands, wherein the at least two different biomarker ligands include a CD6 biomarker ligand and a CD127 biomarker ligand; screening the population of T-cells to detect a level of cellular expression of the at least two different biomarkers; wherein the at least two different biomarkers include a CD6 biomarker and a CD127 biomarker; isolating a subpopulation of T-cells comprising a CD6$^{low/-}$ CD127$^{low/-}$ expression pattern; and contacting the subpopulation of T-cells comprising a CD6$^{low/-}$ CD127$^{low/-}$ expression pattern with a stimulatory composition, thereby obtaining the expanded population of immunosuppressive regulatory T-cells.

In another embodiment, the method disclosed herein comprises screening a sample comprising a population of T-cells to detect a level of cellular expression of the at least three different biomarkers, wherein the at least three different biomarkers include a CD4 biomarker, a CD25 biomarker, and a CD6 biomarker; and isolating a subpopulation of T-cells comprising a CD4$^+$ CD25$^+$ CD6$^{low/-}$ expression pattern; and contacting the subpopulation of T-cells comprising a CD4$^+$ CD25$^+$ CD6$^{low/-}$ expression pattern with a stimulatory composition, thereby obtaining the expanded population of immunosuppressive regulatory T-cells.

In another embodiment, the method disclosed herein comprises contacting a sample comprising a population of T-cells with at least three different biomarkers ligands, wherein the at least three different biomarker ligands include a CD4 biomarker ligand, a CD25 biomarker ligand, and a CD6 biomarker ligand; screening the population of T-cells to detect a level of cellular expression of the at least three different biomarkers; wherein the at least three different biomarkers include a CD4 biomarker, a CD25 biomarker, and a CD6 biomarker; isolating a subpopulation of T-cells comprising a CD4$^+$ CD25$^+$ CD6$^{low/-}$ expression pattern; and contacting the subpopulation of T-cells comprising a CD4$^+$ CD25$^+$ CD6$^{low/-}$ expression pattern with a stimulatory composition, thereby obtaining the expanded population of immunosuppressive regulatory T-cells.

In yet another embodiment, the method disclosed herein comprises screening a sample comprising a population of T-cells to detect a level of cellular expression of the at least three different biomarkers, wherein the at least three different biomarkers include a CD4 biomarker, a CD25 biomarker, and a CD6 biomarker; and isolating a subpopulation of T-cells comprising a CD25$^+$ CD6$^{low/-}$ CD127$^{low/-}$ expression pattern; and contacting the subpopulation of T-cells comprising a CD25$^+$ CD6$^{low/-}$ CD127$^{low/-}$ expression pattern with a stimulatory composition, thereby obtaining the expanded population of immunosuppressive regulatory T-cells.

In yet another embodiment, the method disclosed herein comprises contacting a sample comprising a population of T-cells with at least three different biomarkers ligands, wherein the at least three different biomarker ligands include a CD25 biomarker ligand, a CD6 biomarker ligand, and a CD127 biomarker ligand; screening the population of T-cells to detect a level of cellular expression of the at least three different biomarkers; wherein the at least three different biomarkers include a CD25 biomarker, a CD6 biomarker, and a CD127 biomarker; isolating a subpopulation of T-cells comprising a CD25$^+$ CD6$^{low/-}$ CD127$^{low/-}$ expression pattern; and contacting the subpopulation of T-cells comprising a CD25$^+$ CD6$^{low/-}$ CD127$^{low/-}$ expression pattern with a stimulatory composition, thereby obtaining the expanded population of immunosuppressive regulatory T-cells.

The screening, contacting, and isolating steps are as described herein.

Expanding a subpopulation of T-cells comprising a desired biomarker expression pattern can be accomplished by contacting the subpopulation of T-cells with a stimulatory composition using standard cell culturing procedures. A stimulatory composition promotes growth of the T cells by antigen-specifically binding and activating the T cell receptor complex. A stimulatory composition comprises an effective amount of a TCR/CD3 activator that is antigen-specific. The stimulatory composition may further include one or more additional agents, e.g., a co-stimulatory agent, a second regulatory T cell stimulatory agent, or agents that generally promote the survival and/or growth of T cells. A stimulatory composition can be in solution or suspension. To promote activation and expansion, the TCR/CD3 activator and the TCR co-stimulator can be typically immobilized on a 3-dimensional solid surface, such as a host cell, beads, or other substrate. See, e.g., Thomas et al, Clin. Immunol. 105: 259-272 (2002), which is hereby incorporated by reference in its entirety. Cells suitable for use as substrates include artificial antigen-presenting cells (aAPCs). See, e.g., Kim, et al., Nat. Biotechnol. 22(4):403-410 (2004); and Thomas, et al., Clin. Immunol. 105(3): 259-272 (2002), each of which is hereby incorporated by reference in its entirety. Beads can be plastic, glass, or any other suitable material, typically in the 1 μm to 20 μm in diameter range. In one embodiment, the activators may be immobilized on paramagnetic beads provided in a cell:bead ratio of between 2:1 and 1:5, preferably between 1:1 and 1:3. Optimal bead size can be empirically determined, though typically the size falls in the range of 1 µm to 20 µm in diameter.

A TCR/CD3 activator is a multivalent antibody or ligand for TCR/CD3, including antigen non-specific activators such as, e.g., an α-CD3 antibody, and antigen-specific activators, such as, e.g., an Major Histocompatibility Complex (MHC)-peptide multimers. See, e.g. Yee, et al., Adoptive T cell therapy using antigen-specific CD8+ T cell clones for the treatment of patients with metastatic melanoma: In vivo persistence, migration, and antitumor effect of transferred T cells, Proc Natl. Acad. Sci. USA 99(25): 16168-16173 (2002); Butterfield, et al., T-Cell responses to HLA-A*0201 immunodominant peptides derived from .alpha.-fetoprotein in patients with hepatocellular cancer, Clin. Cancer Res. 9(16): 5902-5908 (2003); and Yee, et al., Isolation of high avidity melanoma-reactive CTL from heterogeneous populations using peptide-MHC tetramers, J. Immunol. 162: 2227-2230 (1999), each of which is incorporated by reference in its entirety. The MHC-peptide multimer may be an MHC class I/antigenic peptide complex or an MHC class II/antigen peptide complex. The antigen peptide may be an autoantigenic peptide or an alloantigen peptide. The antigen peptide is typically an autoimmune disease-associated peptide, a peptide effective at modulating an autoimmune reaction when administered to an individual, or an antigen which prompts an unwanted immune response in the individual. See, e.g., Bluestone, et al., CD127 Expression Inversely Correlates with FoxP3 and Suppressive Functions of $CD4^+$ $T_{regs}$, US Patent Application Publication 2008/0131445, each of which is hereby incorporated by reference in its entirety. As used herein, the term "autoantigen peptide" or "self-antigen" refers to an antigen or epitope which is native to the mammal and which is pathologically immunogenic in the mammal.

An autoantigenic peptide may also be a mimotope peptide capable of complexing with an MHC class II molecule. Mimotope peptides are described in, e.g., Bluestone, et al., CD127 Expression Inversely Correlates with FoxP3 and Suppressive Functions of $CD4^+$ $T_{regs}$, US Patent Application Publication 2008/0131445, which is hereby incorporated by reference in its entirety. As used herein, the term "alloantigen peptide" refers to an antigen or epitope that is a part of an organism's self-recognition system that, when injected into another individual from the same species, triggers an immune response aimed at eliminating it. Exemplary MHC class II molecules/peptide complexes are described in, e.g., Bluestone, et al., CD127 Expression Inversely Correlates with FoxP3 and Suppressive Functions of $CD4^+$ $T_{regs}$, US Patent Application Publication 2008/0131445, which is hereby incorporated by reference in its entirety.

Protocols for using TCR/CD3 activator to expand regulatory T cells from otherwise conventional T cells include the use of autoantigen-specific MHC-peptide tetramers, peptide-pulsed DCs (Yamazaki, et al., J. Exp. Med. 198: 235-247, 2003) or artificial APCs (Maus, et al., Nat. Biotechnol. 20:143-148, 2002) to expand regulatory T cells from individuals independent of the cell surface phenotype. In addition, a combination of in vitro and in vivo approaches can enhance the effects of the therapy. For example, recent studies have shown that administration of self antigens, altered peptide ligands and even non-specific stimuli such as FcR non-binding α-CD3 monoclonal antibodies can promote antigen-specific regulatory T cell activity. See, e.g., Apostolou, et al., J. Exp. Med. 199: 1401-1408 (2003); Belghith, et al., Nat. Med. 9: 1202-1208 (2003), each of which is hereby incorporated by reference in its entirety. Hence, combining in vivo immunization to induce the regulatory T cells with ex vivo expansion or visa versa may be advantageous.

In an embodiment, a stimulatory composition comprises a MHC class I/antigenic peptide complex, particularly an aggregate of such MHC/peptide complexes. In aspects of this embodiment, a stimulatory composition comprises a MHC class I/alloantigen peptide complex or a MHC class I/antigenic peptide complex. In another embodiment, a stimulatory composition comprises a MHC class II/antigenic peptide complex, particularly an aggregate of such MHC/peptide complexes. In aspects of this embodiment, a stimulatory composition comprises a MHC class II/alloantigen peptide complex or a MHC class II/antigenic peptide complex. Numerous applicable methods are known in the art for generating functional MHC class I/peptide and MHC class II/peptide complexes.

A TCR co-stimulator activator is a multivalent antibody or ligand specific for a TCR co-stimulator, such as, e.g., CD28, GITR, B7-1/2, CD5, ICOS, OX40 or CD40. See, e.g., Shimizu et al., Stimulation of CD25(+)CD4(+) regulatory T cells through GITR breaks immunological self-tolerance, Nat. Immunol. 3(2): 135-142 (2002); Tone et al., Mouse glucocorticoid-induced tumor necrosis factor receptor ligand is co-stimulatory for T cells, Proc. Natl. Acad. Sci. USA. 100(25): 15059-15064 (2003), each of which is hereby incorporated by reference in its entirety. A co-stimulatory agent may be an agonist antibody, such as an agonist antibody which binds to CD28, GITR, B7-12, CD5, ICOS, OX40 or CD40.

A second regulatory T cell stimulatory agent is a cytokine, such as, e.g., hepatocyte growth factor, granulocyte colony stimulating factor, interleukins such as, e.g., IL-2, IL-6, IL-7, IL-13, and IL-15. An effective amount is typically between about 200 to about 2500 IU/mL.

In an embodiment, expanding a subpopulation of T-cells comprising a desired biomarker expression pattern can be accomplished by contacting the subpopulation of T-cells with an antigen. In an aspect of this embodiment, a subpopulation of T-cells comprising a desired biomarker expression pattern can be accomplished by contacting the population of cells with an antigen-specific regulatory T cell stimulatory composition. In another aspect of this embodiment, the stimulatory composition comprises an MHC class II/autoantigenic peptide complex. In yet another aspect this embodiment, a subpopulation of T-cells comprising a desired biomarker expression pattern can be accomplished by contacting the population of cells with an antigen-specific regulatory T cell stimulatory composition and another stimulatory agent or a second regulatory T cell stimulatory agent.

In yet another embodiment, expanding a subpopulation of T-cells comprising a desired biomarker expression pattern can be accomplished by contacting the subpopulation of T-cells with an agonist antibody. In an aspect of this embodiment, the agonist antibody is an α-CD3 antibody or an α-CD28 antibody.

In still another embodiment, expanding a subpopulation of T-cells comprising a desired biomarker expression pattern can be accomplished by contacting the subpopulation of T-cells with an agonist antibody and a second stimulating agent. In an aspect of this embodiment, the second stimulatory agent is a cytokine. In aspects of this embodiment, the cytokine is an interleukin, such as, e.g., an IL-2. In an aspect of this embodiment, expanding a subpopulation of T-cells comprising a desired biomarker expression pattern can be accomplished by contacting the subpopulation of T-cells with an α-CD3 antibody or an α-CD28 antibody, and IL-2 in the presence of TGFβ or rapamycin.

Optimal concentrations of each component of the stimulatory compositions, culture conditions and duration can be determined empirically using routine experimentation. Maximal expansions are determined empirically and will vary by, e.g., cell type, incubation conditions. In aspects of this embodiment, maximal expansion a subpopulation of T-cells comprising a desired biomarker expression pattern may be, e.g., at least 50-fold, at least 100-fold, at least 200-fold, at least 300-fold, at least 500-fold or at least 800-fold.

Aspects of the present specification disclose, in part, a method of treating an immune-based disorder in an individual. In one embodiment, the method disclosed herein is an adoptive cellular immunotherapy.

In another embodiment, the method disclosed herein comprises obtaining a biological sample, the biological sample comprising a population of individual-compatible T-cells; screening a sample comprising a population of T-cells to detect a level of cellular expression of a CD6 biomarker; isolating a subpopulation of T-cells comprising a $CD6^{low/-}$ expression pattern; and administering the subpopulation T-cells with a $CD6^{low/-}$ expression pattern into the individual, thereby treating an immune-based disorder in the individual. In an aspect of this embodiment, the method further comprises expanding the subpopulation of T-cells comprising a $CD6^{low/-}$ expression pattern prior to administering the subpopulation T-cells into the individual.

In another embodiment, the method disclosed herein comprises contacting a sample comprising a population of T-cells with a CD6 biomarker ligand; screening the population of T-cells to detect a level of cellular expression of a CD6 biomarker; isolating a subpopulation of T-cells comprising a $CD6^{low/-}$ expression pattern; and administering the subpopulation T-cells with a $CD6^{low/-}$ expression pattern into the individual, thereby treating an immune-based disorder in the individual. In an aspect of this embodiment, the method further comprises expanding the subpopulation of T-cells comprising a $CD6^{low/-}$ expression pattern prior to administering the subpopulation T-cells into the individual.

In yet another embodiment, the method disclosed herein comprises screening a sample comprising a population of T-cells to detect a level of cellular expression of at least two different biomarkers, wherein the at least two different biomarkers include a CD25 biomarker and a CD6 biomarker; isolating a subpopulation of T-cells comprising a $CD25^+ CD6^{low/-}$ expression pattern; and administering the subpopulation T-cells with a $CD25^+ CD6^{low/-}$ expression pattern into the individual, thereby treating an immune-based disorder in the individual. In an aspect of this embodiment, the method further comprises expanding the subpopulation of T-cells comprising a $CD25^+ CD6^{low/-}$ expression pattern prior to administering the subpopulation T-cells into the individual.

In yet another embodiment, the method disclosed herein comprises contacting a sample comprising a population of T-cells with at least two different biomarkers ligands, wherein the at least two different biomarker ligands include a CD25 biomarker ligand and a CD6 biomarker ligand; screening the population of T-cells to detect a level of cellular expression of at two different biomarkers; wherein the at least two different biomarkers include a CD25 biomarker and a CD6 biomarker; isolating a subpopulation of T-cells comprising a $CD25^+ CD6^{low/-}$ expression pattern; and administering the subpopulation T-cells with a $CD25^+ CD6^{low/-}$ expression pattern into the individual, thereby treating an immune-based disorder in the individual. In an aspect of this embodiment, the method further comprises expanding the subpopulation of T-cells comprising a $CD25^+ CD6^{low/-}$ expression pattern prior to administering the subpopulation T-cells into the individual.

In still another embodiment, the method disclosed herein comprises screening a sample comprising a population of T-cells to detect a level of cellular expression of at least two different biomarkers, wherein the at least two different biomarkers include a CD6 biomarker and a CD127 biomarker; isolating a subpopulation of T-cells comprising a $CD6^{low/-} CD127^{low/-}$ expression pattern; and administering the subpopulation T-cells with a $CD6^{low/-} CD127^{low/-}$ expression pattern into the individual, thereby treating an immune-based disorder in the individual. In an aspect of this embodiment, the method further comprises expanding the subpopulation of T-cells comprising a $CD25^+ CD6^{low/-}$ expression pattern prior to administering the subpopulation T-cells into the individual.

In still another embodiment, the method disclosed herein comprises contacting a sample comprising a population of T-cells with at least two different biomarkers ligands, wherein the at least two different biomarker ligands include a CD6 biomarker ligand and a CD127 biomarker ligand; screening the population of T-cells to detect a level of cellular expression of at two different biomarkers; wherein the at least two different biomarkers include a CD6 biomarker and a CD1276 biomarker; isolating a subpopulation of T-cells comprising a $CD6^{low/-} CD127^{low/-}$ expression pattern; and administering the subpopulation T-cells with a $CD6^{low/-} CD127^{low/-}$ expression pattern into the individual, thereby treating an immune-based disorder in the individual. In an aspect of this embodiment, the method further comprises expanding the subpopulation of T-cells comprising a $CD6^{low/-} CD127^{low/-}$ expression pattern prior to administering the subpopulation T-cells into the individual.

In another embodiment, the method disclosed herein comprises screening a sample comprising a population of T-cells to detect a level of cellular expression of at least three different biomarkers, wherein the at least three different biomarkers include a CD4 biomarker, a CD25 biomarker, and a CD6 biomarker; isolating a subpopulation of T-cells comprising a $CD4^+ CD25^+ CD6^{low/-}$ expression pattern; and administering the subpopulation T-cells with a $CD4^+ CD25^+ CD6^{low/-}$ expression pattern into the individual, thereby treating an immune-based disorder in the individual. In an aspect of this embodiment, the method further comprises expanding the subpopulation of T-cells comprising a $CD4^+ CD25^+ CD6^{low/-}$ expression pattern prior to administering the subpopulation T-cells into the individual.

In another embodiment, the method disclosed herein comprises contacting a sample comprising a population of T-cells with at least three different biomarkers ligands, wherein the at least three different biomarker ligands include a CD4 biomarker ligand, a CD25 biomarker ligand, and a CD6 biomarker ligand; screening the population of T-cells to detect a level of cellular expression of at least three different biomarkers; wherein the at least three different biomarkers include a CD4 biomarker, a CD25 biomarker, and a CD6 biomarker; isolating a subpopulation of T-cells comprising a $CD4^+ CD25^+ CD6^{low/-}$ expression pattern; and administering the subpopulation T-cells with a $CD4^+ CD25^+ CD6^{low/-}$ expression pattern into the individual, thereby treating an immune-based disorder in the individual. In an aspect of this embodiment, the method further comprises expanding the subpopulation of T-cells comprising a CD4$^+$ CD25$^+$ CD6$^{low/-}$ expression pattern prior to administering the subpopulation T-cells into the individual.

In yet another embodiment, the method disclosed herein comprises screening a sample comprising a population of T-cells to detect a level of cellular expression of at least three different biomarkers, wherein the at least three different biomarkers include a CD25 biomarker, a CD6 biomarker, and a CD127 biomarker; isolating a subpopulation of T-cells comprising a CD25$^+$ CD6$^{low/-}$ CD127$^{low/-}$ expression pattern; and administering the subpopulation T-cells with a CD25$^+$ CD6$^{low/-}$ CD127$^{low/-}$ expression pattern into the individual, thereby treating an immune-based disorder in the individual. In an aspect of this embodiment, the method further comprises expanding the subpopulation of T-cells comprising a CD25$^+$ CD6$^{low/-}$ CD127$^{low/-}$ expression pattern prior to administering the subpopulation T-cells into the individual.

In yet another embodiment, the method disclosed herein comprises contacting a sample comprising a population of T-cells with at least three different biomarkers ligands, wherein the at least three different biomarker ligands include a CD25 biomarker ligand, a CD6 biomarker ligand, and a CD127 biomarker ligand; screening the population of T-cells to detect a level of cellular expression of at least three different biomarkers; wherein the at least three different biomarkers include a CD25 biomarker, a CD6 biomarker, and a CD127 biomarker; isolating a subpopulation of T-cells comprising a CD25$^+$ CD6$^{low/-}$ CD127$^{low/-}$ expression pattern; and administering the subpopulation T-cells with a CD25$^+$ CD6$^{low/-}$ CD127$^{low/-}$ expression pattern into the individual, thereby treating an immune-based disorder in the individual. In an aspect of this embodiment, the method further comprises expanding the subpopulation of T-cells comprising a CD25$^+$ CD6$^{low/-}$ CD127$^{low/-}$ expression pattern prior to administering the subpopulation T-cells into the individual.

The screening, contacting, isolating, and expanding steps are as described herein. A biological sample obtained comprises a population of individual-compatible T-cells. As used herein, the term "individual-compatible T-cells" refers to cells that can be introduced into the subject, optionally in conjunction with an immunosuppressive therapy, without resulting in extensive chronic graft versus host disease (GvHD). The population of individual-compatible T-cells obtained may comprise antigen or autoantigen-specific regulatory T cells, and may be derived from any source in which antigen or autoantigen-specific regulatory T cells exist, such as peripheral blood, umbilical cord blood, the thymus, lymph nodes, spleen, and bone marrow. A biological sample may be obtained from a healthy individual or an individual suffering or in remission from an immune-based disorder as disclosed herein amenable to therapy as described herein.

In an embodiment, a biological sample comprising a population of individual-compatible cells is obtained from the individual, i.e., autologous cells. In another embodiment, a biological sample comprising a population of individual-compatible cells is obtained from a donor distinct from the individual. The donor is preferably syngeneic, but can also be allogeneic, or even xenogeneic provided the cells obtained are individual-compatible in that they can be introduced into the subject, optionally in conjunction with an immunosuppressive therapy, without resulting in extensive chronic graft versus host disease (GvHD). Allogeneic donor cells are preferably human-leukocyte-antigen (HLA)-compatible, and are typically administered in conjunction with immunosuppressive therapy. To be rendered subject-compatible, xenogenic cells may be subject to gamma irradiation or PEN10 treatment. In certain embodiments, the source of regulatory T cells may be from cadaveric tissue.

A subpopulation T-cells with a desired biomarker expression pattern is administered to an individual. An individual can be any mammal in which modulation of an immune reaction is desired. An individual includes a human, and a human can be a patient. Typically, any individual who is a candidate for a conventional treatment for an immune-based disorder is a candidate for an immune-based disorder treatment disclosed herein. Pre-operative evaluation typically includes routine history and physical examination in addition to thorough informed consent disclosing all relevant risks and benefits of the procedure.

A subpopulation T-cells with a desired biomarker expression pattern is a population of regulatory T cells. In an aspect of this embodiment, a population of regulatory T cells comprises a CD6$^{low/-}$ expression pattern.

In another aspect of this embodiment, a population of regulatory T cells comprises a CD25$^+$ CD6$^{low/-}$ expression pattern. In yet another aspect of this embodiment, a population of regulatory T cells comprises a CD6$^{low/-}$ CD127$^{low/-}$ expression pattern. In still another aspect of this embodiment, a population of regulatory T cells comprises a CD6$^{low/-}$ CD38$^{low/-}$ expression pattern. In another aspect of this embodiment, a population of regulatory T cells comprises a CD6$^{low/-}$ CD49$^{low/-}$ expression pattern.

In another aspect of this embodiment, a population of regulatory T cells comprises a CD4$^+$ CD25$^+$ CD6$^{low/-}$ expression pattern. In yet another aspect of this embodiment, a population of regulatory T cells comprises a CD25$^+$ CD6$^{low/-}$ CD127$^{low/-}$ expression pattern. In still another aspect of this embodiment, a population of regulatory T cells comprises a CD6$^{low/-}$ CD127$^{low/-}$ CD49d$^{low/-}$ expression pattern. In another aspect of this embodiment, a population of regulatory T cells comprises a CD6$^{low/-}$ CD127$^{low/-}$ CD38$^{low/-}$ expression pattern.

In another aspect of this embodiment, a population of regulatory T cells comprises a CD4$^+$ CD25$^+$ CD6$^{low/-}$ CD127$^{low/-}$ expression pattern. In yet another aspect of this embodiment, a population of regulatory T cells comprises a CD4$^+$ CD25$^+$ CD6$^{low/-}$ CD49d$^{low/-}$ expression pattern. In still another aspect of this embodiment, a population of regulatory T cells comprises a CD4$^+$ CD25$^+$ CD6$^{low/-}$ CD38$^{low/-}$ expression pattern. In another aspect of this embodiment, a population of regulatory T cells comprises a CD4$^+$ CD25$^+$ CD6$^{low/-}$ CD45RA$^{low/-}$ expression pattern. In yet another aspect of this embodiment, a population of regulatory T cells comprises a CD25$^+$ CD6$^{low/-}$ CD127$^{low/-}$ CD49d$^{low/-}$ expression pattern. In still another aspect of this embodiment, a population of regulatory T cells comprises a CD25$^+$ CD6$^{low/-}$ CD127$^{low/-}$ CD38$^{low/-}$ expression pattern. In another aspect of this embodiment, a population of regulatory T cells comprises a CD6$^{low/-}$ CD127$^{low/-}$ CD49d$^{low/-}$ CD38$^{low/-}$ expression pattern.

In other aspects of this embodiment, a population of regulatory T cells comprises either a CD6$^{low/-}$ expression pattern, a CD25$^+$ CD6$^{low/-}$ expression pattern, or a CD4$^+$ CD25$^+$ CD6$^{low/-}$ expression pattern further comprise a CD127$^{low/-}$ expression pattern, a CD49d$^{low/-}$ expression pattern, a CD38$^{low/-}$ expression pattern, a CD45RA$^{low/-}$ expression pattern, a HLA-Dr$^+$ expression pattern, a HLA-Dr$^{low/-}$ expression pattern, a FoxP3$^+$ expression pattern, a FoxP3$^{low/-}$ expression pattern, a CTLA-4$^+$ expression pattern, a CTLA-4$^{low/-}$ expression pattern, a GITR$^+$ expression pattern, a GITR$^{low/-}$ expression pattern, a LAG-3$^+$ expression pattern, a LAG-3$^{low/-}$ expression pattern, a CD39$^+$ expression pattern, a CD39$^{low/-}$ expression pattern, a Helios$^+$ expression pattern, a Helios$^{low/-}$ expression pattern, a FcRL3$^+$ expression pattern, a FcRL3$^{low/-}$ expression pattern, a CCR7$^+$ expression pattern, a CCR7$^{low/-}$ expression pattern, a CCR4$^+$ expression pattern, a CCR4$^{low/-}$ expression pattern, a CCR8$^+$ expression pattern, a CCR8$^{low/-}$ expression pattern, a CD62L$^+$ expression pattern, a CD62L$^{low/-}$ expression pattern, a ICOS$^+$ expression pattern, a ICOS$^{low/-}$ expression pattern, a CD103$^+$ expression pattern, a CD103$^{low/-}$ expression pattern, a PD-1$^+$ expression pattern, a PD-1$^{low/-}$ expression pattern, a CD134$^+$ expression pattern, a CD134$^{low/-}$ expression pattern, a GARP$^+$ expression pattern, a GARP$^{low/-}$ expression pattern, a CD45RB$^+$ expression pattern, a CD45RB$^{low/-}$ expression pattern, a CD45RO$^+$ expression pattern, a CD45RO$^{low/-}$ expression pattern, a CD95$^+$ expression pattern, a CD95$^{low/-}$ expression pattern, a CD122$^+$ expression pattern, a CD122$^{low/-}$ expression pattern, a CD147$^{low/-}$ expression pattern, a CD8$^+$ expression pattern, a CD8$^{low/-}$ expression pattern, or any combination thereof.

A regulatory T-cells with a desired biomarker expression pattern is administered to an individual is typically a composition comprising predetermined antigen- or autoantigen-specific regulatory T cells. Such predetermined antigen- or autoantigen-specific regulatory T cells are obtained and expanded using methods disclosed herein from cells preferably specific for a predetermined antigen or autoantigen associated with the targeted allergic or autoimmune reaction. Regulatory T-cells administered to an individual may serve as a "Trojan Horse" to deliver suppressive or other biologic factors to sites of inflammation, such as, e.g., IL-4, stem cell growth factors, angiogenesis regulators, or genetic deficiencies.

An individual is treated for an immune-based disorder. As used herein, the term "immune-based disorder" refers to a condition, disorder, or disease in which an aberrant immune response contributes to the pathogenesis of the immune-based disorder in the individual. An aberrant immune response is any immune reaction in an individual characterized as an unwanted immune or autoimmune response. The disclosed methods of treating are useful in treating a variety of different immune-based disorder in which the modulation of an aberrant immune response in the host is desired. An immune-based disorder includes, without limitation, an autoimmune condition, disorder or disease, a transplant rejection, a graft vs. host disease, a cancer, immune-based inflammatory diseases, and persistent and progressive immune reactions to infectious non self antigens from bacterial, viral, fungal, or parasitic organisms which invade and persist within mammals and humans. Such conditions and disorders include allergies and/or asthma. The allergies and asthma may be due to sensitization with foreign or non-self antigens as pollen, animal dander and food proteins. The source of the provoking foreign antigen can be plant, fungal, mold, or other environmental contaminant. For example, an immune-based disorder can be an autoimmune response and the antigen is an autoantigen, a graft vs. host immune response and the antigen is an autoantigen, an allergy, an asthma, a tissue or organ transplant rejection, or a graft vs. host immune response and the antigen is a purified or unpurified component of the allergen or transplanted tissue or organ provoking the harmful immune response.

Autoimmunity is defined as persistent and progressive immune reactions to non infectious self antigens, as distinct from infectious non self antigens from bacterial, viral, fungal, or parasitic organisms which invade and persist within mammals and humans. An autoimmune response occurs when the immune system of an individual recognizes self-antigens as foreign, leading to the production of self-reactive effector immune cells. Self reactive effector immune cells include cells from a variety of lineages, including, but not limited to, cytotoxic T cells, helper T cells, and B cells. While the precise mechanisms differ, the presence of autoreactive effector immune cells in an individual suffering from an autoimmune disease leads to the destruction of tissues and cells of the individual, resulting in pathologic symptoms. An individual with an autoimmune disease may be diagnosed as known to one of ordinary skill in the art. Such individuals may be identified symptomatically and/or by obtaining a sample from the individual and isolating autoreactive T cells and comparing the level of autoreactive T cells in the individual to a control. See, e.g., US Patent Application Publication 2006/0105336. Numerous assays for determining the presence of such cells in an individual, and therefore the presence of an autoimmune disease, such as an antigen specific autoimmune disease in an individual, are known to those of skill in the art and readily employed in the disclosed methods. Assays of interest include, but are not limited to, those described in, e.g., Autoimmunity 36(6-7): 361-366 (2003); J. Pediatr. Hematol. Oncol. 25 (Suppl 1): S57-S61 (2003); Proteomics 3(11): 2077-2084 (2003); Autoimmun. Rev. 2(1): 43-49 (2003).

Autoimmune condition, disorder or disease can be broadly divided into systemic and organ-specific autoimmune conditions, disorders or diseases, depending on the principal clinico-pathologic features of each disease. A systemic autoimmune condition, disorder or disease include, without limitation, systemic lupus erythematosus (SLE), Sjögren's syndrome, Scleroderma, rheumatoid arthritis and polymyositis. An organ-specific autoimmune condition, disorder or disease may be endocrinologic (Diabetes Mellitus Type 1, Hashimoto's thyroiditis, Addison's disease etc.), dermatologic (*pemphigus vulgaris*, psoriasis, scleroderma), hematologic (autoimmune haemolytic anemia), neural (multiple sclerosis) or can involve virtually any circumscribed mass of body tissue. Autoimmune conditions, disorders or diseases include, without limitation, acute disseminated encephalomyelitis (ADEM), Addison's disease, an allergy or sensitivity, α-phospholipid antibody syndrome (APS), arthritis, autoimmune hemolytic anemia, autoimmune gastritis, autoimmune hepatitis, autoimmune inner ear disease, autoimmune polyendocrinopathy syndrome, autoimmune uveoretinitis, bullous pemphigoid, celiac disease, Chagas disease, chronic obstructive pulmonary disease (COPD), colitis, Crohn's disease, diabetes mellitus type 1 (IDDM), endometriosis, fibromyalgia, Goodpasture's syndrome, Grave's disease, Guillain-Barré syndrome (GBS), Hashimoto's thyroiditis, hidradenitis suppurativa, idiopathic thrombocytopenic purpura, inflammatory bowel disease, interstitial cystitis, lupus (including discoid lupus erythematosus, drug-induced lupus erythematosus, lupus nephritis, neonatal lupus, subacute cutaneous lupus erythematosus and systemic lupus erythematosus), morphea, multiple sclerosis (MS), myasthenia gravis, myopathies, narcolepsy, neuromyotonia, *pemphigus vulgaris*, pernicious anaemia, primary biliary cirrhosis, recurrent disseminated encephalomyelitis (multiphasic disseminated encephalomyelitis), rheumatic fever, schizophrenia, scleroderma, Sjögren's syndrome, tenosynovitis, thyroiditis, vasculitis, and vitiligo. See Pamela D. Van Schaack & Kenneth L. Tong, Treatment of Autoimmune Disorder with a Neurotoxin, US Patent Application Publication 2006/138059, which is hereby incorporated by reference in its entirety. There are numerous, established animal models for using T cell epitopes of autoantigens to induce tolerance, including multiple sclerosis (EAE: experimental autoimmune encephalomyelitis), myasthenia gravis (EMG: experimental myasthenia gravis) and neuritis (EAN: experimental autoimmune neuritis).

Aspects of the present invention provide, in part, a transplant rejection. Transplant rejection occurs when a transplanted organ or tissue is not accepted by the body of the transplant recipient because the immune system of the recipient attacks the transplanted organ or tissue. An adaptive immune response, transplant rejection is mediated through both T cell mediated and humoral immune (antibodies) mechanisms. The number of mismatched alleles determines the speed and magnitude of the rejection response. Different mechanisms tend to act against different transplants.

A transplant rejection can be classified as a hyperacute rejection, an acute rejection, or a chronic rejection. Hyperacute rejection is a complement-mediated response in recipients with pre-existing antibodies to the donor (for example, ABO blood type antibodies). Hyperacute rejection occurs within minutes after the transplant and must be immediately removed to prevent a severe systemic inflammatory response. Rapid agglutination of the blood occurs.

Acute rejection may begin as early as one week after transplantation (as opposed to hyperacute rejection, which is immediate). The risk of acute rejection is highest in the first three months after transplantation. However, acute rejection can also occur months to years after transplantation. The reason that acute rejection usually begins one week after transplantation is that T-cells are involved in the rejection mechanism. These T-cells must differentiate before rejection begins. The T-cells cause cells in the transplanted tissue to lyse, or produce cytokines that cause necrosis of the transplanted tissue. A single episode of acute rejection is not a cause for concern if recognized and treated promptly, and rarely leads to organ failure. Acute rejection occurs to some degree in all transplants (except those between identical twins) unless the immune response in altered through the use of immunosuppressive drugs. It is caused by mismatched HLA, which are present on all cells of the body. There are a large number of different alleles of each HLA, so a perfect match between all HLA in the donor tissue and the recipient's body is extremely rare.

Chronic rejection of a transplanted organ or tissue is where the rejection is due to a poorly understood chronic inflammatory and immune response against the transplanted tissue. Chronic rejection after lung transplantation is the leading cause of long-term morbidity and mortality in lung transplant patients.

Also included in the term "transplant rejection" is a graft-versus-host disease (GVHD). GVHD is a common complication of allogeneic bone marrow transplantation in which functional immune cells in the transplanted marrow recognize the recipient as "foreign" and mount an immunologic attack. It can also take place in a blood transfusion under certain circumstances. GVHD is divided into acute and chronic forms. The acute or fulminant form of the disease (aGVHD) is normally observed within the first 100 days post-transplant, and is a major challenge to transplants owing to associated morbidity and mortality. The chronic form of graft-versus-host-disease (cGVHD) normally occurs after 100 days. The appearance of moderate to severe cases of cGVHD adversely influences long-term survival. Acute and chronic GVHD appear to involve different immune cell subsets, different cytokine profiles, somewhat different host targets, and respond differently to treatment.

Acute GVHD is characterized by selective damage to the liver, skin and mucosa, gastrointestinal tract, immune system (the hematopoietic system, e.g., the bone marrow and the thymus) itself, and the lungs in the form of idiopathic pneumonitis. Acute GVHD of the GI tract can result in severe intestinal inflammation, sloughing of the mucosal membrane, severe diarrhea, abdominal pain, nausea, and vomiting. This is typically diagnosed via intestinal biopsy. Liver GVHD is measured by the bilirubin level in acute patients. Skin GVHD results in a diffuse maculopapular rash, sometimes in a lacy pattern. Acute GVHD is staged as follows: overall grade (skin-liver-gut) with each organ staged individually from a low of 1 to a high of 4. Patients with grade IV GVHD usually have a poor prognosis. If the GVHD is severe and requires intense immunosuppression involving steroids and additional agents to get under control, the patient may develop severe infections as a result of the immunosuppression and may die of infection. Chronic GVHD also attacks the above organs, but over its long-term course can also cause damage to the connective tissue and exocrine glands.

Antigen-specific regulatory T cells disclosed herein may also be used to treat infectious diseases in which the pathogenicity is not a result of the cytopathic effects of the pathogen, but rather the damage caused by the immunoinflammatory response to the infectious agent. For example, regulatory T cells that target expressed viral antigens as disclosed herein can treat a viral-induced immunoinflammatory disease because these T cells can be used to suppress local tissue damage caused by the infection and reduce the inflammation that incites autoimmune disease development. Non-limiting examples of viral-induced immunoinflammatory diseases include hepatitis C, HSV-induced corneal inflammation, Coxsackie-induced pancreatitis, and Coxsackie-induced type 1 diabetes, As used herein, the term "treating," refers to reducing, ameliorating, or eliminating in an individual a clinical symptom of an immune-based disorder; or delaying or preventing in an individual the onset of a clinical symptom of an immune-based disorder. For example, the term "treating" can mean reducing a symptom of a condition characterized by an immune-based disorder by, e.g., at least 20%, at least 30%, at least 40%, at least 50%, at least 60%, at least 70%, at least 80%, at least 90% or at least 100%. Symptoms of immune-based disorders include, without limitation, edema, hyperemia, erythema, bruising, tenderness, stiffness, swollenness, fever, chills, stuffy nose, stuffy head, breathing difficulties, fluid retention, blood clots, loss of appetite, increased heart rate, formation of granulomas, fibrinous, pus, non-viscous serous fluid, ulcer, increased production of self-reactive effector immune cells, inflammation, and pain. The actual symptoms associated with an immune-based disorder are well known and can be determined by a person of ordinary skill in the art by taking into account factors, including, without limitation, the location of the immune-based disorder, the cause of the immune-based disorder, the severity of the immune-based disorder, the tissue or organ affected by the immune-based disorder.

Aspects of the present invention provide, in part, reducing a symptom associated with an autoimmune disorder or transplant rejection. In an aspect of this embodiment, the symptom reduced is inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, infertility or reduced sex drive (low libido), blood sugar changes, and depending on the type of autoimmune disease, an increase in the size of an organ or tissue or, the destruction of an organ or tissue.

Aspects of the present invention provide, in part, reducing a symptom associated with inflammation. In an aspect of this embodiment, the symptom reduced is edema, hyperemia, erythema, bruising, tenderness, stiffness, swollenness, fever, a chill, congestion of the respiratory tract including nose, and bronchi, congestion of a sinus, a breathing problem, fluid retention, a blood clot, a loss of appetite, an increased heart rate, a formation of granulomas, fibrinous, pus, or non-viscous serous fluid, a formation of an ulcer, or pain.

The amount of regulatory T cells disclosed herein used with the methods of treatment disclosed herein will typically be a therapeutically effective amount. As used herein, the term "therapeutically effective amount" is synonymous with "therapeutically effective dose" and refers to the amount of regulatory T cells that will elicit the biological or clinical response being sought by the practitioner in an individual in need thereof. As a non-limiting example, an effective amount is an amount sufficient to reduce a symptom of an immune-based disorder like edema, hyperemia, erythema, bruising, tenderness, stiffness, swollenness, fever, chills, stuffy nose, stuffy head, breathing difficulties, fluid retention, blood clots, loss of appetite, increased heart rate, formation of granulomas, fibrinous, pus, non-viscous serous fluid, ulcer, increased production of self-reactive effector immune cells, inflammation, or pain.

The appropriate effective amount to be administered for a particular application of the disclosed methods can be determined by those skilled in the art, using the guidance provided herein. For example, the effectiveness of regulatory T cells disclosed herein in treating a symptom of a condition characterized by an immune-based disorder can be determined by observing one or more clinical symptoms, and/or physiological indicators associated with the condition. The response of an individual with an immune-based disorder to treatment may be monitored by determining the severity of their symptoms or by determining the frequency of autoreactive T cells in a sample from a individual with an immune-based disorder. The severity of symptoms of the immune-based disorder may correlate with the number of autoreactive T cells. See, e.g., US Patent Application Publication 2006/0105336. In addition, an increase in the number of autoreactive T cells in the sample may be used as an indication to apply treatments intended to minimize the severity of the symptoms and/or treat the immune-based disorder before the symptoms appear. As another example, the effectiveness of regulatory T cells disclosed herein in treating a symptom of a condition characterized by an immune-based disorder can be determined by relying on the clinical experience with existing T-cell infusion therapies. An improvement in an immune-based disorder also can be indicated by a reduced need for a concurrent therapy. Those of skill in the art will know the appropriate symptoms or indicators associated with a specific immune-based disorder and will know how to determine if an individual is a candidate for treatment as disclosed herein. One skilled in the art will recognize that the condition of the individual can be monitored throughout the course of therapy and that the effective amount of a compound or composition disclosed herein that is administered can be adjusted accordingly.

In aspects of this embodiment, a therapeutically effective amount of regulatory T cells disclosed herein reduces a symptom associated with an immune-based disorder by, e.g., at least 10%, at least 20%, at least 30%, at least 40%, at least 50%, at least 60%, at least 70%, at least 80%, at least 90% or at least 100%. In other aspects of this embodiment, a therapeutically effective amount of regulatory T cells disclosed herein reduces a symptom associated with an immune-based disorder by, e.g., at most 10%, at most 20%, at most 30%, at most 40%, at most 50%, at most 60%, at most 70%, at most 80%, at most 90% or at most 100%. In yet other aspects of this embodiment, a therapeutically effective amount of regulatory T cells disclosed herein reduces a symptom associated with an immune-based disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, a therapeutically effective amount of regulatory T cells disclosed herein is the dosage sufficient to reduces a symptom associated with an immune-based disorder for, e.g., at least one week, at least one month, at least two months, at least three months, at least four months, at least five months, at least six months, at least seven months, at least eight months, at least nine months, at least ten months, at least eleven months, or at least twelve months.

In other aspects of this embodiment, a therapeutically effective amount of regulatory T cells disclosed herein is, e.g., about $1 \times 10^7$ cells, about $1 \times 10^8$ cells, about $1 \times 10^9$ cells, about $1 \times 10^{10}$ cells, or about $1 \times 10^{11}$ cells. In yet other aspects of this embodiment, a therapeutically effective amount of regulatory T cells disclosed herein is, e.g., at least $1 \times 10^7$ cells, at least $1 \times 10^8$ cells, at least $1 \times 10^9$ cells, at least $1 \times 10^{10}$ cells, or at least $1 \times 10^{11}$ cells. In still other aspects of this embodiment, a therapeutically effective amount of regulatory T cells disclosed herein is between, e.g., about $1 \times 10^7$ cells to about $1 \times 10^{11}$ cells, about $1 \times 10^8$ cells to about $1 \times 10^{11}$ cells, about $1 \times 10^9$ cells to about $1 \times 10^{11}$ cells, about $1 \times 10^{10}$ cells to about $1 \times 10^{11}$ cells, about $1 \times 10^7$ cells to about $1 \times 10^{10}$ cells, about $1 \times 10^8$ cells to about $1 \times 10^{10}$ cells, about $1 \times 10^9$ cells to about $1 \times 10^{10}$ cells, or about $1 \times 10^8$ cells to about $1 \times 10^9$ cells.

The regulatory T cells disclosed herein can be administered in a variety of ways. By way of a non-limiting example, the cells may be delivered intravenously, or into a body cavity adjacent to the location of an immune response to be suppressed, such as the intraperitoneal cavity, or injected directly within or adjacent to the site of the immune reaction. Intravenous administration, for example, is advantageous in the treatment of many such conditions.

The regulatory T cells disclosed herein may be formulated into medicaments and pharmaceutical compositions using conventional pharmaceutically acceptable parenteral vehicles for administration by injection. These vehicles may be nontoxic and therapeutic, and a number of formulations are set forth in Remington's Pharmaceutical Sciences. Non-limiting examples of excipients are saline, Ringers solution, saline-dextrose solution, and Hank's balanced salt solution. Pharmaceutical compositions may also contain minor amounts of additives such as substances that maintain isotonicity, physiological pH, and stability. The medicaments and compositions comprising regulatory T cells disclosed herein may be in unit dose format. Generally, the unit dose will contain a therapeutically effective amount of regulatory T-cells. The amount will generally depend on the age, size, gender of the patient, the condition to be treated and its severity, the condition of the cells, and their original characteristics as obtained from the donor of the sample. Methods of titrating dosages to identify those which are therapeutically effective are known to persons of ordinary skill in the art. Generally, a therapeutically effective amount of regulatory T cells can be from about $1 \times 10^7$ to about $1 \times 10^{11}$.

Aspects of the present specification disclose, in part, a kit comprising components useful in performing any of the methods disclosed herein.

In one embodiment, a kit comprises components necessary for identifying, isolating, and/or enriching a population of immunosuppressive regulatory T-cells. In an aspect of this embodiment, a kit for identifying and/or isolating a population of immunosuppressive regulatory T-cells comprises a CD6 biomarker ligand.

In another aspect of this embodiment, a kit for identifying, isolating, and/or enriching a population of immunosuppressive regulatory T-cells comprises at least two different biomarker ligands, wherein the at least two different biomarker ligands include a CD25 biomarker ligand and a CD6 biomarker ligand.

In yet another aspect of this embodiment, a kit for identifying, isolating, and/or enriching a population of immunosuppressive regulatory T-cells comprises at least two different biomarker ligands, wherein the at least two different biomarker ligands include a CD6 biomarker ligand and a CD127 biomarker ligand.

In one embodiment, the kits are designed as a one-step staining protocol using whole blood using three different cell surface biomarker ligands. In an aspect of this embodiment, the kit comprises a CD4 biomarker ligand, a CD25 biomarker ligand, and a CD6 biomarker ligand. In another aspect of this embodiment, the kit comprises a CD25 biomarker ligand, a CD6 biomarker ligand, and a CD127 biomarker ligand. In yet another aspect of this embodiment, the kit comprises a CD6 biomarker ligand, a CD127 biomarker ligand, and a CD49d biomarker ligand. In still another aspect of this embodiment, the kit comprises a CD6 biomarker ligand, a CD127 biomarker ligand, and a CD38 biomarker ligand. In another aspect of this embodiment, the kit comprises a CD6 biomarker ligand, a CD49d biomarker ligand, and a CD38 biomarker ligand. In yet another aspect of this embodiment, the kit comprises a FOXPS biomarker ligand as a positive control.

In still another aspect of this embodiment, a kit for identifying, isolating, and/or enriching a population of immunosuppressive regulatory T-cells comprises at least three different biomarker ligands, wherein the at least three different biomarker ligands include a CD4 biomarker ligand, a CD25 biomarker ligand, and a CD6 biomarker ligand.

In still another aspect of this embodiment, a kit for identifying, isolating, and/or enriching a population of immunosuppressive regulatory T-cells comprises at least three different biomarker ligands, wherein the at least three different biomarker ligands include a CD25 biomarker ligand, a CD6 biomarker ligand, and a CD127 biomarker ligand.

In other aspects of this embodiment, a kit for identifying, isolating, and/or enriching a population of immunosuppressive regulatory T-cells as disclosed herein may further include a CD49d biomarker ligand, a CD38 biomarker ligand, a CD45RA biomarker ligand, a HLA-DR biomarker ligand, a FoxP3 biomarker ligand, a CTLA-4 biomarker ligand, a GITR biomarker ligand, a LAG-3 biomarker ligand, a CD39 biomarker ligand, a Helios biomarker ligand, a FcRL3 biomarker ligand, a CCR7 biomarker ligand, a CCR4 biomarker ligand, a CCR8 biomarker ligand, a CD62L biomarker ligand, a ICOS biomarker ligand, a CD103 biomarker ligand, a PD-1 biomarker ligand, a CD134 biomarker ligand, a GARP biomarker, a CD45RB biomarker, a CD45RO biomarker, a CD95 biomarker, a CD122 biomarker, a CD147 biomarker, a CD8 biomarker ligand, or any combination thereof. In yet other aspects of this embodiment, a kit for identifying, isolating, and/or enriching a population of immunosuppressive regulatory T-cells may further include positive and/or negative controls and/or instructions for identifying, isolating, and/or enriching a population of immunosuppressive regulatory T-cells by use of the kit's contents. In another aspect of this embodiment, a kit for identifying, isolating, and/or enriching a population of immunosuppressive regulatory T-cells may further include components necessary for expanding a population of immunosuppressive regulatory T-cells.

In another embodiment, a kit comprises components necessary for expanding a population of immunosuppressive regulatory T-cells. In an aspect of this embodiment, a kit for expanding a population of immunosuppressive regulatory T-cells comprises a stimulatory composition. In aspects of this embodiment, a stimulatory composition comprises an effective amount of an antigen or alloantigen. In other aspects of this embodiment, a stimulatory composition comprises an effective amount of a TCR/CD3 activator. In yet other aspects of this embodiment, a stimulatory composition further comprises a co-stimulatory agent, a second regulatory T cell stimulatory agent, agents that generally promote the survival and/or growth of T cells, or any combination thereof. In another aspect of this embodiment, a kit for expanding a population of immunosuppressive regulatory T-cells comprises a stimulatory composition including an α-CD3 antibody, an α-CD28 antibody, IL-2 or IL-15, and TGFβ or rapamycin. In still other aspects of this embodiment, a kit for expanding a population of immunosuppressive regulatory T-cells may further include positive and/or negative controls and/or instructions for expanding a population of immunosuppressive regulatory T-cells by use of the kit's contents. In still other aspects of this embodiment, a kit for expanding a population of immunosuppressive regulatory T-cells may further include culture containers like dishes or flasks, culture medium, or any necessary buffers, factors, useful to promote cell growth. In yet another aspect, a kit for expanding a population of immunosuppressive regulatory T-cells may further comprises a CD6 biomarker ligand, at least two different biomarker ligands, or at least three different biomarker ligands as disclosed herein.

The disclosed biomarker ligands may be antibodies or ligands and may be labeled or unlabeled. If labeled, the biomarker may be covalently or noncovalently attached with a fluorophore, a quantum dot, a phosphore, a chemiluminescent compound, a bioluminescent compound, a chromogenic compound, an isotope compound like a lanthanide, a radioisotope, an enzyme, a biotin or avidin molecule, or any other label useful for detecting a cell bound by the biomarker. If unlabeled, the kit may further include a label other reagents useful for labeling a biomarker ligand. Methods of attaching labels to antibodies are well known to those of ordinary skill in the art. Particularly preferred labels are those which are attached to the biomarker ligand by a linker which can be readily cleaved or separated or subject to hydrolysis by contact with a predetermined enzyme under physiological conditions. In an aspect of this embodiment, the CD4 biomarker ligand is a fluorescently-labeled anti-CD4 monoclonal antibody, the CD25 biomarker ligand is a fluorescently-labeled anti-CD25 monoclonal antibody, the CD6 biomarker ligand is a fluorescently-labeled anti-CD6 monoclonal antibody, and the CD127 biomarker ligand is a fluorescently-labeled anti-CD127 monoclonal antibody.

The disclosed stimulatory composition may comprise an effective amount of a TCR/CD3 activator that is antigen-specific. The stimulatory composition may further include one or more additional agents, e.g., a co-stimulatory agent, a second regulatory T cell stimulatory agent, or agents that generally promote the survival and/or growth of T cells. A stimulatory composition can be in solution or suspension or immobilized on a solid surface, such as, e.g., a host cell, beads, or other substrate. Cells suitable for use as substrates include artificial antigen-presenting cells (aAPCs). Beads can be plastic, glass, magnetic, or any other suitable material, typically in the 1 µm to 20 µm in diameter range. Stimulatory compositions, TCR/CD3 activators, co-stimulatory agents, second regulatory T cell stimulatory agents, and survival and/or growth promoting factors are as described herein.

Instructions as disclosed herein may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, tape, or CD., on which the information has been recorded. Yet another means that may be present is a website address which may be used via the internet to access the information at a removed site. Any convenient means may be present in the kits.

Aspects of the present specification disclose, in part, a composition comprising a population of immunosuppressive regulatory T-cells obtained according to the methods disclosed herein. In an embodiment, a composition comprising a population of immunosuppressive regulatory T-cells disclosed herein is made according to a method of obtaining a population of immunosuppressive regulatory T-cells as disclosed herein. In another embodiment, a composition comprising a population of immunosuppressive regulatory T-cells disclosed herein is made according to a method of expanding a population of immunosuppressive regulatory T-cells as disclosed herein. In aspects of these embodiments, a population of immunosuppressive regulatory T-cells includes immunosuppressive regulatory T-cells comprising a $CD6^{low/-}$ expression pattern, immunosuppressive regulatory T-cells comprising a $CD25^+$ $CD6^{low/-}$ expression pattern, immunosuppressive regulatory T-cells comprising a $CD6^{low/-}$ $CD127^{low/-}$ expression pattern, immunosuppressive regulatory T-cells comprising a $CD4^+$ $CD25^+$ $CD6^{low/-}$ expression pattern, immunosuppressive regulatory T-cells comprising a $CD25^+$ $CD6^{low/-}$ $CD127^{low/-}$ expression pattern, or immunosuppressive regulatory T-cells comprising a $CD4^+$ $CD25^+$ $CD6^{low/-}$ $CD127^{low/-}$ expression pattern.

In another embodiment, a composition comprising a population of immunosuppressive regulatory T-cells disclosed herein is a pharmaceutical composition. Pharmaceutical compositions may be prepared by combining a therapeutically effective amount of immunosuppressive regulatory T-cells as disclosed herein with conventional acceptable pharmaceutical excipients. A therapeutically effective amount of regulatory T cells typically is disclosed herein and is typically between about $1 \times 10^7$ cells to about $1 \times 10^{11}$ cells. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, or any other dosage form suitable for administration.

In another embodiment, a composition comprising a population of immunosuppressive regulatory T-cells disclosed herein is used in a method of treating an immune-based disorder in an individual as disclosed herein. In yet another embodiment, a composition comprising a population of immunosuppressive regulatory T-cells disclosed herein is used to manufacture a medicament for the treatment of an immune-based disorder as disclosed herein.

Aspects of the present specification disclose, in part, a method of enriching immunosuppressive regulatory T-cells in an individual. In one aspect, the disclosed method comprising administering an α-CD6 antibody to the individual, wherein the administration renders inoperable T-cells comprising a $CD6^{hi/+}$ expression pattern, but not T-cells comprising a $CD6^{low/-}$ expression pattern, thereby enriching for a population of immunosuppressive regulatory T-cells in the individual.

Anti-CD6 antibodies useful to practice the disclosed method are described in, e.g., Starling, et al., Monoclonal Antibodies to Human CD6, U.S. Pat. No. 6,372,215; and Casimiro, et al., Anti-CD6 Monoclonal Antibodies and Their Uses, U.S. Pat. No. 6,572,857, each of which is hereby incorporated by reference in its entirety. An α-CD6 antibody may be any kind of antibody as disclosed herein.

An α-CD6 antibody may be administered using any suitable dosage formulation and route of administration. For example, a composition comprising an α-CD6 antibody may be administered by injection.

The amount of α-CD6 antibody disclosed herein used with the methods of enriching immunosuppressive regulatory T-cells in an individual disclosed herein will typically be a therapeutically effective amount. With reference an α-CD6 antibody administered in an individual to enrich immunosuppressive regulatory T-cells, a therapeutically effective amount refers to the amount of α-CD6 antibody that will elicit the biological or clinical response being sought by the practitioner in an individual in need thereof. As a non-limiting example, an effective amount of an α-CD6 antibody is an amount sufficient to enrich immunosuppressive regulatory T-cells in an individual.

In aspects of this embodiment, a therapeutically effect amount of an α-CD6 antibody is one that one that renders inoperable a population of immunosuppressive regulatory T-cells comprising a $CD6^{hi/+}$ expression pattern by, e.g., at least 20%, at least 30%, at least 40% at least 50%, or at least 60%, at least 70%, at least 80%, or at least 90% as compared to the number of cells comprising a $CD6^{low/-}$ expression pattern in the individual. In other aspects of this embodiment, a therapeutically effect amount of an α-CD6 antibody is one that one that renders inoperable a population of immunosuppressive regulatory T-cells comprising a $CD6^{hi/+}$ expression pattern by, e.g., at least two-fold, at least four-fold, at least eight-fold, at least ten-fold, at least 20-fold, at least 50-fold, or at least 100-fold as compared to the number of cells comprising a $CD6^{low/-}$ expression pattern in the individual.

In aspects of this embodiment, a therapeutically effect amount of an α-CD6 antibody is one that one that enriches a population of immunosuppressive regulatory T-cells comprising a $CD6^{low/-}$ expression pattern by, e.g., at least 20%, at least 30%, at least 40% at least 50%, or at least 60%, at least 70%, at least 80%, or at least 90% as compared to the number of cells comprising a $CD6^{hi/+}$ expression pattern in the individual. In other aspects of this embodiment, a therapeutically effect amount of an α-CD6 antibody is one that one that enriches a population of immunosuppressive regulatory T-cells comprising a $CD6^{low/-}$ expression pattern by, e.g., at least two-fold, at least four-fold, at least eight-fold, at least ten-fold, at least 20-fold, at least 50-fold, or at least 100-fold as compared to the number of cells comprising a $CD6^{hi/+}$ expression pattern in the individual.

Aspects of the present specification may also be described as follows:

1. A method of identifying a population of immunosuppressive regulatory T-cells, the method comprising:
   screening a sample comprising a population of T-cells to detect a level of cellular expression of a CD6 biomarker;
   wherein detection of a subpopulation of T-cells comprising a $CD6^{low/-}$ expression pattern identifies the population of immunosuppressive regulatory T-cells in the sample.

2. A method of identifying a population of immunosuppressive regulatory T-cells, the method comprising:
   contacting a sample comprising a population of T-cells with a CD6 biomarker ligand; and
   screening the population of T-cells to detect a level of cellular expression of a CD6 biomarker;
   wherein detection of a subpopulation of T-cells comprising a $CD4^+$ $CD25^+$ $CD6^{low/-}$ expression pattern identifies the population of immunosuppressive regulatory T-cells in the sample.

3. A method of identifying a population of immunosuppressive regulatory T-cells, the method comprising:
   screening a sample comprising a population of T-cells to detect a level of cellular expression of at least two different biomarkers, wherein the at least two different biomarkers include a CD25 biomarker and a CD6 biomarker;
   wherein detection of a subpopulation of T-cells comprising a $CD25^+$ $CD6^{low/-}$ expression pattern identifies the population of immunosuppressive regulatory T-cells in the sample.

4. A method of identifying a population of immunosuppressive regulatory T-cells, the method comprising:
   contacting a sample comprising a population of T-cells with at least two different biomarkers ligands, wherein the at least two different biomarker ligands include a CD25 biomarker ligand and a CD6 biomarker ligand; and
   screening the population of T-cells to detect a level of cellular expression of at least two different biomarkers;
   wherein the at least two different biomarkers include a CD25 biomarker and a CD6 biomarker;
   wherein detection of a subpopulation of T-cells comprising a $CD25^+$ $CD6^{low/-}$ expression pattern identifies the population of immunosuppressive regulatory T-cells in the sample.

5. A method of identifying a population of immunosuppressive regulatory T-cells, the method comprising:
   screening a sample comprising a population of T-cells to detect a level of cellular expression of at least three different biomarkers, wherein the at least three different biomarkers include a CD4 biomarker, a CD25 biomarker, and a CD6 biomarker;
   wherein detection of a subpopulation of T-cells comprising a $CD4^+$ $CD25^+$ $CD6^{low/-}$ expression pattern identifies the population of immunosuppressive regulatory T-cells in the sample.

6. A method of identifying a population of immunosuppressive regulatory T-cells, the method comprising:
   contacting a sample comprising a population of T-cells with at least three different biomarkers ligands, wherein the at least three different biomarker ligands include a CD4 biomarker ligand, a CD25 biomarker ligand, and a CD6 biomarker ligand; and
   screening the population of T-cells to detect a level of cellular expression of at least three different biomarkers; wherein the at least three different biomarkers include a CD4 biomarker, a CD25 biomarker, and a CD6 biomarker;
   wherein detection of a subpopulation of T-cells comprising a $CD4^+$ $CD25^+$ $CD6^{low/-}$ expression pattern identifies the population of immunosuppressive regulatory T-cells in the sample.

7. The method of embodiments 1-6, wherein the method further comprises isolating or enriching the population of immunosuppressive regulatory T-cells.

8. The method of embodiment 7, wherein the method further comprises expanding the population of immunosuppressive regulatory T-cells with a stimulatory composition.

9. A method of obtaining a population of immunosuppressive regulatory T-cells, the method comprising:
   screening a sample comprising a population of T-cells to detect a level of cellular expression of a CD6 biomarker; and
   isolating a subpopulation of T-cells comprising a $CD6^{low/-}$ expression pattern, thereby obtaining the population of immunosuppressive regulatory T-cells.

10. A method of obtaining a population of immunosuppressive regulatory T-cells, the method comprising:
    contacting a sample comprising a population of T-cells with a CD6 biomarker ligand;
    screening the population of T-cells to detect a level of cellular expression of a CD6 biomarker; and
    isolating a subpopulation of T-cells comprising a $CD6^{low/-}$ expression pattern, thereby obtaining the population of immunosuppressive regulatory T-cells.

11. A method of obtaining a population of immunosuppressive regulatory T-cells, the method comprising:
    screening a sample comprising a population of T-cells to detect a level of cellular expression of at least two different biomarkers, wherein the at least two different biomarkers include a CD25 biomarker and a CD6 biomarker; and
    isolating a subpopulation of T-cells comprising a $CD25^+$ $CD6^{low/-}$ expression pattern, thereby obtaining the population of immunosuppressive regulatory T-cells.

12. A method of obtaining a population of immunosuppressive regulatory T-cells, the method comprising:
    contacting a sample comprising a population of T-cells with at least two different biomarkers ligands, wherein the at least two different biomarker ligands include a CD25 biomarker ligand and a CD6 biomarker ligand;
    screening the population of T-cells to detect a level of cellular expression of at least two different biomarkers; wherein the at least two different biomarkers include a CD25 biomarker and a CD6 biomarker; and isolating a subpopulation of T-cells comprising a CD25$^+$ CD6$^{low/-}$ expression pattern, thereby obtaining the population of immunosuppressive regulatory T-cells.

13. A method of obtaining a population of immunosuppressive regulatory T-cells, the method comprising:
   screening a sample comprising a population of T-cells to detect a level of cellular expression of at least three different biomarkers, wherein the at least three different biomarkers include a CD4 biomarker, a CD25 biomarker, and a CD6 biomarker; and
   isolating a subpopulation of T-cells comprising a CD4$^+$ CD25$^+$ CD6$^{low/-}$ expression pattern, thereby obtaining the population of immunosuppressive regulatory T-cells.

14. A method of obtaining a population of immunosuppressive regulatory T-cells, the method comprising:
   contacting a sample comprising a population of T-cells with at least three different biomarkers ligands, wherein the at least three different biomarker ligands include a CD4 biomarker ligand, a CD25 biomarker ligand, and a CD6 biomarker ligand;
   screening the population of T-cells to detect a level of cellular expression of at least three different biomarkers; wherein the at least three different biomarkers include a CD4 biomarker, a CD25 biomarker, and a CD6 biomarker; and
   isolating a subpopulation of T-cells comprising a CD4$^+$ CD25$^+$ CD6$^{low/-}$ expression pattern, thereby obtaining the population of immunosuppressive regulatory T-cells.

15. The method of embodiments 9-14, wherein the method further comprises expanding the population of immunosuppressive regulatory T-cells.

16. A method of obtaining an expanded population of immunosuppressive regulatory T-cells, the method comprising the steps of:
   screening a sample comprising a population of T-cells to detect a level of cellular expression of a CD6 biomarker;
   isolating a subpopulation of T-cells comprising a CD6$^{low/-}$ expression pattern; and
   contacting the subpopulation of T-cells comprising a CD6$^{low/-}$ expression pattern with a stimulatory composition, thereby obtaining the expanded population of immunosuppressive regulatory T-cells.

17. A method of obtaining an expanded population of immunosuppressive regulatory T-cells, the method comprising the steps of:
   contacting a sample comprising a population of T-cells with a CD6 biomarker ligand; and
   screening the population of T-cells to detect a level of cellular expression a CD6 biomarker;
   isolating a subpopulation of T-cells comprising a CD6$^{low/-}$ expression pattern; and
   contacting the subpopulation of T-cells comprising a CD6$^{low/-}$ expression pattern with a stimulatory composition, thereby obtaining the expanded population of immunosuppressive regulatory T-cells.

18. A method of obtaining an expanded population of immunosuppressive regulatory T-cells, the method comprising the steps of:
   screening a sample comprising a population of T-cells to detect a level of cellular expression of at least two different biomarkers, wherein the at least two different biomarkers include a CD25 biomarker and a CD6 biomarker;
   isolating a subpopulation of T-cells comprising a CD25$^+$ CD6$^{low/-}$ expression pattern; and
   contacting the subpopulation of T-cells comprising a CD25$^+$ CD6$^{low/-}$ expression pattern with a stimulatory composition, thereby obtaining the expanded population of immunosuppressive regulatory T-cells.

19. A method of obtaining an expanded population of immunosuppressive regulatory T-cells, the method comprising the steps of:
   contacting a sample comprising a population of T-cells with at least two different biomarkers ligands, wherein the at least two different biomarker ligands include a CD25 biomarker ligand and a CD6 biomarker ligand; and
   screening the population of T-cells to detect a level of cellular expression of at least two different biomarkers; wherein the at least two different biomarkers include a CD25 biomarker and a CD6 biomarker;
   isolating a subpopulation of T-cells comprising a CD25$^+$ CD6$^{low/-}$ expression pattern; and
   contacting the subpopulation of T-cells comprising a CD25$^+$ CD6$^{low/-}$ expression pattern with a stimulatory composition, thereby obtaining the expanded population of immunosuppressive regulatory T-cells.

20. A method of obtaining an expanded population of immunosuppressive regulatory T-cells, the method comprising the steps of:
   screening a sample comprising a population of T-cells to detect a level of cellular expression of at least three different biomarkers, wherein the at least three different biomarkers include a CD4 biomarker, a CD25 biomarker, and a CD6 biomarker;
   isolating a subpopulation of T-cells comprising a CD4$^+$ CD25$^+$ CD6$^{low/-}$ expression pattern; and
   contacting the subpopulation of T-cells comprising a CD4$^+$ CD25$^+$ CD6$^{low/-}$ expression pattern with a stimulatory composition, thereby obtaining the expanded population of immunosuppressive regulatory T-cells.

21. A method of obtaining an expanded population of immunosuppressive regulatory T-cells, the method comprising the steps of:
   contacting a sample comprising a population of T-cells with at least three different biomarkers ligands, wherein the at least three different biomarker ligands include a CD4 biomarker ligand, a CD25 biomarker ligand, and a CD6 biomarker ligand; and
   screening the population of T-cells to detect a level of cellular expression of at least three different biomarkers; wherein the at least three different biomarkers include a CD4 biomarker, a CD25 biomarker, and a CD6 biomarker;
   isolating a subpopulation of T-cells comprising a CD4$^+$ CD25$^+$ CD6$^{low/-}$ expression pattern; and
   contacting the subpopulation of T-cells comprising a CD4$^+$ CD25$^+$ CD6$^{low/-}$ expression pattern with a stimulatory composition, thereby obtaining the expanded population of immunosuppressive regulatory T-cells.

22. A method of treating an immune-based disorder in an individual, the method comprising:
   obtaining a biological sample, the biological sample comprising a population of individual-compatible T-cells;
   screening a sample comprising a population of T-cells to detect a level of cellular expression of a CD6 biomarker;

isolating a subpopulation of T-cells comprising a CD6$^{low/-}$ expression pattern; and
administering the subpopulation T-cells with a CD6$^{low/-}$ expression pattern into the individual, thereby treating an immune-based disorder in the individual.

23. A method of treating an immune-based disorder in an individual, the method comprising:
obtaining a biological sample, the biological sample comprising a population of individual-compatible T-cells;
contacting a sample comprising a population of T-cells with a CD6 biomarker ligand; and
screening the population of T-cells to detect a level of cellular expression of a CD6 biomarker;
isolating a subpopulation of T-cells comprising a CD6$^{low/-}$ expression pattern; and
administering the subpopulation T-cells with a CD6$^{low/-}$ expression pattern into the individual, thereby treating an immune-based disorder in the individual.

24. A method of treating an immune-based disorder in an individual, the method comprising:
obtaining a biological sample, the biological sample comprising a population of individual-compatible T-cells;
screening a sample comprising a population of T-cells to detect a level of cellular expression of at least two different biomarkers, wherein the at least two different biomarkers include a CD25 biomarker and a CD6 biomarker;
isolating a subpopulation of T-cells comprising a CD25$^+$ CD6$^{low/-}$ expression pattern; and
administering the subpopulation T-cells with a CD25$^+$ CD6$^{low/-}$ expression pattern into the individual, thereby treating an immune-based disorder in the individual.

25. A method of treating an immune-based disorder in an individual, the method comprising:
obtaining a biological sample, the biological sample comprising a population of individual-compatible T-cells;
contacting a sample comprising a population of T-cells with at least two different biomarkers ligands, wherein the at least two different biomarker ligands include a CD25 biomarker ligand and a CD6 biomarker ligand; and
screening the population of T-cells to detect a level of cellular expression of at least two different biomarkers; wherein the at least two different biomarkers include a CD25 biomarker and a CD6 biomarker;
isolating a subpopulation of T-cells comprising a CD25$^+$ CD6$^{low/-}$ expression pattern; and
administering the subpopulation T-cells with a CD25$^+$ CD6$^{low/-}$ expression pattern into the individual, thereby treating an immune-based disorder in the individual.

26. A method of treating an immune-based disorder in an individual, the method comprising:
obtaining a biological sample, the biological sample comprising a population of individual-compatible T-cells;
screening a sample comprising a population of T-cells to detect a level of cellular expression of at least three different biomarkers, wherein the at least three different biomarkers include a CD4 biomarker, a CD25 biomarker, and a CD6 biomarker;
isolating a subpopulation of T-cells comprising a CD4$^+$ CD25$^+$ CD6$^{low/-}$ expression pattern; and
administering the subpopulation T-cells with a CD4$^+$ CD25$^+$ CD6$^{low/-}$ expression pattern into the individual, thereby treating an immune-based disorder in the individual.

27. A method of treating an immune-based disorder in an individual, the method comprising:
obtaining a biological sample, the biological sample comprising a population of individual-compatible T-cells;
contacting a sample comprising a population of T-cells with at least three different biomarkers ligands, wherein the at least three different biomarker ligands include a CD4 biomarker ligand, a CD25 biomarker ligand, and a CD6 biomarker ligand; and
screening the population of T-cells to detect a level of cellular expression of at least three different biomarkers; wherein the at least three different biomarkers include a CD4 biomarker, a CD25 biomarker, and a CD6 biomarker;
isolating a subpopulation of T-cells comprising a CD4$^+$ CD25$^+$ CD6$^{low/-}$ expression pattern; and
administering the subpopulation T-cells with a CD4$^+$ CD25$^+$ CD6$^{low/-}$ expression pattern into the individual, thereby treating an immune-based disorder in the individual.

28. The method of embodiments 22 and 23, wherein the method further comprises expanding the subpopulation T-cells with a CD6$^{low/-}$ expression pattern with a stimulatory composition prior to administering the subpopulation T-cells with a CD6$^{low/-}$ expression pattern into the individual.

29. The method of embodiments 24 and 25, wherein the method further comprises expanding the subpopulation T-cells with a CD25$^+$ CD6$^{low/-}$ expression pattern with a stimulatory composition prior to administering the subpopulation T-cells with a CD25$^+$ CD6$^{low/-}$ expression pattern into the individual.

30. The method of embodiments 26 and 27, wherein the method further comprises expanding the subpopulation T-cells with a CD4$^+$ CD25$^+$ CD6$^{low/-}$ expression pattern with a stimulatory composition prior to administering the subpopulation T-cells with a CD4$^+$ CD25$^+$ CD6$^{low/-}$ expression pattern into the individual.

31. The method of embodiments 8, 16-21, and 28-30, wherein the stimulatory composition comprises a TCR/CD3 activator that is antigen-specific.

32. The method of embodiment 31, wherein the stimulatory composition further comprises a co-stimulatory agent, a second regulatory T cell stimulatory agent, or a T cell survival or growth agent.

33. The method of embodiment 32, wherein the stimulatory composition comprises an α-CD3 antibody, an α-CD28 antibody, IL-2 or IL-15, and TGFβ or rapamycin.

34. The method of embodiments 1-33, wherein the sample is a PBMC sample.

35. The method of embodiments 1-33, wherein the sample is a blood sample, a lymphoid tissue sample, a thymus sample, a pancreas sample, an eye sample, a heart sample, a liver sample, a nerve sample, an intestine sample, a skin sample, a muscle sample, a cartilage sample, or a ligament sample.

36. The method of embodiments 1, 2, 7, 8, 15-17, 22, 23, 28, and 31-35, wherein the CD6 biomarker ligand is a fluorescently-labeled anti-CD6 monoclonal antibody.

37. The method of embodiments 3, 4, 7, 8, 15, 18, 19, 24, 25, 29, and 31-35, wherein the CD25 biomarker ligand is a fluorescently-labeled anti-CD25 monoclonal antibody and the CD6 biomarker ligand is a fluorescently-labeled anti-CD6 monoclonal antibody.

38. The method of embodiments 5-8, 15, 20, 21, 26, 27, and 30-35, wherein the CD4 biomarker ligand is a fluorescently-labeled anti-CD4 monoclonal antibody, the CD25 biomarker ligand is a fluorescently-labeled anti-CD25 monoclonal antibody, and the CD6 biomarker ligand is a fluorescently-labeled anti-CD6 monoclonal antibody.

39. The method of embodiments 1-38, wherein the methods further include a CD127 biomarker ligand, a CD49d biomarker ligand, a CD38 biomarker ligand, a CD45RA biomarker ligand, a HLA-DR biomarker ligand, a FoxP3 biomarker ligand, a CTLA-4 biomarker ligand, a GITR biomarker ligand, a LAG-3 biomarker ligand, a CD39 biomarker ligand, a Helios biomarker ligand, a FcRL3 biomarker ligand, a CCR7 biomarker ligand, a CCR4 biomarker ligand, a CCR8 biomarker ligand, a CD62L biomarker ligand, a ICOS biomarker ligand, a CD103 biomarker ligand, a PD-1 biomarker ligand, a CD134 biomarker ligand, a GARP biomarker ligand, a CD45RB biomarker ligand, a CD45RO biomarker ligand, a CD95 biomarker ligand, a CD122 biomarker ligand, a CD147 biomarker ligand, a CD8 biomarker ligand, or any combination thereof.

40. The method of embodiments 1-39, wherein the methods further include a CD127 biomarker, a CD49d biomarker, a CD38 biomarker, a CD45RA biomarker, a HLA-DR biomarker, a FoxP3 biomarker, a CTLA-4 biomarker, a GITR biomarker, a LAG-3 biomarker, a CD39 biomarker, a Helios biomarker, a FcRL3 biomarker, a CCR7 biomarker, a CCR4 biomarker, a CCR8 biomarker, a CD62L biomarker, a ICOS biomarker, a CD103 biomarker, a PD-1 biomarker, a CD134 biomarker, a GARP biomarker, a CD45RB biomarker, a CD45RO biomarker, a CD95 biomarker, a CD122 biomarker, a CD147 biomarker, a CD8 biomarker, or any combination thereof.

41. The method of embodiments 1-40, wherein the screening step further includes screening the sample comprising a population of T-cells to detect a level of cellular expression of a CD127 biomarker, wherein detection of a subpopulation of T-cells further comprising a CD127$^{low/-}$ expression pattern identifies the population of immunosuppressive regulatory T-cells in the sample.

42. The method of embodiments 1-41, wherein the screening step further includes screening the sample comprising a population of T-cells to detect a level of cellular expression of a CD49d biomarker, wherein detection of a subpopulation of T-cells further comprising a CD49d$^{low/-}$ expression pattern identifies the population of immunosuppressive regulatory T-cells in the sample.

43. The method of embodiments 1-42, wherein the screening step further includes screening the sample comprising a population of T-cells to detect a level of cellular expression of a CD38 biomarker, wherein detection of a subpopulation of T-cells further comprising a CD38$^{low/-}$ expression pattern identifies the population of immunosuppressive regulatory T-cells in the sample.

44. The method of embodiments 1-43, wherein the screening step further includes screening the sample comprising a population of T-cells to detect a level of cellular expression of a CD45RA biomarker, wherein detection of a subpopulation of T-cells further comprising a CD45RA$^{low/-}$ expression pattern identifies the population of immunosuppressive regulatory T-cells in the sample.

45. The method of embodiments 1-44, wherein the screening step further includes screening the sample comprising a population of T-cells to detect a level of cellular expression of a HLA-Dr biomarker, wherein detection of a subpopulation of T-cells further comprising a HLA-Dr$^{+\ or\ low/-}$ expression pattern identifies the population of immunosuppressive regulatory T-cells in the sample.

46. The method of embodiments 1-45, wherein the screening step further includes screening the sample comprising a population of T-cells to detect a level of cellular expression of a FoxP3 biomarker, wherein detection of a subpopulation of T-cells further comprising a FoxP3$^{+\ or\ low/-}$ expression pattern identifies the population of immunosuppressive regulatory T-cells in the sample.

47. The method of embodiments 1-46, wherein the screening step further includes screening the sample comprising a population of T-cells to detect a level of cellular expression of a CTLA-4 biomarker, wherein detection of a subpopulation of T-cells further comprising a CTLA-4$^{+\ or\ low/-}$ expression pattern identifies the population of immunosuppressive regulatory T-cells in the sample.

48. The method of embodiments 1-47, wherein the screening step further includes screening the sample comprising a population of T-cells to detect a level of cellular expression of a GITR biomarker, wherein detection of a subpopulation of T-cells further comprising a GITR$^{+\ or\ low/-}$ expression pattern identifies the population of immunosuppressive regulatory T-cells in the sample.

49. The method of embodiments 1-48, wherein the screening step further includes screening the sample comprising a population of T-cells to detect a level of cellular expression of a LAG-3 biomarker, wherein detection of a subpopulation of T-cells further comprising a LAG-3$^{+\ or\ low/-}$ expression pattern identifies the population of immunosuppressive regulatory T-cells in the sample.

50. The method of embodiments 1-49, wherein the screening step further includes screening the sample comprising a population of T-cells to detect a level of cellular expression of a CD39 biomarker, wherein detection of a subpopulation of T-cells further comprising a CD39$^{+\ or\ low/-}$ expression pattern identifies the population of immunosuppressive regulatory T-cells in the sample.

51. The method of embodiments 1-50, wherein the screening step further includes screening the sample comprising a population of T-cells to detect a level of cellular expression of a Helios biomarker, wherein detection of a subpopulation of T-cells further comprising a Helios$^{+\ or\ low/-}$ expression pattern identifies the population of immunosuppressive regulatory T-cells in the sample.

52. The method of embodiments 1-51, wherein the screening step further includes screening the sample comprising a population of T-cells to detect a level of cellular expression of a FcRL3 biomarker, wherein detection of a subpopulation of T-cells further comprising a FcRL3$^{+\ or\ low/-}$ expression pattern identifies the population of immunosuppressive regulatory T-cells in the sample.

53. The method of embodiments 1-52, wherein the screening step further includes screening the sample comprising a population of T-cells to detect a level of cellular expression of a CCR7 biomarker, wherein detection of a subpopulation of T-cells further comprising a CCR7$^{+\ or\ low/-}$ expression pattern identifies the population of immunosuppressive regulatory T-cells in the sample.

54. The method of embodiments 1-53, wherein the screening step further includes screening the sample comprising a population of T-cells to detect a level of cellular expression of a CCR4 biomarker, wherein detection of a subpopulation of T-cells further comprising a CCR4$^{+\ or\ low/-}$ expression pattern identifies the population of immunosuppressive regulatory T-cells in the sample.

55. The method of embodiments 1-54, wherein the screening step further includes screening the sample comprising a population of T-cells to detect a level of cellular expression of a CCR8 biomarker, wherein detection of a subpopulation of T-cells further comprising a CCR8$^{+\ or\ low/-}$ expression pattern identifies the population of immunosuppressive regulatory T-cells in the sample.
56. The method of embodiments 1-55, wherein the screening step further includes screening the sample comprising a population of T-cells to detect a level of cellular expression of a CD62L biomarker, wherein detection of a subpopulation of T-cells further comprising a CD62L$^{+\ or\ low/-}$ expression pattern identifies the population of immunosuppressive regulatory T-cells in the sample.
57. The method of embodiments 1-56, wherein the screening step further includes screening the sample comprising a population of T-cells to detect a level of cellular expression of a ICOS biomarker, wherein detection of a subpopulation of T-cells further comprising a ICOS$^{+\ or\ low/-}$ expression pattern identifies the population of immunosuppressive regulatory T-cells in the sample.
58. The method of embodiments 1-57, wherein the screening step further includes screening the sample comprising a population of T-cells to detect a level of cellular expression of a CD103 biomarker, wherein detection of a subpopulation of T-cells further comprising a CD103$^{+\ or\ low/-}$ expression pattern identifies the population of immunosuppressive regulatory T-cells in the sample.
59. The method of embodiments 1-58, wherein the screening step further includes screening the sample comprising a population of T-cells to detect a level of cellular expression of a PD-1 biomarker, wherein detection of a subpopulation of T-cells further comprising a PD-1$^{+\ or\ low/-}$ expression pattern identifies the population of immunosuppressive regulatory T-cells in the sample.
60. The method of embodiments 1-59, wherein the screening step further includes screening the sample comprising a population of T-cells to detect a level of cellular expression of a CD134 biomarker, wherein detection of a subpopulation of T-cells further comprising a CD134$^{+\ or\ low/-}$ expression pattern identifies the population of immunosuppressive regulatory T-cells in the sample.
61. The method of embodiments 1-60, wherein the screening step further includes screening the sample comprising a population of T-cells to detect a level of cellular expression of a GARP biomarker, wherein detection of a subpopulation of T-cells further comprising a GARP$^{+\ or\ low/-}$ expression pattern identifies the population of immunosuppressive regulatory T-cells in the sample.
62. The method of embodiments 1-61, wherein the screening step further includes screening the sample comprising a population of T-cells to detect a level of cellular expression of a CD45RB biomarker, wherein detection of a subpopulation of T-cells further comprising a CD45RB$^{+\ or\ low/-}$ expression pattern identifies the population of immunosuppressive regulatory T-cells in the sample.
63. The method of embodiments 1-62, wherein the screening step further includes screening the sample comprising a population of T-cells to detect a level of cellular expression of a CD45RO biomarker, wherein detection of a subpopulation of T-cells further comprising a CD45RO$^{+\ or\ low/-}$ expression pattern identifies the population of immunosuppressive regulatory T-cells in the sample.
64. The method of embodiments 1-63, wherein the screening step further includes screening the sample comprising a population of T-cells to detect a level of cellular expression of a CD95 biomarker, wherein detection of a subpopulation of T-cells further comprising a CD95$^{+\ or\ low/-}$ expression pattern identifies the population of immunosuppressive regulatory T-cells in the sample.
65. The method of embodiments 1-64, wherein the screening step further includes screening the sample comprising a population of T-cells to detect a level of cellular expression of a CD122 biomarker, wherein detection of a subpopulation of T-cells further comprising a CD122$^{+\ or\ low/-}$ expression pattern identifies the population of immunosuppressive regulatory T-cells in the sample.
66. The method of embodiments 1-65, wherein the screening step further includes screening the sample comprising a population of T-cells to detect a level of cellular expression of a CD147 biomarker, wherein detection of a subpopulation of T-cells further comprising a CD147$^{+\ or\ low/-}$ expression pattern identifies the population of immunosuppressive regulatory T-cells in the sample.
67. The method of embodiments 1-66, wherein the screening step further includes screening the sample comprising a population of T-cells to detect a level of cellular expression of a CD8 biomarker, wherein detection of a subpopulation of T-cells further comprising a CD8$^{+\ or\ low/-}$ expression pattern identifies the population of immunosuppressive regulatory T-cells in the sample.
68. A kit for identifying, isolating, and/or enriching a population of immunosuppressive regulatory T-cells, the kit comprising a CD6 biomarker ligand.
69. The kit of embodiment 68, wherein the CD6 biomarker ligand is a fluorescently-labeled anti-CD6 monoclonal antibody.
70. A kit for identifying, isolating, and/or enriching a population of immunosuppressive regulatory T-cells, the kit comprising at least two different biomarker ligands, the at least two different biomarker ligands including a CD25 biomarker ligand and a CD6 biomarker ligand.
71. The kit of embodiment 70, wherein the CD25 biomarker ligand is a fluorescently-labeled anti-CD25 monoclonal antibody, and the CD6 biomarker ligand is a fluorescently-labeled anti-CD6 monoclonal antibody.
72. A kit for identifying, isolating, and/or enriching a population of immunosuppressive regulatory T-cells, the kit comprising at least two different biomarker ligands, the at least two different biomarker ligands including a CD6 biomarker ligand and a CD127 biomarker ligand.
73. The kit of embodiment 72, wherein the CD6 biomarker ligand is a fluorescently-labeled anti-CD6 monoclonal antibody, and the CD127 biomarker ligand is a fluorescently-labeled anti-CD127 monoclonal antibody.
74. A kit for identifying, isolating, and/or enriching a population of immunosuppressive regulatory T-cells, the kit comprising at least three different biomarker ligands, the at least three different biomarker ligands including a CD4 biomarker ligand, a CD25 biomarker ligand, and a CD6 biomarker ligand.
75. The kit of embodiment 74, wherein the CD4 biomarker ligand is a fluorescently-labeled anti-CD4 monoclonal antibody, the CD25 biomarker ligand is a fluorescently-labeled anti-CD25 monoclonal antibody, and the CD6 biomarker ligand is a fluorescently-labeled anti-CD6 monoclonal antibody.
76. A kit for identifying, isolating, and/or enriching a population of immunosuppressive regulatory T-cells, the kit comprising at least three different biomarker ligands, the at least three different biomarker ligands including a CD25 biomarker ligand, a CD6 biomarker ligand, and a CD127 biomarker ligand.

77. The kit of embodiment 76, wherein the CD25 biomarker ligand is a fluorescently-labeled anti-CD25 monoclonal antibody, the CD6 biomarker ligand is a fluorescently-labeled anti-CD6 monoclonal antibody, and the CD127 biomarker ligand is a fluorescently-labeled anti-CD127 monoclonal antibody.

78. The kit of embodiments 68-77, wherein the kit further include a CD49d biomarker ligand, a CD38 biomarker ligand, a CD45RA biomarker ligand, a HLA-DR biomarker ligand, a FoxP3 biomarker ligand, a CTLA-4 biomarker ligand, a GITR biomarker ligand, a LAG-3 biomarker ligand, a CD39 biomarker ligand, a Helios biomarker ligand, a FcRL3 biomarker ligand, a CCR7 biomarker ligand, a CCR4 biomarker ligand, a CCR8 biomarker ligand, a CD62L biomarker ligand, a ICOS biomarker ligand, a CD103 biomarker ligand, a PD-1 biomarker ligand, a CD134 biomarker ligand, a GARP biomarker ligand, a CD45RB biomarker ligand, a CD45RO biomarker ligand, a CD95 biomarker ligand, a CD122 biomarker ligand, a CD147 biomarker ligand, a CD8 biomarker ligand, or any combination thereof.

79. A kit for expanding a population of immunosuppressive regulatory T-cells, the kit comprising a stimulatory composition.

80. The kit of embodiment 79, wherein the stimulatory composition comprises a TCR/CD3 activator that is antigen-specific.

81. The kit of embodiments 79 and 80, wherein the stimulatory composition further comprises a co-stimulatory agent, a second regulatory T cell stimulatory agent, or a T cell survival or growth agent.

82. The kit of embodiments 79, wherein the stimulatory composition comprises an α-CD3 antibody, an α-CD28 antibody, IL-2 or IL-15, and TGFβ or rapamycin.

83. The kit of embodiment 79-82, wherein the kit further comprises a CD6 biomarker ligand or any one of the kit of embodiments 68-79.

84. The kit of embodiment 79-81, wherein the kit further comprises a CD25 biomarker ligand and a CD6 biomarker ligand, or any one of the kit of embodiments 68-79.

85. The kit of embodiment 79-81, wherein the kit further comprises a CD6 biomarker ligand and a CD127 biomarker ligand, or any one of the kit of embodiments 68-79.

86. The kit of embodiment 79-81, wherein the kit further comprises a CD4 biomarker ligand, a CD25 biomarker ligand, and a CD6 biomarker ligand, or any one of the kit of embodiments 68-79.

87. The kit of embodiment 79-81, wherein the kit further comprises a CD25 biomarker ligand, a CD6 biomarker ligand, and a CD127 biomarker ligand, or any one of the kit of embodiments 68-79.

88. A composition comprising a population of immunosuppressive regulatory T-cells obtained according to a method of embodiments 7-22 or 31-67.

89. A composition of embodiment 88, wherein the composition is a pharmaceutical composition.

90. A method of enriching immunosuppressive regulatory T-cells in an individual, the method comprising administering an α-CD6 antibody to the individual, wherein the administration renders inoperable T-cells comprising a $CD6^{hi/+}$ expression pattern, but not T-cells comprising a $CD6^{low/-}$ expression pattern, thereby enriching for a population of immunosuppressive regulatory T-cells in the individual.

91. A method of identifying four distinct maturation subsets of immunosuppressive regulatory T-cell populations, the method comprising the steps of
screening a sample comprising a population of T-cells to detect a level of cellular expression of a CD4 biomarker, a CD25 biomarker, a CD6 biomarker, and one additional biomarker, the one additional biomarker being a FoxP3 biomarker, a CD45RA biomarker, a CCR4 biomarker, a CD39 biomarker, or a HLA-Dr biomarker;
wherein detection of the four distinct maturation subsets of immunosuppressive regulatory T-cells is based upon a i) $CD4^+CD25^+CD6^{low/-}CD45RA^+$ expression pattern in conjunction with a $CCR4^{low}$ expression pattern, a $CD39^{low}$ expression pattern, or a $HLA-Dr^{low}$ expression pattern; ii) a $CD4^+CD25^+CD6^{low/-}$ $CD45RA^+$ expression pattern in conjunction with a $CCR4^-$ expression pattern, a $CD39^-$ expression pattern, or a $HLA-Dr^-$ expression pattern; iii) a $CD4^+CD25^{hi/+}$ $CD6^{low/-}$ expression pattern in conjunction with a $CCR4^{hi/+}$ expression pattern, a $CD45RA^-$ expression pattern, a $CD39^{hi/+}$ expression pattern, or a $HLA-Dr^{low/-}$ expression pattern; and iv) a $CD4^+CD25^+CD6^+$ expression pattern in conjunction with $CR4^{hi/+}$ expression pattern, a $CD45RA^-$ expression pattern, a $CD39^{low/-}$ expression pattern, or a $HLA-Dr^{low/-}$ expression pattern.

92. The method of embodiment 91, wherein one of the four distinct maturation subsets of immunosuppressive regulatory T-cell populations is a nave or resting immunosuppressive regulatory T-cell population subset, the nave or resting immunosuppressive regulatory T-cell population subset comprising a $CD4^+CD25^+CD6^{low/-}$ $CD45RA^+$ $CCR4^-$ expression pattern, a $CD4^+CD25^+CD6^{low/-}CD45RA^+CD39^-$ expression pattern, or a $CD4^+CD25^+CD6^{low/-}CD45RA^+HLA-Dr^-$ expression pattern.

93. The method of embodiment 91 or 92, wherein one of the four distinct maturation subsets of immunosuppressive regulatory T-cell populations is an immature or memory immunosuppressive regulatory T-cell population subset, the immature or memory immunosuppressive regulatory T-cell population subset comprising a $CD4^+CD25^+CD6^{low/-}CD45RA^+CCR4^{low}$ expression pattern, a $CD4^+CD25^+CD6^{low/-}CD45RA^+CD39^{low}$ expression pattern, or a $CD4^+CD25^+CD6^{low/-}CD45RA^+HLA-Dr^{low}$ expression pattern.

94. The method of embodiments 91-93, wherein one of the four distinct maturation subsets of immunosuppressive regulatory T-cell populations is a mature or effector immunosuppressive regulatory T-cell population subset, the mature or effector immunosuppressive regulatory T-cell population subset comprising a $CD4^+CD25^{hi/+}CD6^{low/-}$ $CCR4^{hi/+}$ expression pattern, a $CD4^+CD25^{hi/+}CD6^{low/-}CD45RA^-$ expression pattern, a $CD4^+CD25^{hi/+}CD6^{low/-}CD39^{hi/+}$ expression pattern, a $CD4^+CD25^{hi/+}CD6^{low/-}CCR4^{hi/+}CD45RA^-$ expression pattern, a $CD4^+CD25^{hi/+}CD6^{low/-}$ $CCR4^{hi/+}CD39^{hi/+}$ expression pattern, or a $CD4^+CD25^{hi/+}CD6^{low/-}CCR4^{hi/+}HLA-DR^{low}$ expression pattern.

95. The method of embodiments 91-94, wherein one of the four distinct maturation subsets of immunosuppressive regulatory T-cell populations is a terminal differentiated immunosuppressive regulatory T-cell population subset, the terminal differentiated immunosuppressive regulatory T-cell population subset comprising a CD4$^+$CD25$^{hi/+}$CD6$^{hi/+}$CCR4$^{hi/+}$ expression pattern, a CD4$^+$CD25$^{hi/+}$CD6$^{hi/+}$CD45RA$^-$ expression pattern, a CD4$^+$CD25$^{hi/+}$CD6$^{hi/+}$CD39$^{low}$ expression pattern, a CD4$^+$CD25$^{hi/+}$CD6$^{hi/+}$HLA-Dr$^{low}$ expression pattern, a CD4$^+$CD25$^{hi/+}$CD6$^{hi/+}$CCR4$^{hi/+}$CD45RA$^-$ expression pattern, a CD4$^+$CD25$^{hi/+}$CD6$^{hi/+}$CCR4$^{hi/+}$CD39$^{low}$ expression pattern, or a CD4$^+$CD25$^{hi/+}$CD6$^{hi/+}$CCR4$^{hi/+}$HLA-DR$^{low}$ expression pattern.

96. A method of identifying four distinct maturation subsets of immunosuppressive regulatory T-cell populations, the method comprising the steps of
    screening a sample comprising a population of T-cells to detect a level of cellular expression of a CD4 biomarker, a CD25 biomarker, a CD127 biomarker, and one additional biomarker, the one additional biomarker being a FoxP3 biomarker, a CD45RA biomarker, a CCR4 biomarker, a CD39 biomarker, or a HLA-Dr biomarker;
    wherein detection of the four distinct maturation subsets of immunosuppressive regulatory T-cells is based upon a i) CD4$^+$CD25$^+$CD127$^{low/-}$CD45RA$^+$ expression pattern in conjunction with a CCR4$^{low}$ expression pattern, a CD39$^{low}$ expression pattern, or a HLA-Dr$^{low}$ expression pattern; ii) a CD4$^+$CD25$^+$CD127$^{low/-}$CD45RA$^+$ expression pattern in conjunction with a CCR4$^-$ expression pattern, a CD39$^-$ expression pattern, or a HLA-Dr$^-$ expression pattern; iii) a CD4$^+$CD25$^{hi/+}$CD127$^{low/-}$ expression pattern in conjunction with a CCR4$^{hi/+}$ expression pattern, a CD45RA$^-$ expression pattern, a CD39$^{hi/+}$ expression pattern, or a HLA-Dr$^{low/-}$ expression pattern; and iv) a CD4$^+$CD25$^+$CD127$^+$ expression pattern in conjunction with CR4$^{hi/+}$ expression pattern, a CD45RA$^-$ expression pattern, a CD39$^{low/-}$ expression pattern, or a HLA-Dr$^{low/-}$ expression pattern.

97. The method of embodiment 96, wherein one of the four distinct maturation subsets of immunosuppressive regulatory T-cell populations is a naïve or resting immunosuppressive regulatory T-cell population subset, the a naïve or resting immunosuppressive regulatory T-cell population subset comprising a CD4$^+$CD25$^+$CD127$^{low/-}$CD45RA$^+$CCR4$^-$ expression pattern, a CD4$^+$CD25$^+$CD127$^{low/-}$CD45RA$^+$CD39$^-$ expression pattern, or a CD4$^+$CD25$^+$CD127$^{low/-}$CD45RA$^+$HLA-Dr$^-$ expression pattern.

98. The method of embodiment 96 or 97, wherein one of the four distinct maturation subsets of immunosuppressive regulatory T-cell populations is an immature or memory immunosuppressive regulatory T-cell population subset, the immature or memory immunosuppressive regulatory T-cell population subset comprising a CD4$^+$CD25$^+$CD127$^{low/-}$CD45RA$^+$CCR4$^{low}$ expression pattern, a CD4$^+$CD25$^+$CD127$^{low/-}$CD45RA$^+$CD39$^{low}$ expression pattern, or a CD4$^+$CD25$^+$CD127$^{low/-}$CD45RA$^+$HLA-Dr$^{low}$ expression pattern.

99. The method of embodiments 96-98, wherein one of the four distinct maturation subsets of immunosuppressive regulatory T-cell populations is a mature or effector immunosuppressive regulatory T-cell population subset, the mature or effector immunosuppressive regulatory T-cell population subset comprising a CD4$^+$CD25$^{hi/+}$CD127$^{low/-}$CCR4$^{hi/+}$ expression pattern, a CD4$^+$CD25$^{hi/+}$CD127$^{low/-}$CD45RA$^-$ expression pattern, a CD4$^+$CD25$^{hi/+}$CD127$^{low/-}$CD39$^{hi/+}$ expression pattern, a CD4$^+$CD25$^{hi/+}$CD127$^{low/-}$ CCR4$^{hi/+}$CD45RA$^-$ expression pattern, or a CD4$^+$CD25$^{hi/+}$CD127$^{low/-}$CCR4$^{hi/+}$CD39$^{hi/+}$ expression pattern, or a CD4$^+$CD25$^{hi/+}$CD127$^{low/-}$CCR4$^{hi/+}$HLA-DR$^{low}$ expression pattern.

100. The method of embodiments 96-99, wherein one of the four distinct maturation subsets of immunosuppressive regulatory T-cell populations is a terminal differentiated immunosuppressive regulatory T-cell population subset, the terminal differentiated immunosuppressive regulatory T-cell population subset comprising a CD4$^+$CD25$^{hi/+}$CD127$^{hi/+}$CCR4$^{hi/+}$ expression pattern, a CD4$^+$CD25$^{hi/+}$CD127$^{hi/+}$CD45RA$^-$ expression pattern, a CD4$^+$CD25$^{hi/+}$CD127$^{hi/+}$CD39$^{low}$ expression pattern, a CD4$^+$CD25$^{hi/+}$CD127$^{hi/+}$HLA-Dr$^{low}$ expression pattern, a CD4$^+$CD25$^{hi/+}$CD127$^{hi/+}$CCR4$^{hi/+}$CD45RA$^-$ expression pattern, a CD4$^+$CD25$^{hi/+}$CD127$^{hi/+}$CCR4$^{hi/+}$CD39$^{low}$ expression pattern, or a CD4$^+$CD25$^{hi/+}$CD127$^{low/-}$CCR4$^{hi/+}$HLA-DR$^{low}$ expression pattern.

101. The method of embodiments 91-100, wherein the method further comprises isolating or enriching one or more of the four distinct maturation subsets of immunosuppressive regulatory T-cell populations.

102. The method of embodiments 91-101, wherein the method further comprises expanding the one or more of the four distinct maturation subsets of immunosuppressive regulatory T-cell populations with a stimulatory composition.

103. The method of embodiment 102, wherein the stimulatory composition comprises a TCR/CD3 activator that is antigen-specific.

104. The method of embodiments 102 or 103, wherein the stimulatory composition further comprises a co-stimulatory agent, a second regulatory T cell stimulatory agent, or a T cell survival or growth agent.

105. The method of embodiment 102, wherein the stimulatory composition comprises an α-CD3 antibody, an α-CD28 antibody, IL-2 or IL-15, and TGFβ or rapamycin.

106. The method of embodiments 91-105, wherein the sample is a PBMC sample.

107. The method of embodiments 91-106, wherein the sample is a blood sample, a lymphoid tissue sample, a thymus sample, a pancreas sample, an eye sample, a heart sample, a liver sample, a nerve sample, an intestine sample, a skin sample, a muscle sample, a cartilage sample, or a ligament sample.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of identifying, obtaining, expanding regulatory T cells, the kits comprising components useful in performing any of the methods disclosed herein and the compositions comprising regulatory T cells.

Example 1

CD4+FOXP3+ and CD25+FOXP3+ Cell Populations have Lower CD6 Expression

In order to demonstrate the distribution of CD6 expression in CD4$^+$FOXP3$^+$, CD25$^+$FOXP3$^+$ and CD4$^+$CD25$^+$FOXP3$^+$ regulatory T cells, multicolor flow cytometry analysis was performed to determine the CD6 expression pattern in these cell subsets.

Harvested peripheral blood mononuclear cells (PBMCc) were stained for cell surface expression of CD4, CD25, CD6 and for intracellular stained with FOXP3. Briefly, PBMCs from healthy controls were isolated from heparinized blood by Ficoll gradient centrifugation. About $1-2 \times 10^6$ of harvested PBMC100 µL of 1×PBS-2% Human AB serum (HABS)-1% paraformaldehyde (PFA) were incubated at 4° C. for 20-30 minutes with the following cell surface staining cocktail of monoclonal antibodies: α-CD6-FITC, α-CD4-PC7, and α-CD25-APC. The incubated cells were washed two times with 1×PBS-2% HABS-1% PFA, fixed and permeabilized with Perm/Fix Buffer (eBioscience), washed two times with Perm/Wash Buffer (eBioscience), and then incubated with human IgG at 4° C. for 5 minutes. An intracellular staining cocktail comprising α-FOXP3-Pacific blue clone 206D (BioLegend) monoclonal antibodies were added to these cells, incubated in dark for 60 minutes at room temperature, washed with Perm/Wash Buffer followed by a wash with 1×PBS-2% HABS, and resuspended in 500 µL 1×PBS-2% HABS-1% PFA.

For multicolor flow cytometry analysis, more than 500,000 cells were analyzed using a flow cytometer (GALLIOS™ Flow Cytometer) equipped with 405 nm, 488-nm, and 633-nm lasers and lymphocytes were gated based on forward and side light scatter. Autofluorescence, isotype and FMO controls were used to establish the histogram positions of negative and positive fluorescent events, and the results were expressed as the percentage of cells above the negative region for each monoclonal antibody and/or as the mean of fluorescence intensity (MFI) of discrete populations. Compensation controls were performed using single tube staining with antibodies against human lymphocyte markers conjugated with the fluorochromes used in staining protocols. Negative control for FOXP3 staining was determined by a fluorescence minus one control, isotype control, and/or known negative cell population. Results representative evaluation of two samples. Analysis of collected data was performed using Summit 5.0 or Kaluza 1.1. ModFit software to analyze precursor frequency in proliferative assay was used. For statistical analysis Microsoft Office Excel 2003 and GraphPad Prism 5.01 were used.

The results indicate that CD4 FOXP3 lymphocyte populations show that surface CD6 biomarker expression was about twice low in cells comprising a CD4$^+$FOXP3$^+$ expression pattern as compare with cells comprising a CD4$^+$ FOXP3$^-$ expression pattern (MFI 6.3 vs. 11.6)(FIG. 1A). Similarly, analysis of CD25 FOXP3 lymphocyte populations show that CD6 biomarker expression was twice low in cells comprising a CD4$^+$CD25$^+$FOXP3$^+$ expression pattern as compare with cells comprising a CD4$^+$CD25$^+$FOXP3$^-$ expression pattern (MFI 6.2 vs. 12.5) or CD4$^+$CD25$^-$FOXP3$^-$ expression pattern (MFI 6.2 vs. 11.4) (FIG. 1B).

Human naturally-occurring T regulatory (nT$_{reg}$) have been defined as CD4$^+$FOXP3$^+$, CD4$^+$CD25$^+$ or CD4$^+$CD25$^+$FOXP3$^+$ cells involved in the contact-dependent in vitro suppression. This result indicates that CD4$^+$CD25$^+$FOXP3$^+$ and/or CD4$^+$CD25$^{hi}$FOXP3$^+$ nT$_{reg}$ cells show lower expression of a CD6 biomarker. CD6 negative T cells have been shown to lack the capacity to mount alloreactive responses and considered as anergic cell. Lack of CD6 expression on nT$_{reg}$ cell suggested one mechanism why these regulatory cells are also anergic cells.

Example 2

CD4$^+$CD25$^+$CD6$^{low/-}$ Cell Population Expresses FOXP3

In order to evaluate the expression of FOXP3 marker on CD4/CD25/CD6 subpopulations, multicolor flow cytometry analysis was performed to determine the FOXP3 expression pattern in these regulatory T cell subsets.

Human PBMCs were isolated, harvested and stained for cell surface biomarker expression and intracellular biomarker as described in Example 1. For multicolor flow cytometry analysis, more than 500,000 cells were analyzed using a flow cytometer (GALLIOS™ Flow Cytometer) and lymphocytes were gated based on forward and side light scatter. CD4$^+$ lymphocytes were analyzed in a dotplot for CD6/CD25 expression. FOXP3 expression was analyzed in three CD4$^+$ cell subsets: CD25$^+$CD6$^{low/-}$, CD25$^-$CD6$^{low/-}$ and CD25$^-$CD6$^+$. Negative control for FOXP3 staining was determined by a fluorescence minus one control, isotype control and known negative cell population. Sample size and data analysis were as described in Example 1.

Figure 2:
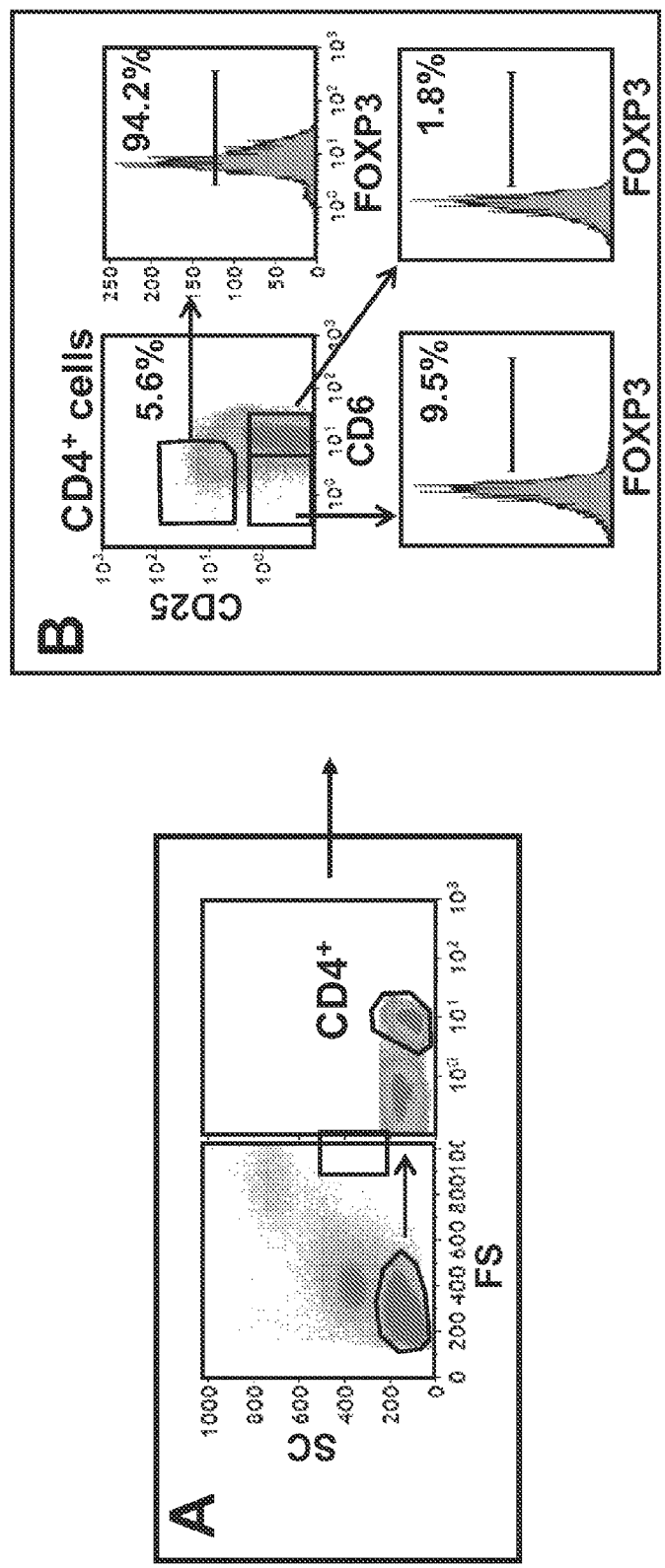
FIG. 2A shows dotplots analyzing CD4$^+$ lymphocytes.
FIG. 2B shows dotplots analyzing CD4$^+$ lymphocytes for CD6/CD25 expression and the expression of FOXP3 on three different CD4$^+$ cell subsets: CD25$^+$CD6$^{low/-}$, CD25$^-$CD6$^{low/-}$ and CD25$^-$CD6$^+$.

The results reveal that 94.2% of lymphocytes comprising a CD4$^+$CD25$^+$CD6$^{low/-}$ expression pattern also express FOXP3 (FIG. 2B). However, only 9.5% of lymphocytes comprising a CD4$^+$CD25$^-$ CD6$^{low/-}$ expression pattern express FOXP3, and only 1.8% of lymphocytes comprising a CD4$^+$CD25$^-$ CD6$^+$ expression pattern express FOXP3 (FIG. 2B). These results indicate that corroborate that FOXP3$^+$ cells are heterogeneous for CD25 biomarker expression, but reveal that regulatory T cells with a CD6$^{low/-}$ expression pattern appear to identify the majority of FOXP3$^+$ nT$_{reg}$ cells.

Example 3

CD25$^+$CD6$^{low/-}$ Cell Population Expresses FOXP3

In order to evaluate the expression of FOXP3 in a lymphocyte CD25$^+$CD6$^{low/-}$ subpopulation, multicolor flow cytometry analysis was performed to determine the FOXP3 expression pattern in these regulatory T cell subsets.

Human PBMCs were isolated, harvested and stained for cell surface biomarker expression and intracellular biomarker as described in Example 1. For multicolor flow cytometry analysis, more than 500,000 cells were analyzed using a flow cytometer (GALLIOS™ Flow Cytometer) and lymphocytes were gated based on forward and side light scatter. CD4$^+$ lymphocytes were analyzed in a dotplot for CD6/CD25 expression. FOXP3 expression was analyzed in three cell subsets: CD25$^+$CD6$^{low/-}$, CD25$^-$CD6$^{low/-}$ and CD25$^-$CD6$^+$. Negative control for FOXP3 staining was determined by a fluorescence minus one control, isotype control and known negative cell population. Sample size and data analysis were as described in Example 1.

Figure 3:
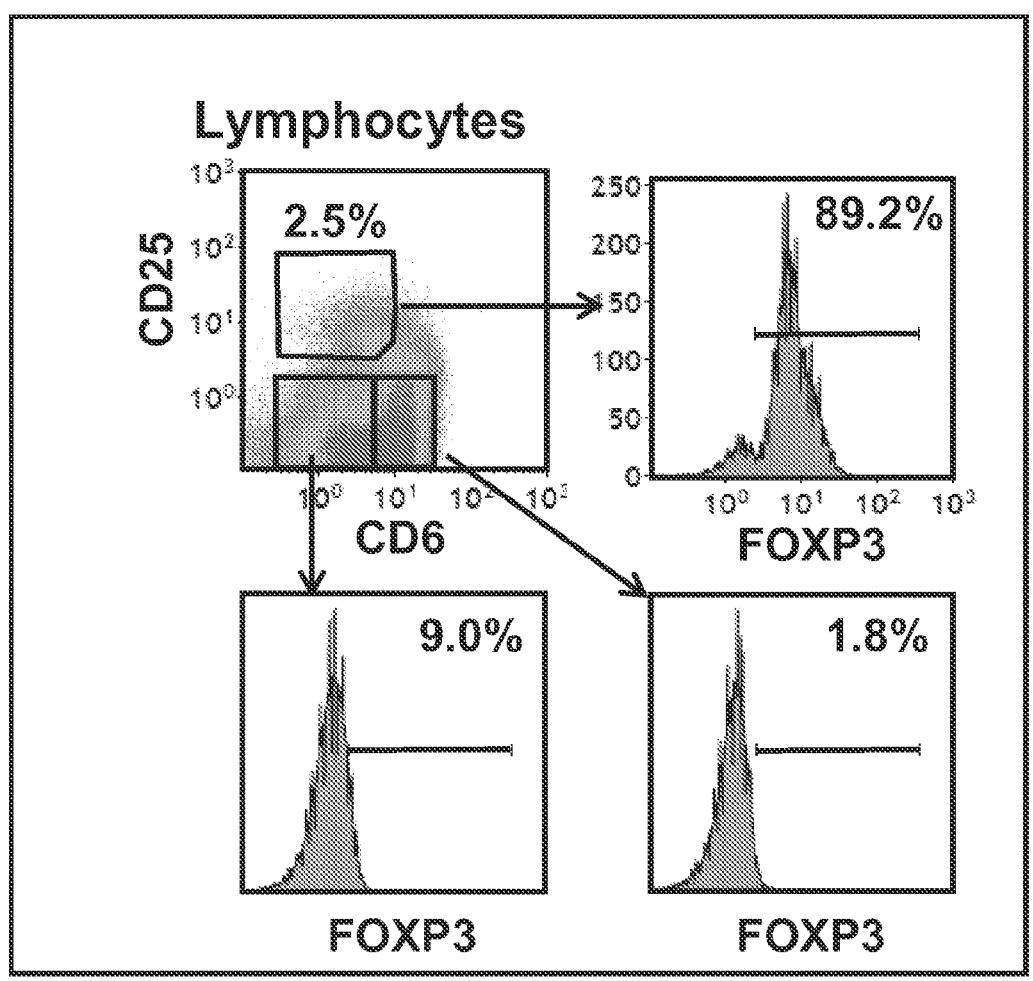
FIG. 3 shows dotplots analyzing lymphocytes for CD6/CD25 expression and the expression of FOXP3 on three different lymphocyte subsets: CD25$^+$CD6$^{low/-}$, CD25$^-$CD6$^{low/-}$ and CD25$^-$CD6$^+$.

The results reveal that 89.2% of lymphocytes comprising a CD25$^+$CD6$^{low/-}$ expression pattern also express FOXP3 (FIG. 3). However, only 9.0% of lymphocytes comprising a CD25$^-$CD6$^{low/-}$ expression pattern express FOXP3, and only 1.8% of lymphocytes comprising a CD25$^-$CD6$^+$ expression pattern express FOXP3 (FIG. 3). This analysis indicates that lymphocytes comprising a CD25$^+$CD6$^{low/-}$ expression pattern included two population subsets, a major population having a high level of expression for FOXP3 (89.2%), and a minor population showing a low or absent FOXP3 expression (10.7%) (FIG. 3). Additionally, these experiments indicated that cells comprising a CD25$^{low/-}$CD6$^+$ expression pattern did not express FOXP3, whereas cells having a CD25$^{low/-}$CD6$^{low/-}$ expression pattern contained a minor subset of cells that also expressed FOXP3 (9.0%) (FIG. 3). These results indicate that FOXP3$^+$ cells are heterogeneous for CD25 biomarker expression, but reveal that regulatory T cells with a CD6$^{low/-}$ expression pattern appear to identify the majority of FOXP3$^+$ nT$_{reg}$ cells.

Example 4

CD6$^{low/-}$ Cell Population Expresses FOXP3

In order to evaluate the effect of CD6 depletion on FOXP3$^+$ cells, multicolor flow cytometry analysis was performed to determine the FOXP3 expression pattern in n CD6$^+$ and CD6$^{low/-}$ cell subsets.

Human PBMCs were isolated, harvested and stained for cell surface biomarker expression and intracellular biomarker as described in Example 1. For multicolor flow cytometry analysis, more than 500,000 cells were analyzed using a flow cytometer (GALLIOS™ Flow Cytometer) and lymphocytes were analyzed in a dotplot for CD6/CD4 expression. FOXP3 expression was analyzed in two cell subsets: PBMC CD6$^{low/-}$ and PBMC CD6$^+$. Negative control for FOXP3 staining was determined by a fluorescence minus one control, isotype control and known negative cell population. Sample size and data analysis were as described in Example 1.

Figure 4:
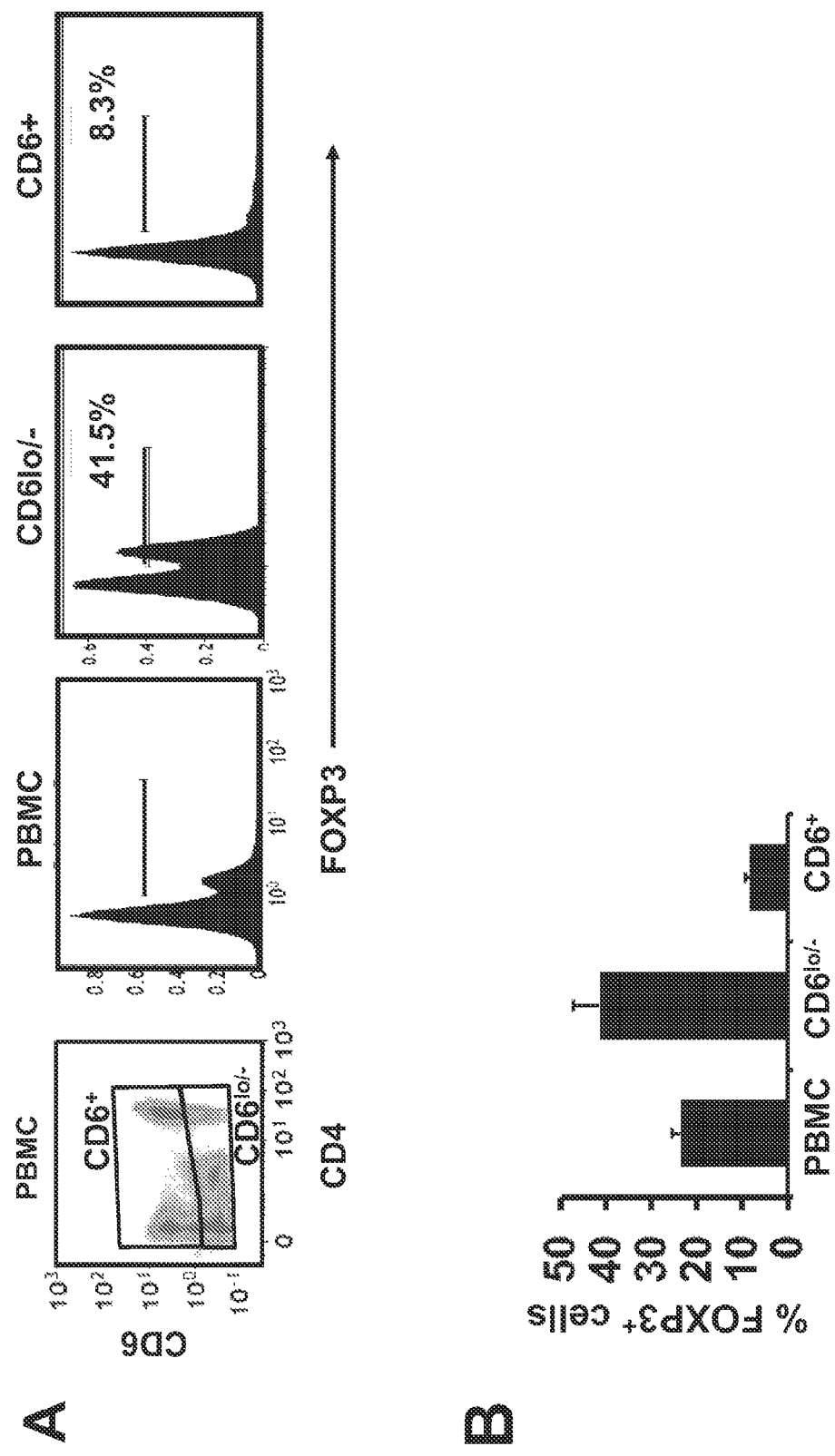
FIG. 4A shows dotplots analyzing PBMC for FOXP3 expression in CD6$^{low/-}$ and CD6$^+$ cell populations.
FIG. 4B shows a graph of % of FOXP3$^+$ cell expression in total PBMC, PBMC CD6$^{low/-}$ and PBMC CD6$^+$ cell populations.

This analysis also showed that lymphocytes comprising a PBMC CD6$^{low/-}$ expression pattern showed a higher level of expression for FOXP3 (41.5%) then lymphocytes comprising a PBMC CD6$^+$ expression pattern (8.3%)(FIG. 4A). These results demonstrated that CD6 depletion in PBMCs can produce a significant enrichment in FOXP3$^+$ nT$_{reg}$ cells.

Example 5

CD4$^+$CD25$^+$CD6$^{low/-}$ CD127$^{low/-}$ Cell Population Shows High Enrichment in FOXP3$^+$ Expression In order to identify more FOXP3 homogeneous CD4$^+$ CD25$^+$ cell population, multicolor flow cytometry analysis was performed to determine the CD6 and CD127 expression pattern in these regulatory T cell subsets.

Human PBMCs were isolated, harvested and stained for cell surface biomarker expression and intracellular biomarker as described in Example 1, except that PBMCs were obtained from four health individuals and α-CD127-PE monoclonal antibodies were added to the cell surface staining cocktail. For multicolor flow cytometry analysis, more than 500,000 cells were analyzed using a flow cytometer (GALLIOS™ Flow Cytometer) and lymphocytes were gated based on forward and side light scatter. CD4$^+$ lymphocytes were analyzed in dotplots for CD4/CD25 expression, CD127/CD25 expression, and CD6/CD25 expression. CD4$^+$CD25$^+$ lymphocytes were analyzed in a dotplot for CD127/CD6 expression. FOXP3 expression was analyzed in the following CD4$^+$ cell subsets: CD25$^+$, CD25$^+$ CD127$^{low/-}$, CD25$^+$CD6$^{low/-}$, CD25$^+$CD6$^{low/-}$CD127$^{low/-}$ and CD25$^+$CD6$^+$CD127$^+$. Negative control for FOXP3 staining was determined by a fluorescence minus one control, isotype control and known negative cell population. Sample size and data analysis were as described in Example 1.

Figure 5:
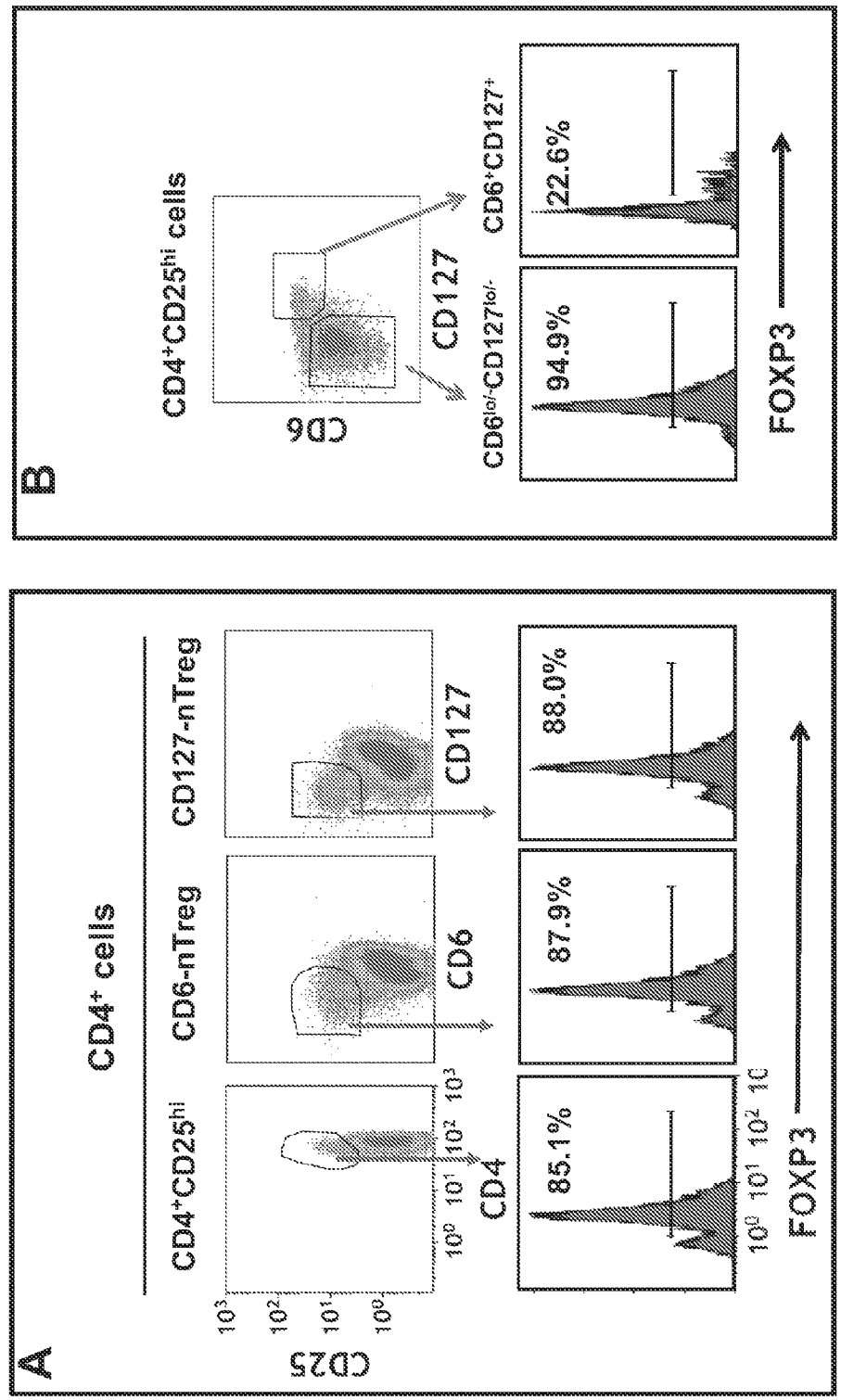
FIG. 5A shows dotplots analyzing lymphocytes for CD25/CD4 expression, CD25/CD6 expression, and CD25/CD127 expression, and expression of FOXP3 on the following CD4$^+$ cell subsets: CD25$^+$, CD25$^+$CD6$^{low/-}$, and CD25$^+$CD127$^{low/-}$.
FIG. 5B shows dotplots analyzing CD4$^+$CD25$^+$ lymphocytes for CD6 and CD127 expression, and expression of FOXP3 on the following CD4$^+$CD25$^+$ cell subsets: CD6$^{low/-}$CD127$^{low/-}$ and CD6$^+$CD127$^+$.
FIG. 5C shows a graph of FOXP3 expression in different nT$_{reg}$ populations defined by different marker combinations. Bar graph shows mean+SD obtained from PBMCs isolated from the peripheral blood of nine different healthy donors. Significant high enrichment of FOXP3$^+$ is observed in CD6$^{lo/-}$CD127$^{lo/-}$ cells compared to CD4$^+$CD25$^{hi}$, CD6-Treg and CD127-Treg populations (p<0.009, U-Mann-Whitney test).
Figure 5:
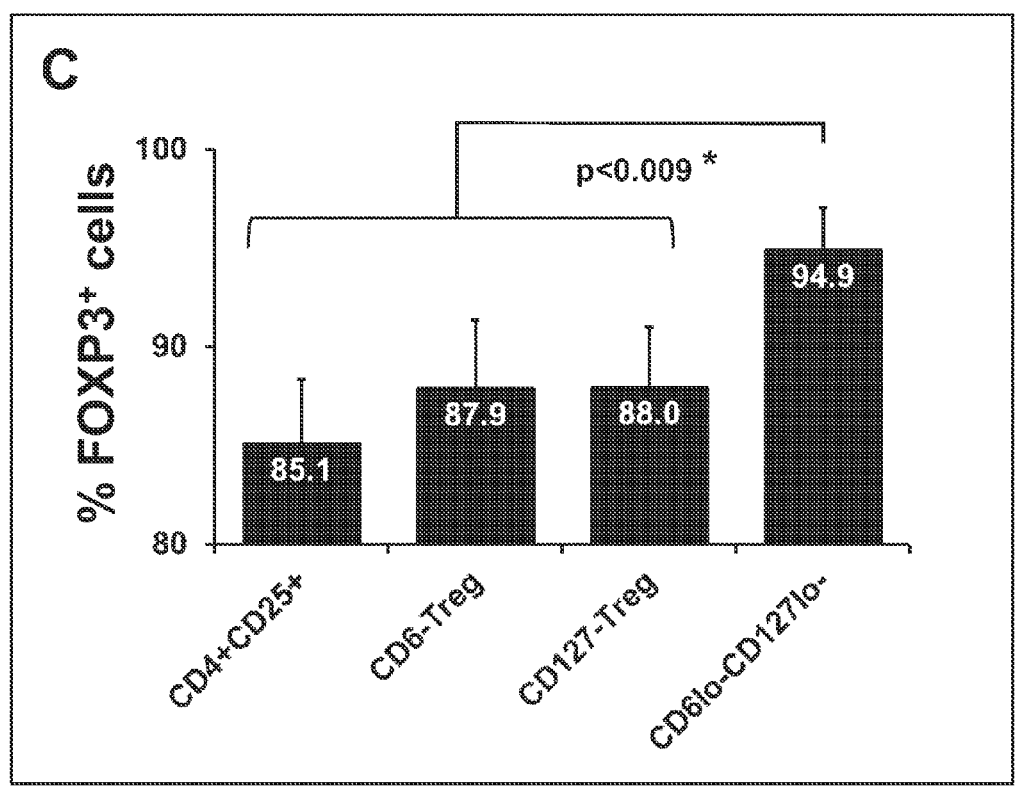

The results indicate that there was no significant difference found in FOXP3 expression between CD4$^+$CD25$^{hi}$ cells (85.1% FOXP3$^+$), CD4$^+$CD6$^{low/-}$ (87.9% FOXP3$^+$) and CD4$^+$CD127$^{low/-}$ cells (88.0% FOXP3$^+$) (FIG. 5A). Strikingly, when CD4$^+$CD25$^{hi}$ cells were analyzed for CD6 and CD127 expression, this analysis revealed that 94.9% of cells comprising a CD4$^+$CD25$^+$CD127$^{low/-}$CD6$^{low/-}$ expression pattern expressed FOXP3 (FIG. 5B), a level comparable to CD4$^+$CD25$^+$CD127$^{low/-}$ cells of which 92.8% expressed FOXP3. Conversely, the CD4$^+$CD25$^{hi}$CD6$^+$ CD127$^+$ cell subset showed low FOXP3 expression (22.6%) (FIG. 5B). Taken together, there was a progressive enrichment in FOXP3$^+$ cells from CD4$^+$CD25$^{hi}$<CD4$^+$CD6$^{low/-}$= CD4$^+$CD127$^{low/-}$<CD4$^+$CD25$^{hi}$CD6$^{lo/-}$CD127$^{lo/-}$ populations (FIG. 5C). Therefore, the combination of CD6 and CD127 surface markers identified a CD4$^+$CD25$^{hi}$ population with the highest enrichment in FOXP3$^+$ cells and these results indicate that a homogeneous FOXP3$^+$ cell population can be identified based on a CD4$^+$CD25$^+$CD127$^{low/-}$ CD6$^{low/-}$ expression pattern.

Example 6

CD4$^+$CD25$^{hi/+}$CD6$^{low/-}$ Cell Population Suppresses T-Cell Activation

In order to demonstrate the suppression function of lymphocyte comprising a CD4$^+$CD25$^{hi/+}$CD6$^{low/-}$ expression pattern, a suppression assay with sorted cells was performed to assess the capacity of added CD4$^+$CD25$^{hi/+}$CD6$^{low/-}$ cells to suppress the proliferation of allogeneic CD8$^+$ responder T-cells using a carboxyfluorescein diacetate succinimidyl ester (CFSE)-based proliferation assay.

Human PBMCs from healthy controls were isolated from heparinized blood by Ficoll gradient centrifugation. About 20-30×10$^6$ of harvested PBMC500 μL of complete cell culture media were incubated at 4° C. for 30 minutes with the following cell surface staining cocktail of monoclonal antibodies: α-CD6-APC, α-CD4-PC7, and α-CD25-PE. The incubated cells were washed two times with 1×PBS and resuspended in complete media to a density of about 10×10$^6$ cells/mL.

For cell sorting using flow cytometry, about 60,000 to 100,000 cells were sorted in complete media using a cell sorter (MOFLO® XDP Cell Sorter) based on a sequential gate definition. Lymphocytes were gated based on forward and side light scatter and doublets were excluded by SSC-H/SSC-W and FSC-H/FSC-W dotplots. CD4$^+$ lymphocytes were analyzed in dotplots for CD25/CD6 expression. Two CD4$^+$ subsets were selected for high speed cell sorting: CD25$^+$CD6$^{low/-}$ (FOXP3$^+$ T$_{reg}$ cells) and CD25$^-$ CD6$^+$ (FOXP3$^-$ non-T$_{reg}$ cells).

Figure 6:
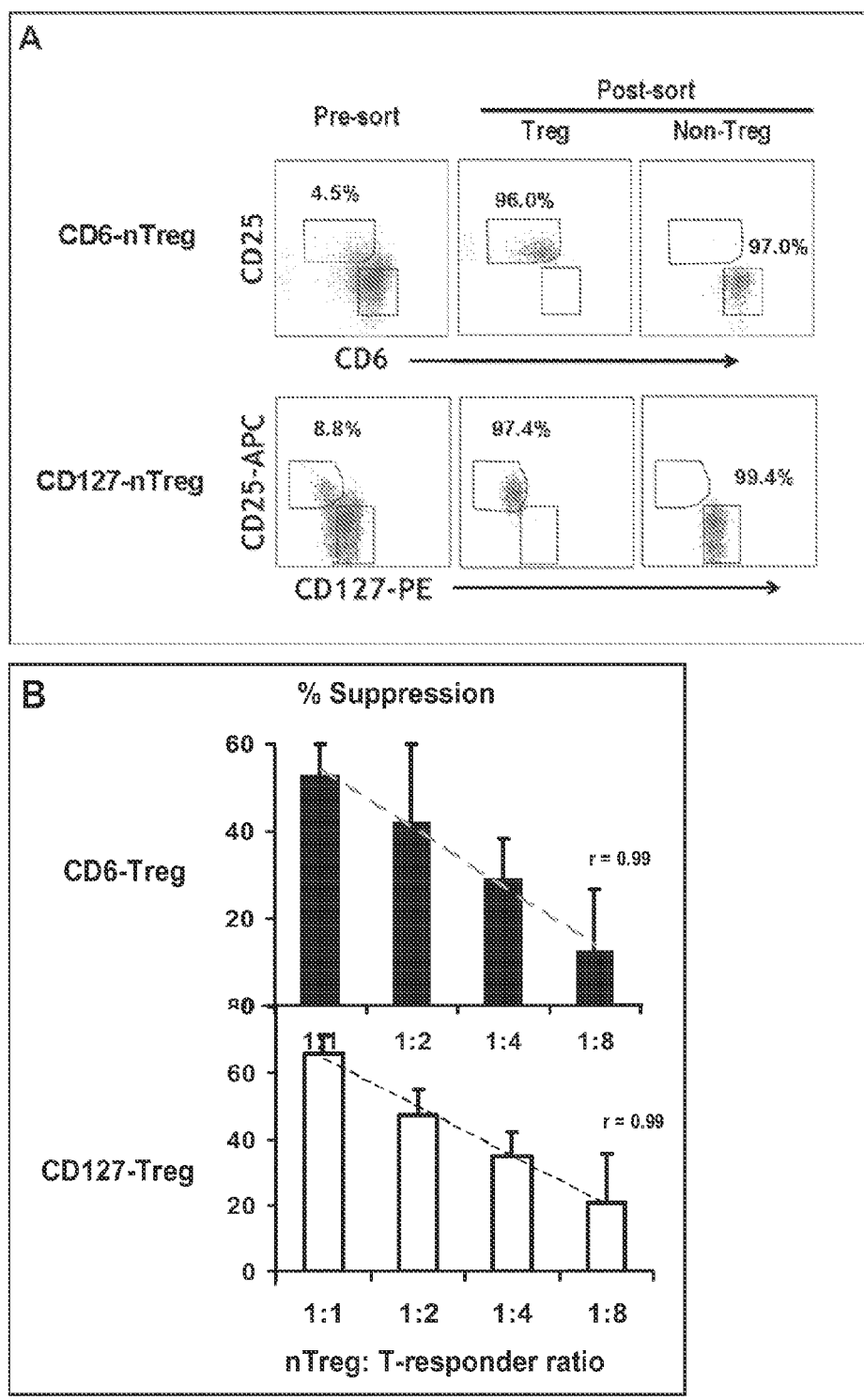
FIG. 6A shows dotplots of a representative results of pre- and post sort cell purity using a CD4$^+$CD25$^+$CD6$^{low/-}$ cell (CD6-nTreg) and CD4$^+$CD25$^+$CD127$^{low/-}$ cell (CD127-nTreg) sorting scheme.
FIG. 6B shows a T$_{reg}$-suppression assay demonstrating that cells comprising a CD4$^+$CD25$^+$CD6$^{low/-}$ expression pattern had a significant (r<0.99) dose-response suppression function on CD8$^+$ T cell proliferation stimulated with α-CD3 and α-CD28 monoclonal antibodies. Percent suppression of precursor frequency (pf) (% suppression=pf sample pf proliferation control×100) is shown. Mean and SD were calculated from four samples in CD4$^+$CD25$^+$CD6$^{lo/-}$ and as positive control of the study nine samples in CD4$^+$CD25$^+$CD127$^{lo/-}$ nTreg-assay experiments.

The results demonstrated that this sorting scheme resulted in the isolation of a CD4$^+$CD25$^+$CD6$^{low/-}$ cell population that was 96% pure (FIG. 6A).

For conducting a T$_{reg}$-suppression assay, 500 μL of 0.6 μM CFSE was added to a 500 μL cell suspension comprising 1-20 million PBMCs, designated T-responder (T$_{resp}$) cells, isolated from a single healthy individual. The cell suspension mixture was incubated at about 20° C. for about 5 minutes, about 1 mL of cold HABS was added, and this mixture was incubated for about 1 minute. After incubation, about 10 mL of 1×PBS was added and this mixture was centrifugation at about 1500 rpm at about 20° C. for about 5 minutes. Cells were resuspended to a density of about 1×10$^6$ cells/mL in complete cell culture media (RMPI 1640, Glutamax-I, 25 mM Hepes, 2.5% human AB serum, sodium pyruvate, 100 U/mL penicillin, 100 μg/mL streptomycin, plus non essential amino acids and 2-mercaptoethanol).

The suppression assay was based on a titration of T$_{reg}$ cell number. About 30,000 to 50,000 total cells were plated in a 96-well plate at the following sorted CD4$^+$CD25$^+$CD6$^{low/-}$ T$_{reg}$ cell to T$_{resp}$ cell ratios: 1:1, 1:2, 1:4, and 1:8. Plated cells were incubated at 37° C. in 5% CO$_2$ atmosphere and 95% humidity for four days. The cells were then stimulated with 0.5 µg/mL soluble α-CD3 and α-CD28 monoclonal antibodies and incubated at 37° C. in 5% $CO_2$ atmosphere and 95% humidity for four days. For harvesting, cells were centrifuged at 750 rpm at about 20° C. for 3 minutes, the media aspirated, and 150 µL of fresh culture media was added to each well. About 4 µL of α-CD8-APC monoclonal antibody was added to each well except in for the "PBMC unstained" control and incubated at 4° C. for 30 minutes in the dark. About 200 µL 1×PBS, 10% HABS was added to each well and 96-well plate was centrifuge at 750 rpm at about 20° C. for 3 minutes, the media aspirated, and about 200 µL 1×PBS, 10% HABS was added to each well. About 5 µL of 7AAD was added to each well to identify viable cells. To analyze $T_{reg}$ cell suppression using flow cytometry, cells were gated based on forward and side light scatter and then cells comprising a $7AAD^+$ expression pattern were excluded and cells comprising a $CD8^+$ expression pattern were analyzed by CFSE staining to evaluate cell proliferation. A sorted non-$T_{reg}$ cell population comprising a $CD4^+CD25^-CD6^+$ expression pattern was used as a negative control in all experiments. A CFSE histogram of unstimulated responder cells defined the parent population, and the proliferation of activated responders was determined by calculation of precursor frequency (pf) using ModFit LT software (Verity Software House, v3.0; Topsham ME). Representative result of three samples evaluated and are expressed as % suppression of pf for each $T_{reg}:T_{resp}$ ratio sample.

The results show that cells comprising a $CD4^+CD25^+CD6^{low/-}$ expression pattern had a dose-response suppression function on $CD8^+$ T cells stimulated with α-CD3 and α-CD28 monoclonal antibodies (FIG. 6B. The maximum suppression (57%) was observed at a 1:1 $T_{reg}:T_{resp}$ ratio. The suppression activity was similar to that of sorted $CD4^+CD25^{hi}CD127^{lo/-}$ cells used as positive control for the assay (FIG. 6B). Sorted $CD4^+CD25^-CD6^+$ or $CD4^+CD25^-CD127^+$ non-$T_{reg}$ cells used as a negative control did not show suppression activity (data not shown). These results indicate that a $CD4^+CD25^+CD6^{low/-}$ cell population contains suppressive regulatory. Taken together, the high expression of FOXP3, characteristic distribution of $T_{reg}$-associated antigens (CD4 and CD25), and suppressor activity in an in vitro functional assay establish concluded that natural regulatory T-suppressor cells show low/negative expression of cell surface CD6 and that the $CD4^+CD25^+CD6^{low/-}$ expression pattern identified regulatory T-cell suppression cells.

Example 7

Characterization of $T_{reg}$-Associated Markers on $CD25^+CD6^{low/-}$ Cell Population In order to determine whether a $CD6^{low/-}$ expression pattern defined a homogeneous or heterogeneous cell population, multicolor flow cytometry analysis was performed using a variety of biomarkers in order to determine whether different biomarker expression pattern were observed in $CD25^+ CD6^{low}$ regulatory T cells.

Human PBMCs were isolated, harvested and stained for cell surface biomarker expression and intracellular biomarker as described in Example 1, except that α-CD45RA-ECD, and α-HLA-Dr-APCA750 monoclonal antibodies were added to the cell surface staining cocktail and α-CTLA-4-PC5 monoclonal antibodies were added to the intracellular staining cocktail. For multicolor flow cytometry analysis, more than 500,000 cells were analyzed using a flow cytometer (GALLIOS™ Flow Cytometer) and lymphocytes were gated based on forward and side light scatter lymphocytes were analyzed in dotplots for CD6/FOXP3 expression. Negative control for FOXP3 staining was determined by a fluorescence minus one control and known negative cell population. In a second round of multicolor flow cytometry analysis, more than 500,000 cells were analyzed. Lymphocytes were gated based on forward and side light scatter and analyzed with CD45RA, HLA-Dr and CTLA-4 $T_{reg}$-associated markers on the basis of CD45RA/FOXP3 expression patterns. Sample size and data analysis were as described in Example 1.

Figure 7:
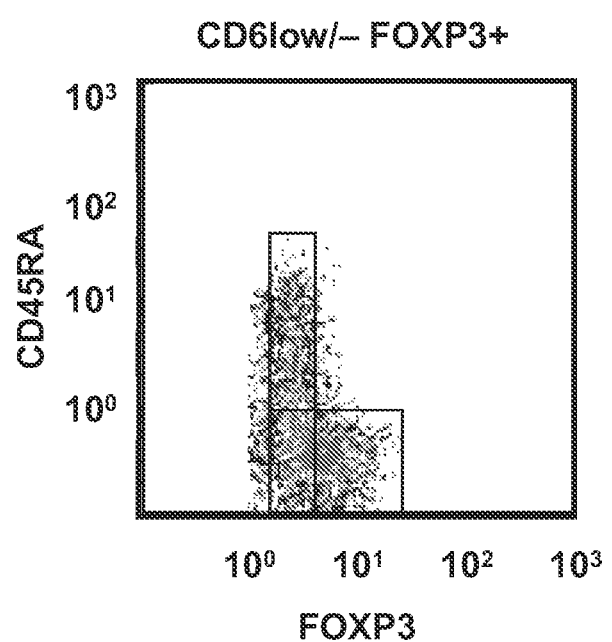
FIG. 7 shows dotplots analyzing CD6$^{low/-}$ FOXP3$^+$ lymphocytes for FOXP3/CD45RA expression.

Results from the analysis of CD6 and FOXP3 expression indicate that three distinct populations of regulatory T cells can be discerned (FIG. 7). About 22.0% of $CD6^{low/-}$ cells are cells that further comprise a $CD45RA^+FOXP3^{low/-}$ expression pattern; about 37.1% of $CD6^{low/-}$ cells are cells that further comprise a $CD45RA^-FOXP3^+$ expression pattern; and about 29.2% of $CD6^{low/-}$ cells are cells that further comprise a $CD45RA^-FOXP3^{low/-}$ expression pattern. Further analysis of these three $CD6^{low/-}$ cell populations using additional biomarkers are shown in Table 1.

TABLE 1

Anaysis of Three $CD6^{low/-}$ Cell Populations

|  | $CD45RA^+$ $FOXP3^{low/-}$ | $CD45RA^-$ $FOXP3^{low/-}$ | $CD45RA^-$ $FOXP3^+$ |
|---|---|---|---|
| $CTLA-4^+$ | 34.0% | 62.1% | 91.7% |
| $HLA-Dr^+$ | 3.1% | 21.8% | 61.6% |
| $CD25^+$ | 100% | 100% | 100% |

Three phenotypic and functional $T_{reg}$ cell subsets were recently proposed, including $CD45RA^+FOXP3^{low}$ resting $T_{reg}$ cells and $CD45RA^-FOXP3^{high}$ activated $T_{reg}$ cells, both with in vitro suppressive functions, and $CD45RA^-FOXP3^{low}$ cytokine-secreting non-suppressive Treg cells. The results using a CD6 biomarker indicate that these three subtypes can be easily identified and isolated.

Example 8

Characterization of $T_{reg}$-Associated Markers on $CD4^+CD25^+CD6^{low/-}$ Cell Population In order to more fully characterize lymphocytes comprising a $CD4^+CD25^+CD6^{low/-}$ expression pattern, multicolor flow cytometry analysis was performed to determine the CD127, CD45A, HLA-Dr, and CLTA-4 expression pattern in these regulatory T cell subsets.

Human PBMCs were isolated, harvested and stained for cell surface biomarker expression and intracellular biomarker as described in Example 1, except that α-CD127-PE, α-CD45RA-ECD, and α-HLA-Dr-APCA750 monoclonal antibodies were added to the cell surface staining cocktail and α-CTLA-4-PC5 monoclonal antibodies were added to the intracellular staining cocktail. For multicolor flow cytometry analysis, between $0.5$-$1.0 \times 10^6$ cells were analyzed using a flow cytometer (GALLIOS™ Flow Cytometer) and lymphocytes were gated based on forward and side light scatter. $CD4^+$ lymphocytes were analyzed in dotplots for CD6/CD25 expression. $CD25^+/CD6^{low/-}$ lymphocytes were analyzed in dotplots for FOXP3, CTLA-4, CD45RA, and HLA-Dr expression. Negative control for FOXP3 staining was determined by a fluorescence minus one control and known negative cell population. Sample size and data analysis were as described in Example 1.

Figure 8:
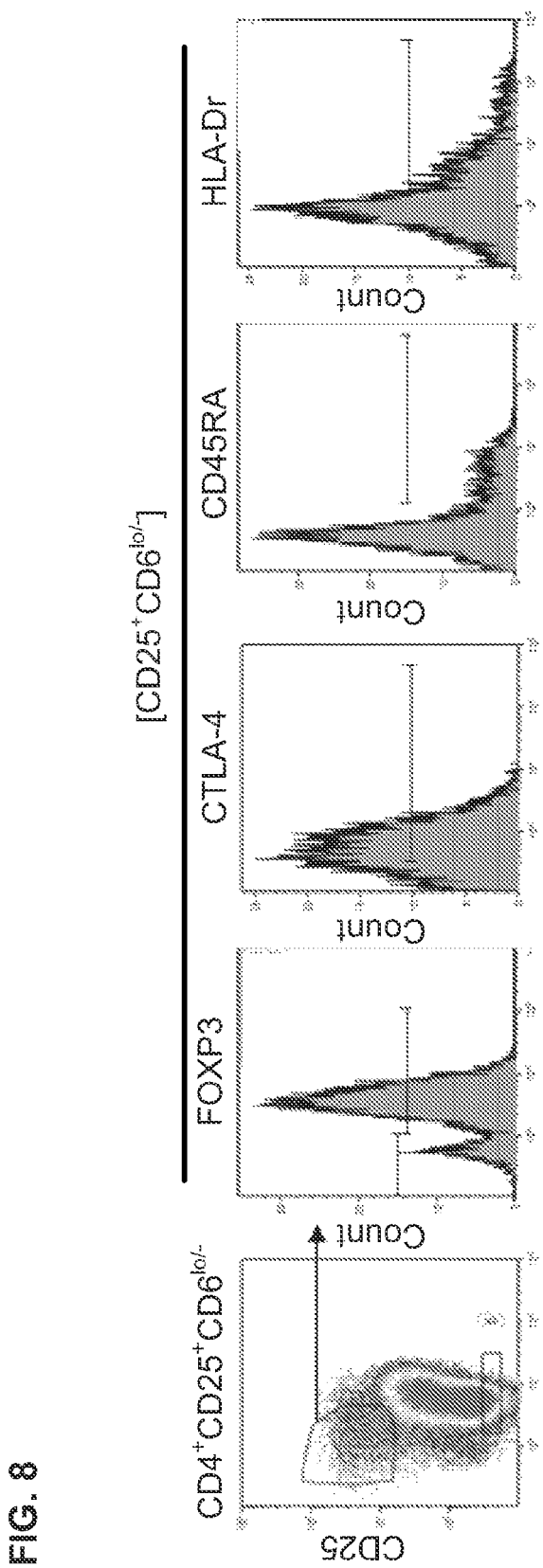
FIG. 8 shows dotplots analyzing CD4$^+$CD25$^+$CD6$^{low/-}$ lymphocytes for FOXP3, CTLA-4, CD45RA, or HLA-Dr expression.

The results show that cells comprising a CD4$^+$CD25$^+$CD6$^{low/-}$ expression pattern expressed different levels of CTLA-4, CD45RA and HLA-Dr. The vast majority of cells (84.5%) comprising a CD25$^+$CD6$^{low/-}$ expression pattern also expressed FOXP3 (FIG. 8). The results also revealed that 62.7% of lymphocytes comprising a CD25$^+$CD6$^{low/-}$ expression pattern also express CTLA-4 (FIG. 8), indicating that two distinct populations of CD25$^+$CD6$^{low/-}$ regulatory T cells exist, a majority population (62.7%) that expresses CTLA-4 and a minority population (37.3%) that does not express this biomarker (FIG. 8). Similarly, two distinct populations of CD25$^+$CD6$^{low/-}$ regulatory T cells were identified based on CD45RA and HLA-Dr biomarkers. For CD45RA, the two distinct populations of CD25$^+$CD6$^{low/-}$ regulatory T cells were a majority population (79.4%) that did not expresses CD45RA and a minority population (20.6%) that did express this biomarker (FIG. 8). For HLA-Dr, the two distinct populations of CD25$^+$CD6$^{low/-}$ regulatory T cells were a majority population (68.0%) that did not expresses HLA-Dr and a minority population (32.0%) that did express this biomarker (FIG. 8). These results indicate that the use of additional biomarkers are useful in identifying distinct subset populations of CD4$^+$CD25$^+$CD6$^{low/-}$ or CD25$^+$CD6$^{low/-}$ regulatory T cells.

Example 9

Comparison of Biomarker Expression of CD4$^+$CD25$^{hi}$CD6$^{lo/-}$ and CD4$^+$CD25$^{hi}$CD127$^{lo/-}$ Populations In order to discern differences between CD4$^+$CD25$^{hi}$CD6$^{lo/-}$ and CD4$^+$CD25$^{hi}$CD127$^{lo/-}$ T$_{reg}$ populations, multicolor flow cytometry analysis was performed using a variety of biomarkers in order to determine whether these regulatory T cell subsets have different biomarker expression pattern.

Human PBMCs were isolated, harvested and stained for cell surface biomarker expression and intracellular biomarker as described in Example 1, except that PBMCs were obtained from five health individuals and cells were stained using one of the following three panels of fluorescently-labeled monoclonal antibodies: 1) Panel 8c (α-CD4-PC7, α-CD25-APC-AF647, α-CD6-FITC, α-CD127-PE, α-CD45RA-ECD, α-HLA-Dr-APC-AF750, α-CTLA-4-PC5, α-FOXP3-Pacific Blue); 2) Panel 10c-1 (α-CD4-Krome Orange, α-CD25-PC7, α-CD6-FITC, α-CD127-APC-CF700, α-CD45RA-APC-AF750, α-CD62L-ECD, α-CD39-APC-AF647, α-CCR4-PE, α-HLA-Dr-Pacific Blue, and α-7AAD; or 3) Panel 10c-2 (α-CD4-Krome Orange, α-CD25-PC7, α-CD6-FITC, α-CD127-APC-CF700, α-CD45RA-APC-AF750, α-CD62L-ECD, α-CD39-APC-AF647, α-GARP-PE, α-HLA-Dr-Pacific Blue, and α-7AAD). For multicolor flow cytometry analysis, more than 500,000 cells were analyzed using a flow cytometer (GALLIOS™ Flow Cytometer) and lymphocytes were gated based on forward and side light scatter. CD4$^+$CD25$^+$ lymphocytes were gated CD127 or CD6 expression and then analyzed in a dotplot for one of the other biomarkers. Sample size and data analysis were as described in Example 1.

Figure 9:
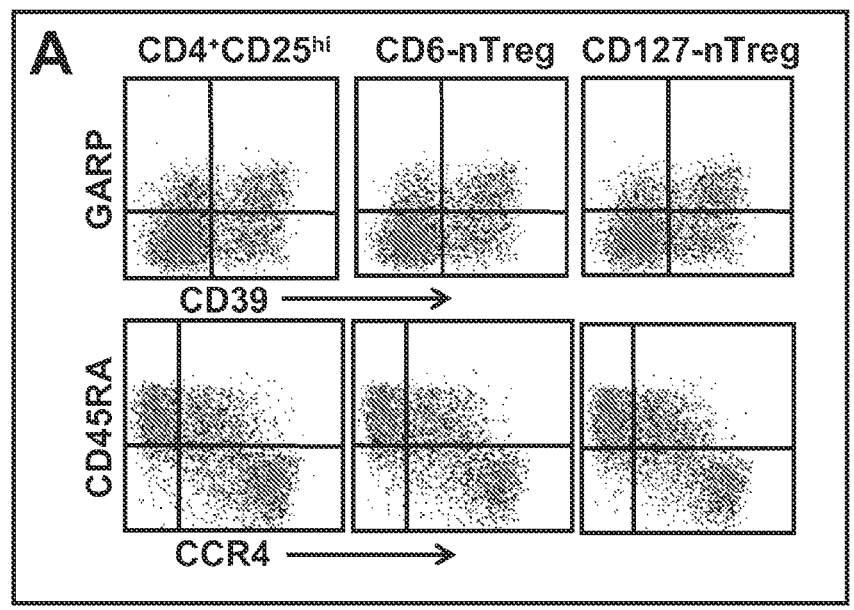
FIG. 9A shows dotplots analyzing CD4$^+$CD25$^+$, CD25$^+$CD6$^{low/-}$, and CD25$^+$CD127$^{low/-}$ lymphocytes for GARP and CD39 expression or CD45RA and CCR4 expression.
FIG. 9B shows dotplots analyzing CD4$^+$CD25$^+$, CD25$^+$/CD6$^{low/-}$, and CD25$^+$CD127$^{lo/-}$ lymphocytes for CD4 and FOXP3 expression, HLA-Dr and FOXP3 expression, or CTLA-4 and FOXP3 expression.
FIG. 9C shows a graph of FOXP3, HLA-Dr, or CTLA-4 expression in CD4$^+$CD25$^+$, CD25$^+$/CD6$^{low/-}$, and CD25$^+$CD127$^{lo/-}$ cell populations. Bar graph shows mean+SD obtained from five healthy control samples.
Figure 9:
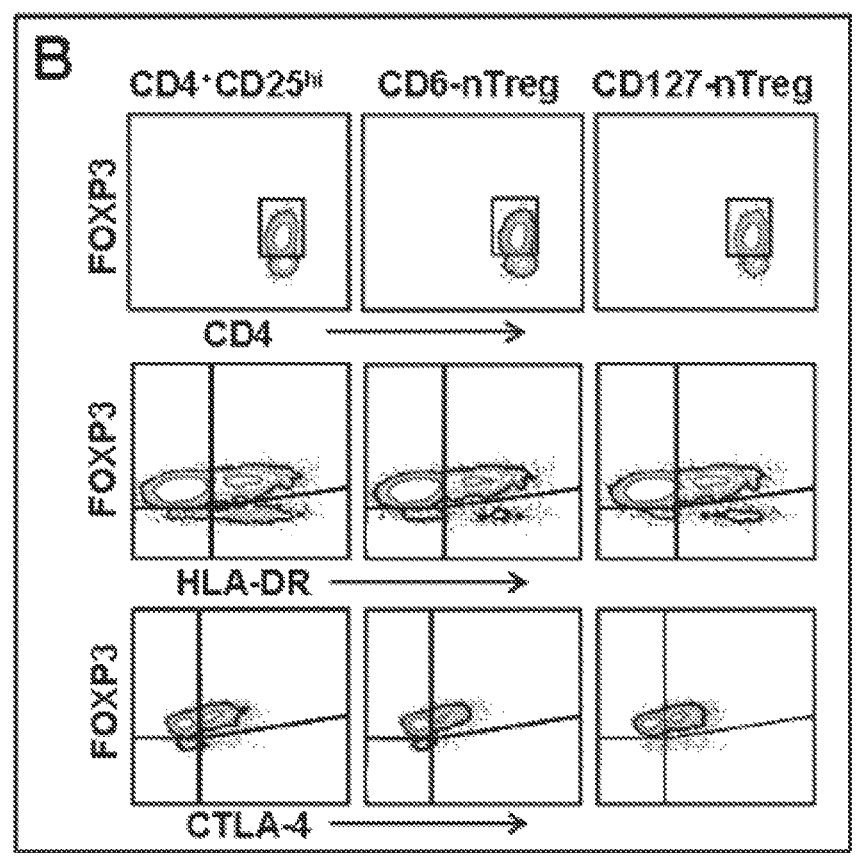
Figure 9:
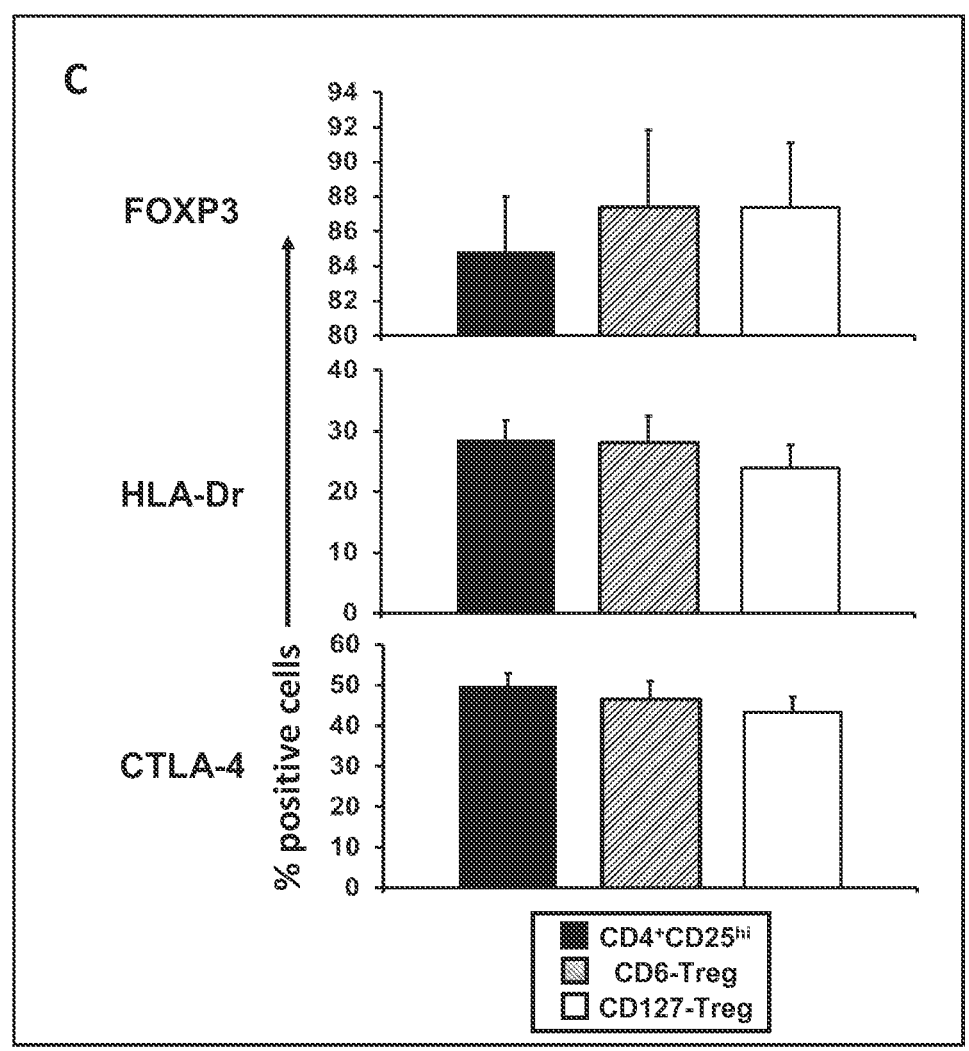

The results indicate that no significant differences were observed between CD4$^+$CD25$^{hi}$CD6$^{lo/-}$ and CD4$^+$CD25$^{hi}$CD127$^{lo/-}$ T$_{reg}$ populations with regards to the expression patterns of biomarkers CCR4, CD39, HLA-DR, CD45RA, GARP, and CTLA-4 (FIGS. 9A, B, & C). Surprisingly, however, heterogeneity in the distribution of HLA-Dr, CCR4, GARP, CD39 and CD45RA biomarker expression was observed within CD4$^+$CD25$^{hi}$CD6$^{lo/-}$ and CD4$^+$CD25$^{hi}$CD127$^{lo/-}$ T$_{reg}$ populations, indicating a potential for different subsets in nT$_{regs}$ that likely represent different stages of cell maturation (FIGS. 9A & B).

Example 10

Characterization of T$_{reg}$-Associated Markers on CD4$^+$CD25$^{hi}$CD6$^{lo/-}$CD127$^{lo/-}$ Cell Population In order to more fully characterize lymphocytes comprising a CD4$^+$CD25$^{hi}$CD6$^{lo/-}$CD127$^{lo/-}$ expression pattern, multicolor flow cytometry analysis was performed using a variety of biomarkers in order to determine whether different stages in nT$_{reg}$ differentiation/maturation pathway could be distinguished.

Human PBMCs were isolated, harvested and stained for cell surface biomarker expression and intracellular biomarker as described in Example 1, except that cells were stained using the following fluorescently-labeled monoclonal antibodies: α-CD4-Krome Orange, α-CD25-PC7, α-CD6-FITC, α-CD127-APC-CF700, α-CD45RA-APC-AF750, α-CD39-APC-AF647, α-CCR4-PE or α-GARP-PE, α-HLA-Dr-Pacific Blue or α-FOXP3-Pacific Blue. For multicolor flow cytometry analysis, more than 500,000 cells were analyzed using a flow cytometer (GALLIOS™ Flow Cytometer) and lymphocytes were gated based on forward and side light scatter. CD4$^+$CD25$^+$ lymphocytes were gated CD127 and CD6 expression and then analyzed in a dotplot for one of the other biomarkers. Sample size and data analysis were as described in Example 1.

Figure 10:
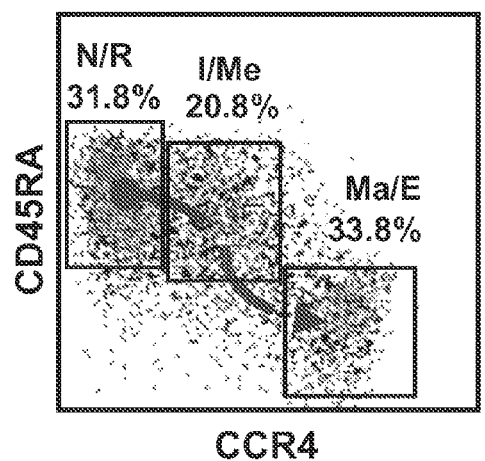
FIG. 10A shows a dotplot analyzing CD4$^+$CD25$^+$CD6$^{low/-}$CD127$^{low/-}$ lymphocytes for CD45RA and CCR4 expression and the identification of three cell population subsets: CD45RA$^+$CCR4$^-$ (naïve/resting, N/R), CD45RA$^+$/CCR4$^{low}$ (immature/memory, I/Me) and CD45RA$^-$/CCR4$^{hi}$ (mature/effectors, Ma/E)
FIG. 10B shows dotplots analyzing N/R, I/Me, and Ma/E population subsets for HLA-Dr and CD39 expression, with arrows showing the direction of marker expression.
FIG. 10C shows a dotplot analyzing CD4$^+$CD25$^{hi}$CD6$^+$CD127$^+$ lymphocytes for CD45RA and CCR4 expression and the identification of cell population subset CCR4$^{hi}$CD39$^-$HLA-DR$^-$ (terminally differentiated, TD)
FIG. 10D shows a dotplot analyzing TD population subset for HLA-Dr and C39 expression.
FIG. 10E shows a graph of the amount of CD25, CD39, HLA-Dr and CD62L expression in N/R, I/Me, Ma/E, and TD population subsets.
FIG. 10F shows dotplots analyzing N/R, I/Me, and Ma/E population subsets defined by CD45RA/CCR4 bivariate analysis by a combination of back-gating and 3-D analysis of nTreg-associated markers in CD6$^{lo/-}$ CD127$^{lo/-}$ nTreg and showing that the majority of HLA-DR$^+$ cells co-express CCR4 and CD39.
FIG. 10G shows a graph of FOXP3 expression in HLA$^-$DR$^-$CD45RA$^+$ (2.3±0.3), HLA$^-$DR$^-$CD45RA$^-$ (3.2±0.3), and HLA$^-$DR$^+$CD45RA$^-$ (5.0±0.7)
FIG. 10H shows dotplots analyzing CD4$^+$CD25$^{hi}$CD6$^{low/-}$CD127$^{low/-}$ nT$_{reg}$ population for CD45RA and GARP expression and the identification of three cell population subsets: CD45RA$^+$GARP$^-$ (Pop1), CD45RA$^-$GARP$^-$ (Pop2) and CD45RA$^-$GARP$^+$ (Pop3), with arrows showing the direction of marker expression.
FIG. 10I shows dotplots analyzing CD4$^+$CD25$^{hi}$CD6$^+$CD127$^+$ nT$_{reg}$ population for CD45RA and GARP expression.
Figure 10:
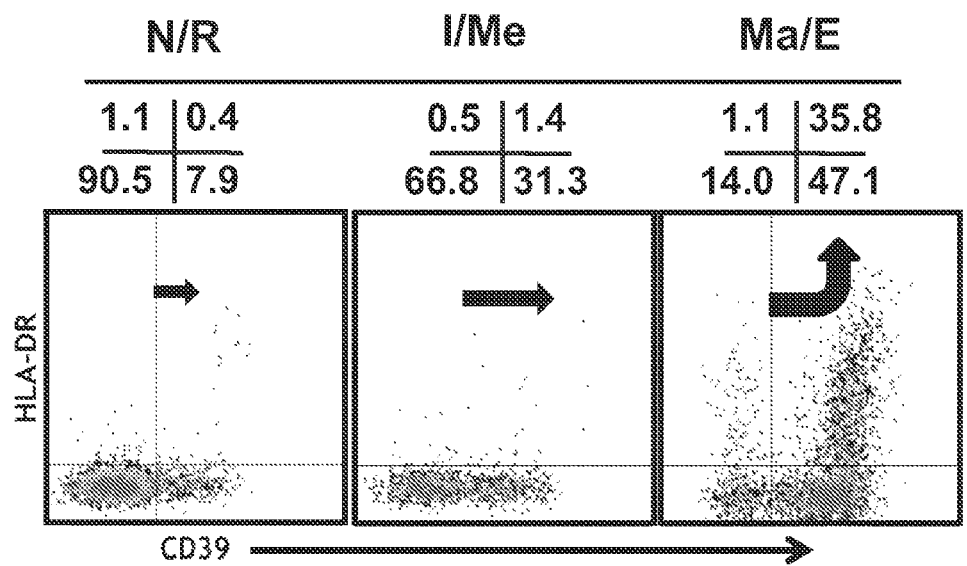
Figure 10:
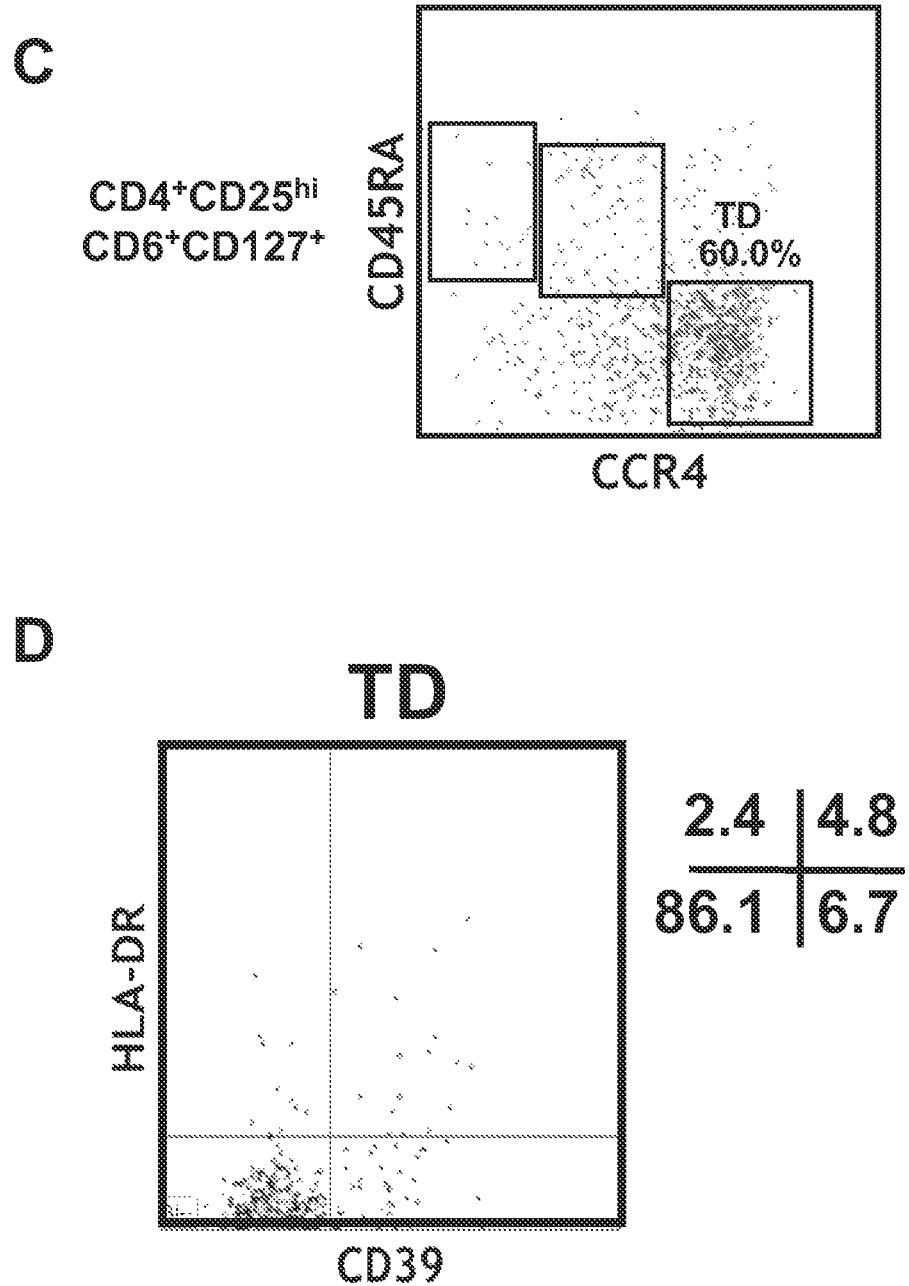
Figure 10:
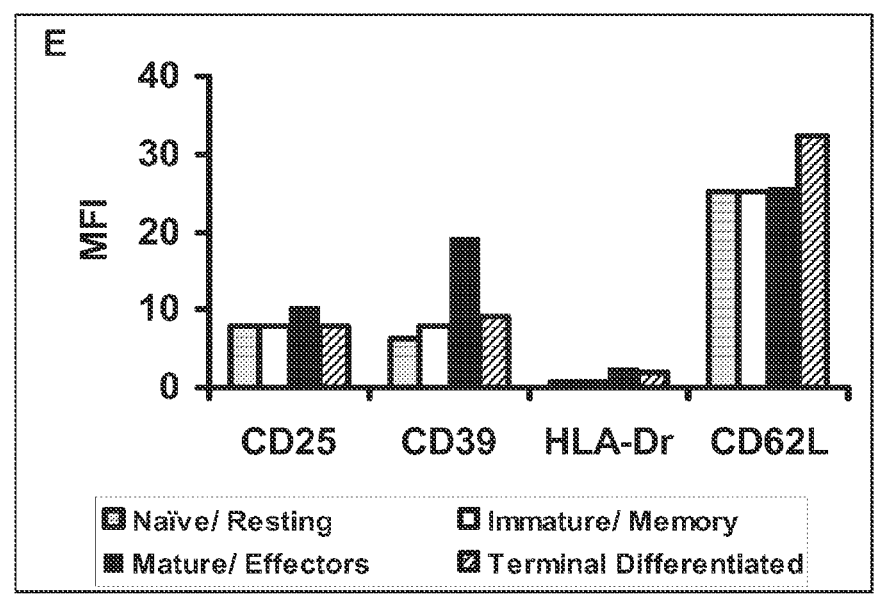
Figure 10:
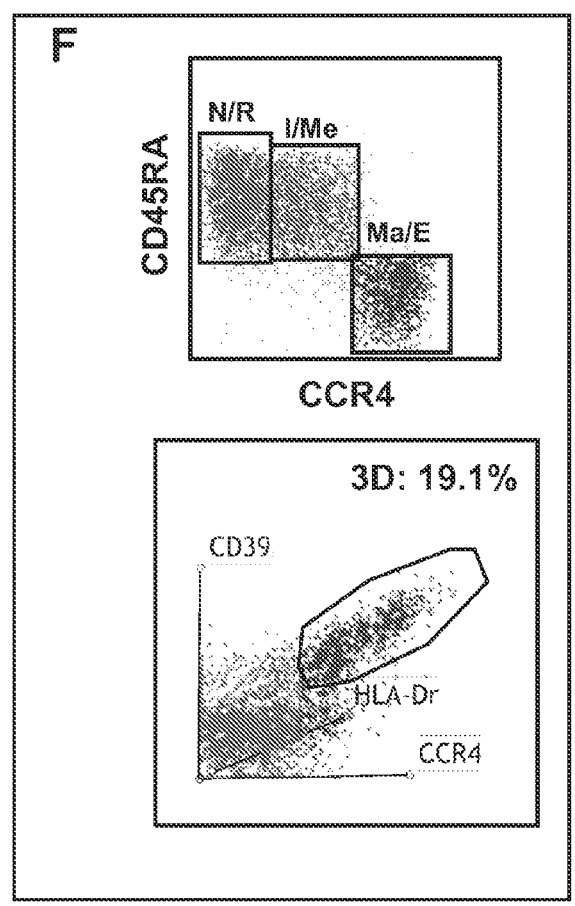
Figure 10:
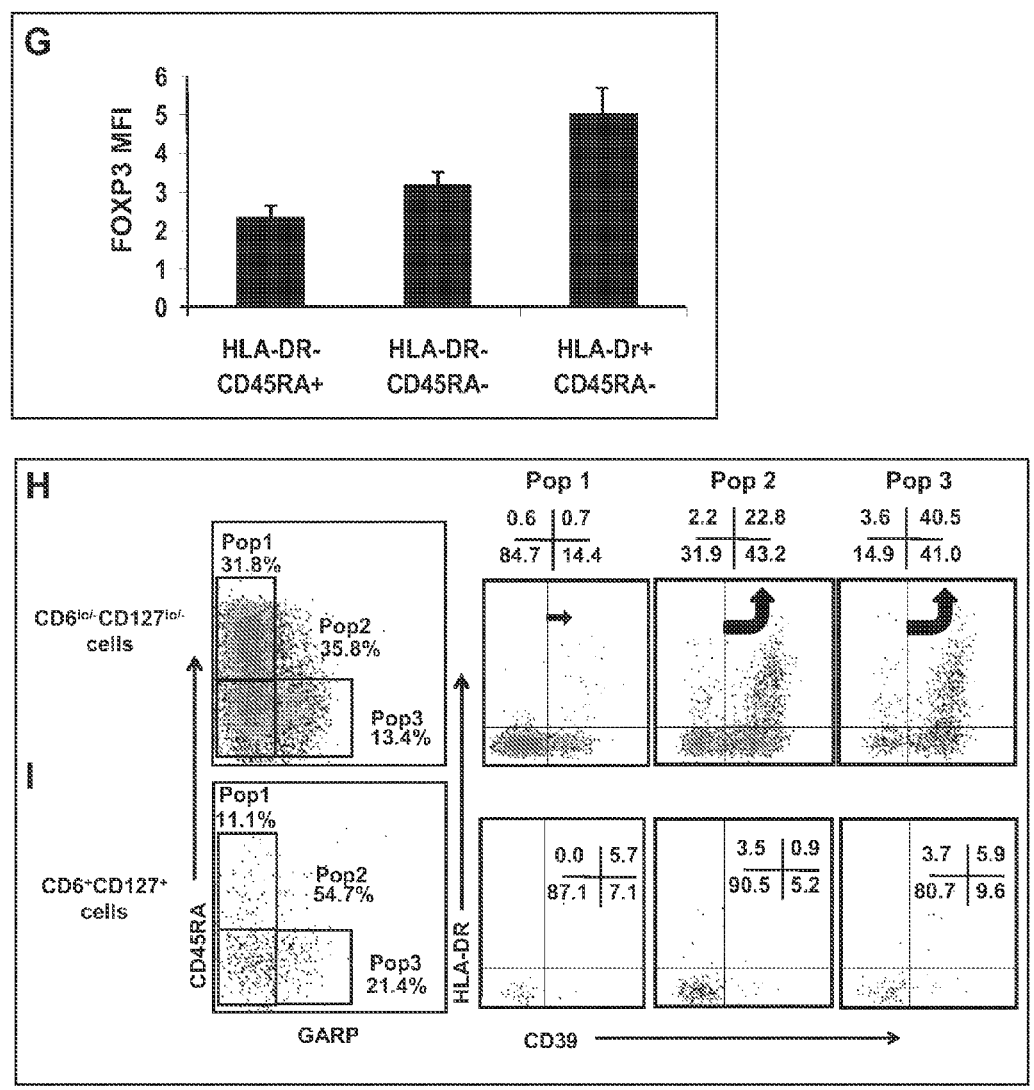

Initially, cells comprising a CD4$^+$CD25$^{hi/+}$CD6$^{lo/-}$CD127$^{lo/-}$ expression pattern where examined for CD45RA expression, in order to discriminate between memory and naïve T-cell stages, and CCR4 expression, as cell homing marker necessary for cell trafficking to local tissues, particularly the skin. The results identified three cell populations: 1) CD45RA$^+$CCR4$^-$, termed the nT$_{reg}$ naïve/resting (NR) subset; 2) CD45RA$^+$CCR4$^{lo}$, termed the immature/memory (I/Me); and 3) CD45RA$^-$CCR4$^{hi}$, termed the mature/effectors (Ma/E) (FIG. 10A). Analysis of CD39 expression in each of these subsets, revealed a progressive increase in CD39 expression through the maturation process with 7.9% CD39 expression in the NR subset; 31.3% CD39 expression in the I/Me subset; and 82.9% CD39 expression in the Ma/E subset. Analysis of HLA-Dr expression indicated that expression was detected in the Ma/E subset (35.8%). Interestingly, almost all of HLA-DR-positive cells co-express CD39 in Ma/E stage (FIG. 10B). These results suggest that HLA-DR expression appears in later stages of nT$_{reg}$ maturation as compared to CD39.

Analysis of cells comprising a CD4$^+$CD25$^+$CD6$^+$CD127$^+$ expression pattern where examined for CD45RA and CCR4 expression. The results revealed that the majority of cells (60%) were CD45RA$^-$ CCR4$^{hi}$ (FIG. 10C) with low expression of CD39 (11.5%) and HLA-Dr (4.8%) (FIG. 10D). This last population revealed a fourth cell population subset in the nT$_{reg}$ differentiation/maturation pathway that appears to represent the terminally differentiated (TD) nT$_{reg}$ subset. Similar results were obtained analyzing MFI for each marker in CD45RA/CCR4 subsets (FIG. 10E). Interestingly, CD62L marker is expressed in whole CD45RA/CCR4 compartment with high MFI expression in nT$_{reg}$-TD subset (FIG. 10E). Using a combination of backgating and 3-D analysis of $T_{reg}$-associated marker expression on the CD4$^+$CD25$^+$CD6$^{lo/-}$CD127$^{lo/-}$ population we observed that the majority of HLA-Dr$^+$ cells co-express CD39 and CCR4 (FIG. 10F).

Finally, examination of FOXP3 MFI expression in different nT$_{reg}$ subsets demonstrated that HLA$^-$ Dr$^+$CD45RA$^-$ subset showed higher FOXP3 expression when compared to HLA-Dr$^-$CD45RA$^-$ and HLA-Dr-CD45RA$^+$ cells, while the double negative HLA-Dr/CD45RA subset demonstrated an intermediate FOXP3 expression (FIG. 10G). Taken together, this expression pattern analysis identified four cell population subsets in the nT$_{reg}$ differentiation/maturation pathway as shown in Table 2.

TABLE 2

Analysis of Natural Regulatory T-Suppressor Cell Differentiation/Maturation Pathway

| Biomarker | Cell Population Subset | | | |
|---|---|---|---|---|
| | Naïve/Resting | Immature/Memory | Mature/Effectors | Terminal Differentiation |
| CD4 | + | + | + | + |
| CD25 | hi | hi | hi | + |
| CD6 | lo/- | lo/- | lo/- | + |
| CD127 | lo/- | lo/- | lo/- | + |
| FOXP3 | lo | lo | hi | lo |
| CD45RA | + | + | - | - |
| CCR4 | - | lo/- | hi | hi |
| CD39 | - | lo | + | lo |
| HLA-Dr | - | lo | lo | lo |

-, less than about 9% detection of biomarker in analyzed cell population.
lo, about 10% to about 49% detection of biomarker in analyzed cell population.
+, about 50% to about 89% detection of biomarker in analyzed cell population.
hi, greater than about 90% detection of biomarker in analyzed cell population.

We also analyzed the CD4$^+$CD25$^{hi/+}$CD6$^{lo/-}$CD127$^{lo/-}$ T$_{reg}$ population using CD45RA and GARP expression. The results identified three CD4$^+$CD25$^+$CD6$^{lo/-}$CD127$^{lo/-}$ cell population subsets: 1) CD45RA$^+$GARP$^-$ (Pop1); 2) CD45RA$^-$GARP$^-$ (Pop2); and 3) CD45RA$^-$GARP$^+$ (Pop3) cells (FIG. 10H). Analysis of CD39 and HLA-Dr expression in each CD45RA/GARP subset showed an increase in CD39 expression from Pop1 to Pop2 and Pop3. However, unlike a previous report showing a positive correlation between GARP expression and activation status of nT$_{reg}$ cells (Wang, et al., *Expression of GARP Selectively Identifies Activated Human FOXP3$^+$Regulatory T Cells*, Proc Natl Acad Sci USA 106: 13439-13444, 2009), HLA-Dr expression was present in both GARP$^-$ (Pop2) and GARP$^+$ (Pop3) subpopulations (FIG. 10H). Moreover, GARP expression was also detected on CD4$^+$CD25$^+$CD6$^+$CD127$^+$ cells (FIG. 10I).

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of identifying and isolating a population of immunosuppressive regulatory T-cells, the method comprising:
    screening, a sample comprising a population of T-cells to detect a level of cellular expression of at least three different biomarkers, the at least three different biomarkers including a CD4 biomarker, CD25 biomarker and a CD6 biomarker; wherein detection of a subpopulation of T-cells comprising a $CD4^+CD25^+CD6^{low/-}$ expression pattern identifies the population of immunosuppressive regulatory T-cells in the sample and wherein detection of the $CD6^{low/-}$ expression comprises fluorescent intensity of below 50%, 40%, 30%, 20% or 10% as compared to fluorescence intensity observed for all cells in the sample, and isolating the subpopulation of immunosuppressive regulatory T-cells.

2. The method of claim 1, wherein the method further comprises enriching the population of immunosuppressive regulatory T-cells.

3. The method of claim 2, wherein the method further comprises contacting the population of immunosuppressive regulatory T-cells with a stimulatory composition thereby expanding population of immunosuppressive regulatory T-cells, wherein the stimulatory composition comprises a T cell receptor (TCR)/cluster of differentiation 3 (CD3) activator that is antigen specific for the population of immunosuppressive regulatory T-cells.

4. The method of claim 1, wherein the screening step further includes screening the sample comprising a population of T-cells to detect a level of cellular expression of a CD127 biomarker, wherein detection of a subpopulation of T-cells comprising a $CD4^+CD25^+CD6^{low/-}CD127^{low/-}$ expression pattern identifies the population of immunosuppressive regulatory T-cells in the sample.

5. The method of claim 1, wherein the screening step further includes screening the sample comprising a population of T-cells to detect a level of cellular expression of a HLA-Dr biomarker, wherein detection of a subpopulation of T-cells comprising a $CD4^+CD25^+CD6^{low/-}HLA-Dr^{low/-}$ expression pattern identifies the population of immunosuppressive regulatory T-cells in the sample.

6. The method of claim 1, wherein the screening step further includes screening the sample comprising a population of T-cells to detect a level of cellular expression of a CD49d biomarker, wherein detection of a subpopulation of T-cells comprising a $CD4^+CD25^+CD6^{low/-}CD49d^{low/-}$ expression pattern identifies the population of immunosuppressive regulatory T-cells in the sample;
    screening the sample comprising a population of T-cells to detect a level of cellular expression of a CD38 biomarker, wherein detection of a subpopulation of T-cells comprising a $CD4^+CD25^+CD6^{low/-}CD38^{low/-}$ expression pattern identifies the population of immunosuppressive regulatory T-cells in the sample;
    screening the sample comprising a population of T-cells to detect a level of cellular expression of a CD45RA biomarker, wherein detection of a subpopulation of T-cells comprising a $CD4^+CD25^+CD6^{low/-}CD45RA^{low/-}$ expression pattern identifies the population of immunosuppressive regulatory T-cells in the sample;
    screening the sample comprising a population of T-cells to detect a level of cellular expression of a FoxP3 biomarker, wherein detection of a subpopulation of T-cells comprising a $CD4^+CD25^+CD6^{low/-}FoxP3^+$ or $CD4^+CD25^+CD6^{low/-}FoxP3^{low/-}$ expression pattern identifies the population of immunosuppressive regulatory T-cells in the sample;
    screening the sample comprising a population of T-cells to detect a level of cellular expression of a CTLA-4 biomarker, wherein detection of a subpopulation of T-cells comprising a $CD4^+CD25^+CD6^{low/-}CTLA-4^+$ or $CD4^+CD25^+CD6^{low/-}CTLA-4^{low/-}$ expression pattern identifies the population of immunosuppressive regulatory T-cells in the sample;
    screening the sample comprising a population of T-cells to detect a level of cellular expression of a GITR biomarker, wherein detection of a subpopulation of T-cells comprising a $CD4^+CD25^+CD6^{low/-}GITR^+$ or $CD4^+CD25^+CD6^{low/-}GITR^{low/-}$ expression pattern identifies the population of immunosuppressive regulatory T-cells in the sample;
    screening the sample comprising a population of T-cells to detect a level of cellular expression of a LAG-3 biomarker, wherein detection of a subpopulation of T-cells comprising a $CD4^+CD25^+CD6^{low/-}LAG-3^+$ or $CD4^+CD25^+CD6^{low/-}LAG-3^{low/-}$ expression pattern identifies the population of immunosuppressive regulatory T-cells in the sample;
    screening the sample comprising a population of T-cells to detect a level of cellular expression of a CD39 biomarker, wherein detection of a subpopulation of T-cells comprising a $CD4^+CD25^+CD6^{low/-}CD39^+$ or $CD4^+CD25^+CD39^{low/-}CD39^{low/-}$ expression pattern identifies the population of immunosuppressive regulatory T-cells in the sample;
    screening the sample comprising a population of T-cells to detect a level of cellular expression of a Helios biomarker, wherein detection of a subpopulation of T-cells comprising a $CD4^+CD25^+CD6^{low/-}Helios^+$ or $CD4^+CD25^+CD6^{low/-}Helios^{low/-}$ expression pattern identifies the population of immunosuppressive regulatory T-cells in the sample;

screening the sample comprising a population of T-cells to detect a level of cellular expression of a FcRL3 biomarker, wherein detection of a subpopulation of T-cells comprising a $CD4^+CD25^+CD6^{low/-}FcRL3^+$ or $CD4^+CD25^+CD6^{low/-}FcRL3^{low/-}$ expression pattern identifies the population of immunosuppressive regulatory T-cells in the sample;

screening the sample comprising a population of T-cells to detect a level of cellular expression of a CCR7 biomarker, wherein detection of a subpopulation of T-cells comprising a $CD4^+CD25^+CD6^{low/-}CCR7^+$ or $CD4^+CD25^+CD6^{low/-}CCR7^{low/-}$ expression pattern identifies the population of immunosuppressive regulatory T-cells in the sample;

screening the sample comprising a population of T-cells to detect a level of cellular expression of a CCR4 biomarker, wherein detection of a subpopulation of T-cells comprising a $CD4^+CD25^+CD6^{low/-}CCR4^+$ or $CD4^+CD25^+CD6^{low/-}CCR4^{low/-}$ expression pattern identifies the population of immunosuppressive regulatory T-cells in the sample;

screening the sample comprising a population of T-cells to detect a level of cellular expression of a CCR8 biomarker, wherein detection of a subpopulation of T-cells comprising a $CD4^+CD25^+CD6^{low/-}CCR8^+$ or $CD4^+CD25^+CD6^{low/-}CCR8^{low/-}$ expression pattern identifies the population of immunosuppressive regulatory T-cells in the sample;

screening the sample comprising a population of T-cells to detect a level of cellular expression of a CD62L biomarker, wherein detection of a subpopulation of T-cells comprising a $CD4^+CD25^+CD6^{low/-}CD62L^+$ or $CD4^+CD25^+CD6^{low/-}CD62L^{low/-}$ expression pattern identifies the population of immunosuppressive regulatory T-cells in the sample;

screening the sample comprising a population of T-cells to detect a level of cellular expression of a ICOS biomarker, wherein detection of a subpopulation of T-cells comprising a $CD4^+CD25^+CD6^{low/-}ICOS^+$ or $CD4^+CD25^+CD6^{low/-}ICOS^{low/-}$ expression pattern identifies the population of immunosuppressive regulatory T-cells in the sample;

screening the sample comprising a population of T-cells to detect a level of cellular expression of a CD103 biomarker, wherein detection of a subpopulation of T-cells comprising a $CD4^+CD25^+CD6^{low/-}CD103^+$ or $CD4^+CD25^+CD6^{low/-}CD103^{low/-}$ expression pattern identifies the population of immunosuppressive regulatory T-cells in the sample;

screening the sample comprising a population of T-cells to detect a level of cellular expression of a PD-1 biomarker, wherein detection of a subpopulation of T-cells comprising a $CD4^+CD25^+CD6^{low/-}PD-1^+$ or $CD4^+CD25^+CD6^{low/-}PD-1^{low/-}$ expression pattern identifies the population of immunosuppressive regulatory T-cells in the sample;

screening the sample comprising a population of T-cells to detect a level of cellular expression of a CD134 biomarker, wherein detection of a subpopulation of T-cells comprising a $CD4^+CD25^+CD6^{low/-}CD134^+$ or $CD4^+CD25^+CD6^{low/-}CD134^{low/-}$ expression pattern identifies the population of immunosuppressive regulatory T-cells in the sample;

screening the sample comprising a population of T-cells to detect a level of cellular expression of a GARP biomarker, wherein detection of a subpopulation of T-cells comprising a $CD4^+CD25^+CD6^{low/-}GARP^+$ or $CD4^+CD25^+CD6^{low/-}GARP^{low/-}$ expression pattern identifies the population of immunosuppressive regulatory T-cells in the sample;

screening the sample comprising a population of T-cells to detect a level of cellular expression of a CD45RB biomarker, wherein detection of a subpopulation of T-cells comprising a $CD4^+CD25^+CD6^{low/-}CD45RB^+$ or $CD4^+CD25^+CD6^{low/-}CD45RB^{low/-}$ expression pattern identifies the population of immunosuppressive regulatory T-cells in the sample;

screening the sample comprising a population of T-cells to detect a level of cellular expression of a CD45RO biomarker, wherein detection of a subpopulation of T-cells comprising a $CD4^+CD25^+CD6^{low/-}CD45RO^+$ or $CD4^+CD25^+CD6^{low/-}CD45RO^{low/-}$ expression pattern identifies the population of immunosuppressive regulatory T-cells in the sample;

screening the sample comprising a population of T-cells to detect a level of cellular expression of a CD95 biomarker, wherein detection of a subpopulation of T-cells comprising a $CD4^+CD25^+CD6^{low/-}CD95^+$ or $CD4^+CD25^+CD6^{low/-}CD95^{low/-}$ expression pattern identifies the population of immunosuppressive regulatory T-cells in the sample;

screening the sample comprising a population of T-cells to detect a level of cellular expression of a CD122 biomarker, wherein detection of a subpopulation of T-cells comprising a $CD4^+CD25^+CD6^{low/-}CD122^+$ or $CD4^+CD25^+CD6^{low/-}CD122^{low/-}$ expression pattern identifies the population of immunosuppressive regulatory T-cells in the sample; and/or screening the sample comprising a population of T-cells to detect a level of cellular expression of a CD8 biomarker, wherein detection of a subpopulation of T-cells comprising a $CD4^+CD25^+CD6^{low/-}CD8^+$ or $CD4^+CD25^+CD6^{low/-}CD8^{low/-}$ expression pattern identifies the population of immunosuppressive regulatory T-cells in the sample.

7. A method of identifying and isolating two or more distinct immunosuppressive regulatory T-cell populations, the method comprising the steps of screening a sample comprising a population of T-cells to detect a level of cellular expression of a CD4 biomarker, a CD25 biomarker, a CD6 biomarker, and one additional biomarker, the one additional biomarker being a FoxP3 biomarker, a CTLA-4 biomarker, a CD45RA biomarker, or a HLA-Dr biomarker;

wherein detection of two distinct populations of immunosuppressive regulatory T-cells is based upon i) T-cells comprising a $CD4^+CD25^+CD6^{low/-}FoxP3^+$ expression pattern and $CD4^+CD25^+CD6^{low/-}FoxP3^{low/-}$ expression pattern, ii) T-cells comprising a $CD4^+CD25^+CD6^{low/-}CTLA-4^+$ expression pattern, and $CD4^+CD25^+CD6^{low/-}CTLA-4^{low/-}$ expression pattern, iii) T-cells comprising a $CD4^+CD25^+CD6^{low/-}CD45RA^+$ expression pattern and $CD4^+CD25^+CD6^{low/-}CD45RA^{low/-}$ expression pattern, or iv) T-cells comprising a $CD4^+CD25^+CD6^{low/-}HLA-Dr^+$ expression pattern and $CD4^+CD25^+CD6^{low/-}HLA-Dr^{low/-}$ expression pattern wherein cells designated as $CD4^+$, $CD25^+$, $FoxP3^+$, $CTLA-4^+$, $CD45RA^+$ or $HLA-Dr^+$ exhibit 10% or more, 20% or more, 30% or more, 40% or more, or 50% or more fluorescence intensity as compared to the fluorescence intensity observed for all cells being screened;

cells designated as $CD6^{low}$, $FoxP3^{low}$, $CTLA\text{-}4^{low}$, $CD45RA^{low}$ or $HLA\text{-}Dr^{low}$ exhibit 50% or less, 40% or less, 30% or less, 20% or less, or 10% or less fluorescence intensity as compared to the fluorescence intensity observed for all cells being screened;

cells designated as $CD6^-$, $FoxP3^-$, $CTLA\text{-}4^-$, $CD45RA^-$ or $HLA\text{-}Dr^-$ exhibit 10% or less, 7% or less, 5% or less, 3% or less, or 2% or less fluorescence intensity as compared to the fluorescence intensity observed for all cells being screened;

and isolating the distinct populations of immunosuppressive regulatory T-cells.

8. The method of claim 7, wherein the method further comprises enriching one or more of the two distinct maturation subsets of immunosuppressive regulatory T-cell populations.

9. The method of claim 8, wherein the method further comprises contacting the one or more of the two distinct maturation subsets of immunosuppressive regulatory T-cell populations with a stimulatory composition thereby expanding population of immunosuppressive regulatory T-cells.

* * * * *